United States Patent
Wu et al.

(10) Patent No.: US 12,050,189 B2
(45) Date of Patent: Jul. 30, 2024

(54) COMPOSITIONS AND METHODS RELATING TO STRUCTURAL DETERMINATION OF SMALL PROTEINS

(71) Applicant: PRESIDENT AND FELLOWS OF HARVARD COLLEGE, Cambridge, MA (US)

(72) Inventors: Xudong Wu, Cambridge, MA (US); Tom A. Rapoport, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 17/930,483

(22) Filed: Sep. 8, 2022

(65) Prior Publication Data
US 2023/0093123 A1 Mar. 23, 2023

Related U.S. Application Data

(60) Provisional application No. 63/242,718, filed on Sep. 10, 2021, provisional application No. 63/242,560, filed on Sep. 10, 2021.

(51) Int. Cl.
| | | |
|---|---|---|
| *G01N 23/20* | (2018.01) | |
| *C07K 14/195* | (2006.01) | |
| *C07K 14/705* | (2006.01) | |
| *C07K 16/46* | (2006.01) | |
| *G01N 33/68* | (2006.01) | |

(52) U.S. Cl.
CPC ........... *G01N 23/20* (2013.01); *C07K 14/195* (2013.01); *C07K 14/705* (2013.01); *C07K 16/465* (2013.01); *G01N 33/6845* (2013.01); *C07K 2299/00* (2013.01); *C07K 2317/569* (2013.01); *C07K 2319/00* (2013.01)

(58) Field of Classification Search
None
See application file for complete search history.

(56) References Cited

FOREIGN PATENT DOCUMENTS

| WO | 2019086548 A1 | 5/2019 | | |
| WO | WO-2019086548 A1 * | 5/2019 | ........... | C07K 14/005 |
| WO | WO-2021104435 A1 * | 6/2021 | ............... | C07K 1/14 |

OTHER PUBLICATIONS

Uchanski et al. Current Opinion in Structural Biologyvol.80, pp. 117-123, 2020. (Year: 2020).*
Lee et al. "Cryo-EM structure of the human L-type amino acid transporter 1 in complex with glycoprotein CD98hc." Nature structural & molecular biology 26.6 (2019): 510-517.
Liu et al. "A 3.8 Å resolution cryo-EM structure of a small protein bound to an imaging scaffold." Nature communications 10.1 (2019): 1-7.
Nygaard et al. "Cryo-electron microscopy analysis of small membrane proteins." Current opinion in structural biology 64 (2020): 26-33.
Tsutsumi et al. "Structure of human Frizzled5 by fiducial-assisted cryo-EM supports a heterodimeric mechanism of canonical Wnt signaling." elife 9 (2020): e58464.
Uchański et al. "Megabodies expand the nanobody toolkit for protein structure determination by single-particle cryo-EM." Nature methods 18.1 (2021): 60-68.
Uchański et al. "Nanobodies to study protein conformational states." Current Opinion in Structural Biology 60 (2020): 117-123.
Wu et al. "Fabs enable single particle cryoEM studies of small proteins." Structure 20.4 (2012): 582-592.
Yao et al. "Fusion of DARPin to aldolase enables visualization of small protein by cryo-EM." Structure 27.7 (2019): 1148-1155.
Yeates et al. "Development of imaging scaffolds for cryo-electron microscopy." Current opinion in structural biology 60 (2020): 142-149.

* cited by examiner

*Primary Examiner* — Jana A Hines
*Assistant Examiner* — Khatol S Shahnan Shah
(74) *Attorney, Agent, or Firm* — Nixon Peabody LLP; David L. Resnick; Nicole D. Kling

(57) ABSTRACT

The technology described herein is directed to structural analysis, particularly of small proteins via cryo-EM.

17 Claims, 32 Drawing Sheets

Specification includes a Sequence Listing.

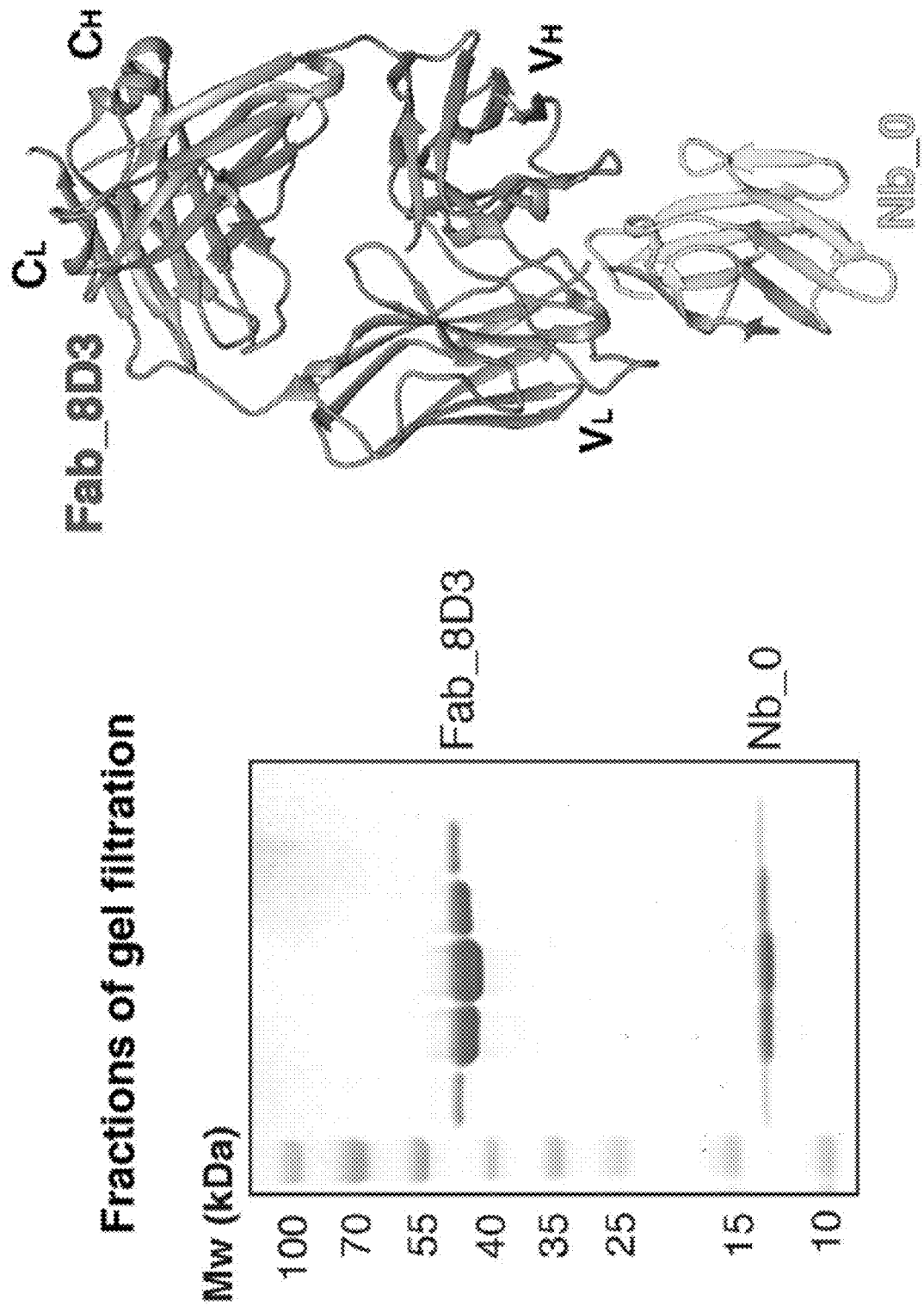

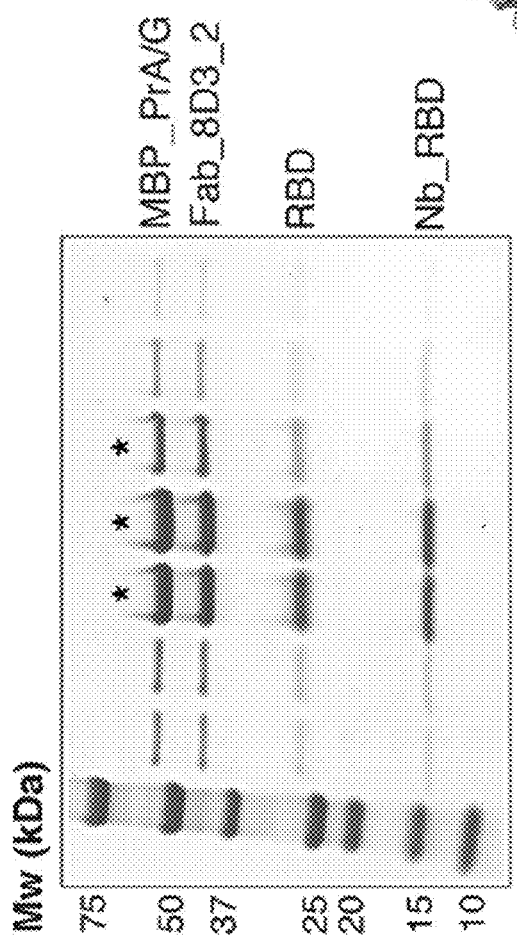
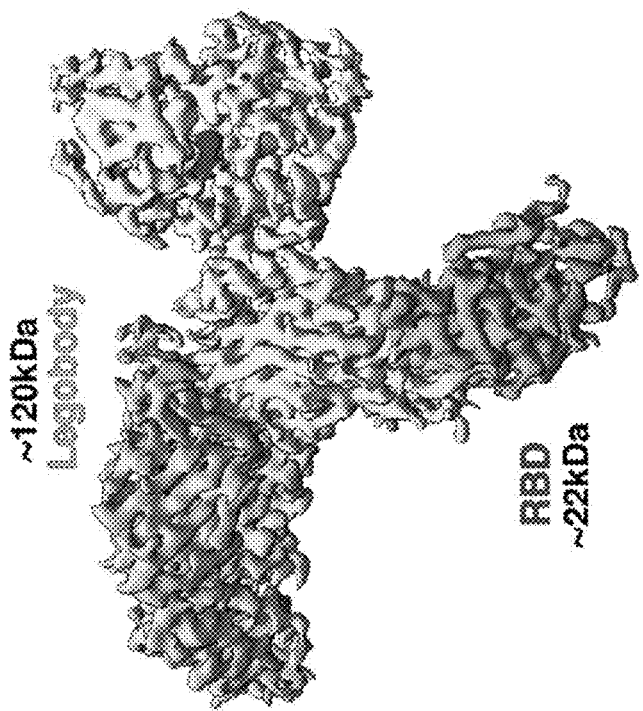
Fig. 5A
Fig. 5B

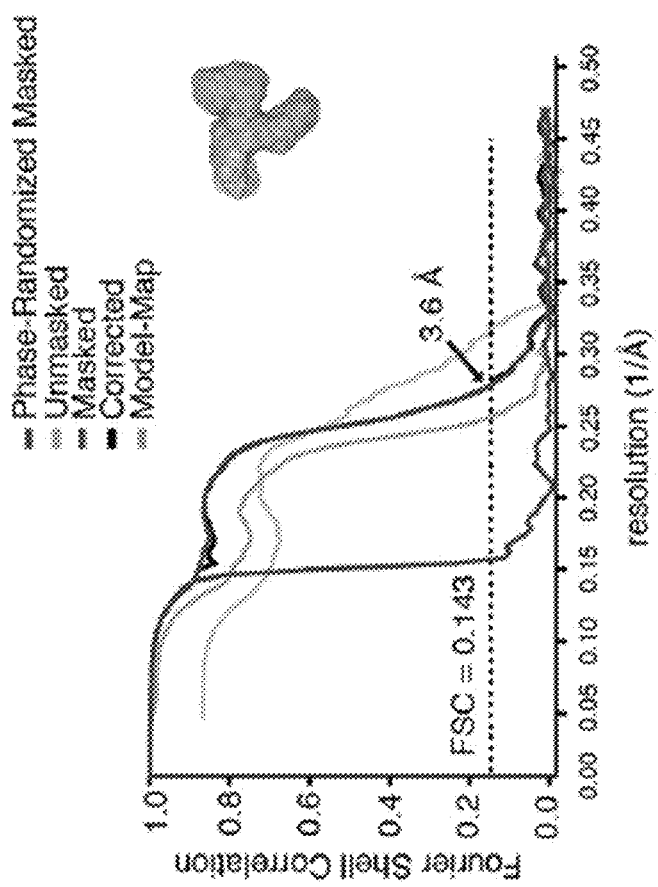
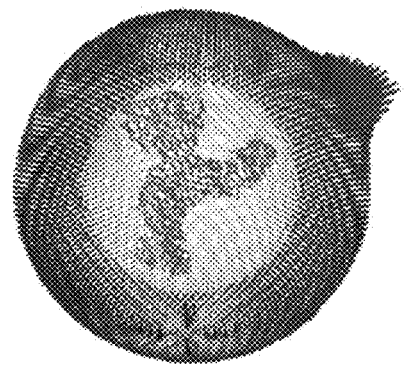
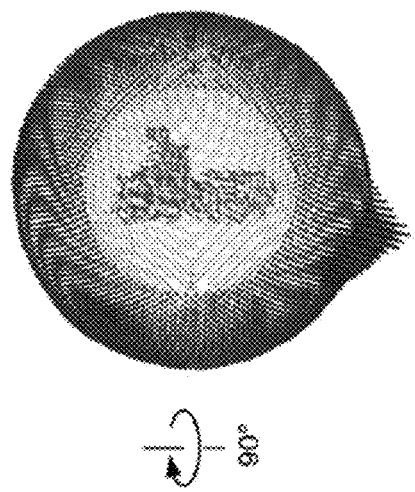
Fig. 10D
Fig. 10E

Small membrane proteins (<100 kDa)

| Target Name | PDB code | No Clash | Clash with PrAD | Clash with MBP_PrAC | Clash with Fab_8D3 |
|---|---|---|---|---|---|
| beta2 adrenoceptor | 3POG | X | | | |
| M2 muscarinic acetylcholine receptor | 4MQS | X | | | |
| succinate receptor | 6IBB | | Possible | | |
| Viral GPCR US28 | 5WB1 | X | | | |
| opioid receptor | 5C1M | | | X | |
| KDEL receptor | 6IJ | X | | | |
| lactose permease | 5GXB | X | | | |
| L-amino acid transporter | 6F2G | | X | | |
| ADP/ATP Carrier | 6GCI | X | | | |

Fig. 12A

Small membrane proteins (<100 kDa)

| Target Name | PDB code | No Clash | Clash with PrAD | Clash with MBP_PrAC | Clash with Fab_8D3 |
|---|---|---|---|---|---|
| dipeptide and tripeptide permease | 6GS4 | X | | | |
| glycine transporter | 6ZBV | X | | | |
| divalent metal ion transporter | 5M94 | | | X | |
| MraY translocase | 8OYH | X | | | |
| insertase BamA | 6OGX | X | | | |

Fig. 12B

Small soluble Proteins (<100 kDa)

| Target Name | PDB code | No Clash | Clash with PrAD | Clash with MBP_PrAC | Clash with Fab_8D3 |
|---|---|---|---|---|---|
| RBD of SARS-CoV-2 | 7KGJ | X | | | |
| ALFA | 6I2G | X | | | |
| GFP | 3K1K | X | | | |
| 3C2 peptide tag | 5IVN | X | | | |
| D3 domain of MTIP | 4GFT | X | | | |
| Complement C3 | 6XZU | X | | | |
| Vsig4 | 5IML | X | | | |
| PorM | 6EYO | X | | | |
| Lysozyme | 3EBA | X | | | |
| Nucleoporin-98 | 7NOW | | | Possible | |
| Gelsolin | 6H1F | X | | | |
| CD38 | 5F1O | X | | | |
| fimbrial adhesin AC | 4W6X | X | | | |
| Surface protein P12p | 7KJI | X | | | |

Fig. 12C

Small soluble Proteins (<100 kDa)

| Target Name | PDB code | No Clash | Clash with PrAD | Clash with MBP_PrAC | Clash with Fab_8D3 |
|---|---|---|---|---|---|
| MAGEB1 | 6RTT | x | | | |
| Capsid protein of norovirus | 5O02 | x | | | |
| Nucleoporin NIC96 | 6X07 | | | x | |
| Complement C1q | 6Z6V | x | | | |
| PD-L1 | 5JDS | x | | | |
| CTLA-4 | 6RQM | x | | | |
| Nup120 | 6X06 | x | | | |
| DHFR | 4EIZ | x | | | |
| GAK kinase | 4C59 | x | | | |
| Synaptojanin1 | 7A17 | x | | | |
| Human prion protein | 4N9O | x | | | |
| CD9 | 6Z1V | x | | | |
| Nup54 | 5C2U | x | | | |
| Urokinase-type plasminogen activator | 5LHP | x | | | |
| EDS1 | 8I8H | x | | | |
| Octarellin V.1 | 5BOP | x | | | |

Fig. 12D

Small soluble Proteins (<100 kDa)

| Target Name | PDB code | No Clash | Clash with PrAD | Clash with MBP_PrAC | Clash with Fab_8D3 |
|---|---|---|---|---|---|
| Capsid protein p24 | 5O2U | x | | | |
| Ricin | 4LGP | x | | | |
| Cyclin-G-associated kinase | 5Y7Z | x | | | |
| CD1d | 6V7Y | x | | | |
| Toxin HigB-2 | 5JA8 | x | | | |
| RhoB | 6SGE | x | | | |
| human serum albumin | 5VNW | | | | x |

Fig. 12E

COMPOSITIONS AND METHODS RELATING TO STRUCTURAL DETERMINATION OF SMALL PROTEINS

CROSS-REFERENCE TO RELATED APPLICATIONS

This application claims benefit under 35 U.S.C. § 119(e) of U.S. Provisional Application No. 63/242,560 filed Sep. 10, 2021 and U.S. Provisional Application No. 63/242,718 filed Sep. 10, 2021, the contents of which are incorporated herein by reference in their entireties.

GOVERNMENT SUPPORT

This invention was made with government support under GM052586 awarded by the National Institutes of Health (NIH). The government has certain rights in this invention.

SEQUENCE LISTING

The instant application contains a Sequence Listing which has been submitted electronically in XML format and is hereby incorporated by reference in its entirety. Said XML copy, created on Sep. 9, 2022, is named 002806-190780US-PT_SL.xml and is 71,996 bytes in size.

TECHNICAL FIELD

The technology described herein relates to the determination of the structure of proteins, e.g, small proteins.

BACKGROUND

Single-particle electron cryo-microscopy (cryo-EM) has become the method of choice for the determination of protein structures. However, the method becomes increasingly challenging for smaller proteins. Large molecules are relatively easy to identify using cryo-EM, the structural analysis of small particles (~100 kDa or less) is much more difficult. Existing technologies that seek to address the difficulty of analyzing small proteins by cryo-EM suffer from failing such as an inability to successfully adapt to a variety of small proteins.

SUMMARY

The technology described herein is directed to a platform that permits cryo-EM analysis of small proteins. The platform, referred to herein as "Legobodies", relates to a set of three different polypeptides that "snap" together similarly to LEGOS, providing a rigid superstructure around a target protein. The platform is highly adaptable and can be easily adapted to a wide variety of target proteins.

In one aspect of any of the embodiments, described herein is a polypeptide composition or kit comprising at least one of:
a. a first polypeptide comprising an antibody, antigen-binding portion thereof, or antibody reagent that specifically binds a target molecule;
b. a second polypeptide comprising an antibody, antigen-binding portion thereof, or antibody reagent that specifically binds the first polypeptide; and
c. a third polypeptide comprising:
  i. at least one maltose binding protein (MBP) domain;
  ii. at least one domain of Protein A; and
  iii. at least one Protein G, Protein L, or Protein M domain.

In some embodiments of any of the aspects, the first polypeptide is a nanobody. In some embodiments of any of the aspects, the first polypeptide is a nanobody comprising a framework sequence with at least 95% sequence identity to the sequence any one of SEQ ID NOs: 24, 29, 34, 39, and 44. In some embodiments of any of the aspects, the first polypeptide is a nanobody comprising the sequence of any one of SEQ ID Nos: 4, 20, 5, 25, 6, 30, 7, 35, 8, and 40.

In some embodiments of any of the aspects, the second polypeptide specifically binds a portion of the first polypeptide that is not a CDR of the first polypeptide. In some embodiments of any of the aspects, the second polypeptide is a Fab. In some embodiments of any of the aspects, the second polypeptide is a Fab comprising the framework sequence of any one of SEQ ID NOs: 58-59. In some embodiments of any of the aspects, the second polypeptide is a Fab comprising the sequence of any one of SEQ ID NOs: 1, 17, 2, 18, 3, or 19.

In some embodiments of any of the aspects, the at least one domain of Protein A comprises or consists of: a domain C of Protein A and a domain D of protein A. In some embodiments of any of the aspects, the at least one MBP domain and the at least one domain of Protein A are provided as a graft of the at least one MBP domain and the at least one domain of Protein A, the graft comprising a sequence with at least 95% sequence identity to the sequence of SEQ ID NO: 45. In some embodiments of any of the aspects, the third polypeptide comprises a sequence with at least 95% sequence identity to the sequence of one of SEQ ID NOs: 9-13, 45 or 46. In some embodiments of any of the aspects, the third polypeptide comprises a sequence with at least 95% sequence identity to the sequence of SEQ ID NO: 46.

In some embodiments of any of the aspects, the kit or polypeptide composition comprises the first polypeptide, the second polypeptide, and the third polypeptide. In some embodiments of any of the aspects, the kit or polypeptide composition further comprises the target molecule. In some embodiments of any of the aspects, the target molecule is a protein. In some embodiments of any of the aspects, the target molecule is 100 kDa or less in size. In some embodiments of any of the aspects, the target molecule is 70 kDa or less in size. In some embodiments of any of the aspects, the target molecule is 50 kDa or less in size. In some embodiments of any of the aspects, the target molecule is at least 3 kDa in size.

In one aspect of any of the embodiments, described herein is a method comprising: a) contacting a target protein with the polypeptide kit or composition described herein, thereby providing a protein complex in which the first polypeptide is bound to the target polypeptide, the second polypeptide is bound to the first polypeptide, and the third polypeptide is bound to the first polytpeptide and the second polypeptide; and imaging the protein complex by cryo-electron microscopy. In some embodiments of any of the aspects, the cryo-electron microscopy is single-particle cryo-electron microscopy. In some embodiments of any of the aspects, the protein is KDEL receptor or SARS-CoV2 spike protein.

BRIEF DESCRIPTION OF THE DRAWINGS

FIGS. 1A-1E depict the generation of two nanobody-interacting scaffolds. FIG. 1A, Nanobody Nb_0 was mixed with Fab_8D3 and the complex was subjected to gel filtration. Fractions were analyzed by SDS-PAGE and Coomassie-blue staining. FIG. 1B, Crystal structure of the Nb_0/Fab_8D3 complex shown in cartoon representation. FIG. 1C, Scheme of the nanobody, with β-strands labeled according to convention. FIG. 1D, Scheme of the interaction of nanobody (Nb) with the domain C of protein A (PrAC) grafted onto maltose-binding protein (MBP). The interacting regions between Nb and MBP_PrAC are shown with dashed lines in between. FIG. 1E, PrAC fused to MBP through a flexible linker (MBP_L_PrAC) or grafted onto MBP (MBP_PrAC) was mixed with Nb. The mixture was incubated with MBP-interacting amylose resin, and the bound material analyzed by SDS-PAGE and Coomassie-blue staining. The input corresponds to 50% of the material used for the pull-down.

FIG. 2A, Scheme of the Legobody assembly. Fab_8D3-2, a derivative of Fab_8D3, and MBP_PrAC bind directly to the nanobody (Nb). The Fab-interacting D-domain of protein A (PrAD) and protein G (PrG) were fused sequentially to the C-terminus of MBP_PrAC via short linkers, generating MBP_PrA/G. Interacting surfaces are highlighted by dashed lines. FIG. 2B, Model of the assembled Legobody in cartoon representation. The model was assembled from structures of Nb_0/Fab_8D3 (FIG. 1B), Fab/PrAD (PDB code 1DEE), and Fab/PrG (PDB code UGC), and by manually building a model for MBP_PrAC from the structures of MBP (PDB code 1ANF) and PrAC (PDB code 4PND). FIG. 2C, Legobody assembled with a nanobody was subjected to gel filtration. Fractions were analyzed by SDS-PAGE and Coomassie-blue staining.

FIG. 3A, Scheme for the purification of the KDELR/Legobody complex. KDELR solubilized in detergent was immobilized on streptavidin beads. The resin was incubated with purified Legobody. Nanodisc-scaffolding protein MSP1D1 and lipids were added, and the reconstitution of nanodiscs initiated by the addition of Biobeads. After extensive detergent removal, the complex was eluted from the resin with biotin. FIG. 3B, The eluted complex of KDELR, Legobody, and nanodisc was subjected to gel-filtration and the elution of protein followed by the absorbance at 280 nm (upper panel). Fractions between the indicated dashed lines were analyzed by SDS-PAGE and Coomassie-blue staining (lower panel). Fractions indicated by a star were pooled and used for EM analysis. FIG. 3C, The purified complex was analyzed by negative-stain EM. Shown are representative 2D class averages, with density for MBP, Fab, and nanobody highlighted by arrows.

FIG. 4A, CryoEM map of the KDELR/Legobody complex in nanodiscs at 3.2 Å resolution, shown in two views. The solid line shows the outline of the cryoEM map filtered to 10 Å, which allows the visualization of the nanodisc and flexible PrAD domain (right panel). FIG. 4B, Two views of the final map shaded according to local resolution (see scale on the right). FIG. 4C, Map and fitted model for different segments of the KDELR and for bound phospholipids.

FIGS. 5A-5D depict the cryoEM structure of a complex of the RBD domain of the SARS-CoV-2 spike protein and Legobody. FIG. 5A, Purified RBD was mixed with Legobody containing a nanobody directed against the RBD (Nb_RBD). The sample was subjected to gel filtration and fractions were analyzed by SDS-PAGE and Coomassie-blue staining. Fractions labeled with a star were pooled and used for EM analysis. FIG. 5B, CryoEM map of the RBD/Legobody complex. FIG. 5C, Two views of the final map colored according to local resolution (see scale on the right). FIG. 5D, Map and fitted model for the interface between the RBD and nanobody.

FIG. 6A, Crystals contain both Nb_0 and Fab_8D3. Multiple crystals were pooled and analyzed by SDS-PAGE followed by Coomassie-blue staining. FIG. 6B, Two views of the interacting region of Nb_0 and Fab_8D3. Residues of Nb_0 involved in the interaction are labeled. FIG. 6C, Model of the Nb_0/Fab_8D3 complex in "worms" representation, colored according to the average B-factor of amino acid residues (scale on the right).

FIG. 8A, Representative cryo-EM image with selected particles marked by circles. FIG. 8B Representative 2D class averages of selected particles. FIG. 8C, Cryo-EM processing workflow. Masks used for classification and refinement are indicated. FIG. 8D, Fourier shell correlation (FSC) curves with indicated resolution at FSC=0.143. Some FSC calculations used the mask shown on the side. FIG. 8E, Euler angle distribution of refined particles is shown in two different views.

FIG. 9A, map and fitted models for different parts of the Legobody. FIG. 9B, The cryoEM structure of the KDELR/Nb_KR complex was aligned with the structure determined by X-ray crystallography (PDB code 6I6J). The proteins are shown in cartoon representation.

FIGS. 10A-10F depict cryo-EM analysis of the RBD/Legobody complex and comparison of the cryoEM and crystal structures of the RBD/nanobody complex. FIG. 10A, representative cryo-EM image with selected particles marked by circles. FIG. 10B, Representative 2D class averages of selected particles. FIG. 10C, Cryo-EM processing workflow. Masks used for classification and refinement are indicated. FIG. 10D, Fourier shell correlation (FSC) curves with indicated resolution at FSC=0.143. Some FSC calculations used the mask shown on the side. FIG. 10E, Euler angle distribution of refined particles is shown in two different views. FIG. 10F, The cryoEM structure of the RBD/Nb_RBD complex was aligned with the structure determined by X-ray crystallography (PDB code 7KGJ). The proteins are shown in cartoon representation.

FIG. 11A, Structure of the complex of the original ALFA nanobody with the ALFA peptide. The model shows the polypeptides in cartoon representation. Residues shown as sticks deviate from those seen in the common nanobody framework and would interfere with the assembly into a Legobody. They were therefore mutated to generate Nb_ALFA. FIG. 11B, To demonstrate that Nb_ALFA can be assembled into the Legobody without loss of antigen binding, purified Legobody containing Nb_ALFA was incubated with or without a GST fusion of ALFA peptide (GST_ALFA peptide). The samples were incubated with glutathione beads and the bound material analyzed by SDS-PAGE and Coomassie-blue staining. The input corresponds to 50% of the material used for the pull-down.

FIGS. 12A-12E depict tables of the analysis of clashes between Legobody domains and targets. Crystal structures of target/nanobody complexes were aligned with the structure of the Legobody on the basis of the nanobody. Steric clashes with the different Legobody domains are listed. The Figures show only one entry for a target protein if several similar structures have been reported. In some cases, the existences of clashes are uncertain (labeled as "possible").

DETAILED DESCRIPTION

Figures 1C, 1D:
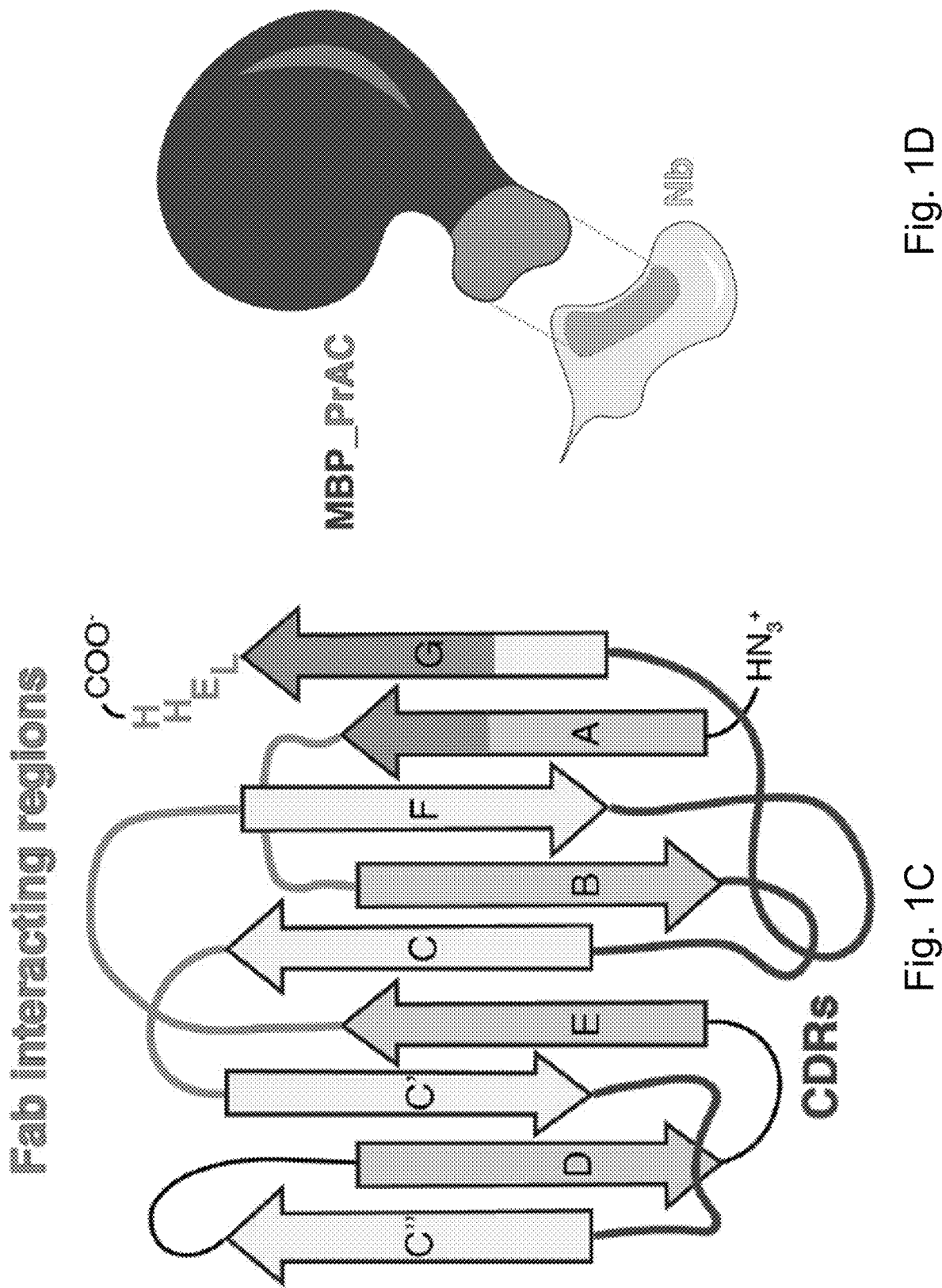

The inventors have developed polypeptides, and sets of polypeptides, that allow them to stabilize target proteins for electron microscopy (e.g., cryo-EM). The approach described herein provides a protein complex with a total size suitable for electron microscopy and which readily adapts to diverse target proteins. The system and approach described herein is at times referred to as "Legobody" or "Legobodies."

In one aspect of any of the embodiments, described herein is a polypeptide composition or kit comprising at least one of:
a) a first polypeptide comprising an antibody, antigen-binding portion thereof, or antibody reagent that specifically binds a target molecule;
b) a second polypeptide comprising an antibody, antigen-binding portion thereof, or antibody reagent that specifically binds the first polypeptide; and
c) a third polypeptide comprising:
  i. at least one maltose binding protein (MBP) domain;
  ii. at least one domain of Protein A; and
  iii. at least one Protein G, Protein L, or Protein M domain.

As used herein, "target molecule" refers to a biological molecule (e.g., peptide, polypeptide, protein, lipid, carbohydrate) to which a domain or moiety can selectively bind. In some embodiments of any of the aspects, target is a receptor, extracellular matrix protein, extracellular protein, ion channel, transporter, peptide, polypeptide, nucleic acid, or microorganism. In some embodiments of any of the aspects, the target molecule comprises a polypeptide or protein. In some embodiments of any of the aspects, the target molecule is a polypeptide or protein.

In some embodiments of any of the aspects, the target molecule is 100 kDa or less in size. In some embodiments of any of the aspects, the target molecule is 90 kDa or less in size. In some embodiments of any of the aspects, the target molecule is 80 kDa or less in size. In some embodiments of any of the aspects, the target molecule is 70 kDa or less in size. In some embodiments of any of the aspects, the target molecule is 60 kDa or less in size. In some embodiments of any of the aspects, the target molecule is 50 kDa or less in size. In some embodiments of any of the aspects, the target molecule is 40 kDa or less in size. In some embodiments of any of the aspects, the target molecule is 30 kDa or less in size. In some embodiments of any of the aspects, the target molecule is 20 kDa or less in size. In some embodiments of any of the aspects, the target molecule is 10 kDa or less in size. In some embodiments of any of the aspects, the target molecule is at least 1 kDa in size. In some embodiments of any of the aspects, the target molecule is at least 2 kDa in size. In some embodiments of any of the aspects, the target molecule is at least 3 kDa in size. In some embodiments of any of the aspects, the target molecule is at least 4 kDa in size. In some embodiments of any of the aspects, the target molecule is at least 5 kDa in size. In some embodiments of any of the aspects, the target molecule is at least 6 kDa in size. In some embodiments of any of the aspects, the target molecule is at least 7 kDa in size. In some embodiments of any of the aspects, the target molecule is at least 8 kDa in size. In some embodiments of any of the aspects, the target molecule is at least 9 kDa in size. In some embodiments of any of the aspects, the target molecule is at least 10 kDa in size.

As described herein, the first polypeptide comprises an antibody, antigen-binding portion thereof, or antibody reagent that specifically binds a target molecule. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some embodiments of any of the aspects, the first polypeptide comprises a nanobody. In some embodiments of any of the aspects, the first polypeptide consists of a nanobody. In some embodiments of any of the aspects, the first polypeptide is a nanobody.

In some embodiments of any of the aspects, the nanbody comprises a framework sequence with a sequence having at least 95% sequence identity to the sequence of any one of SEQ ID NOs: 24, 29, 34, 39, and 44. In some embodiments of any of the aspects, the nanbody comprises a framework sequence with a sequence having at least 98% sequence identity to the sequence of any one of SEQ ID NOs: 24, 29, 34, 39, and 44. In some embodiments of any of the aspects, the nanbody comprises a framework sequence with the sequence of any one of SEQ ID NOs: 24, 29, 34, 39, and 44. It is contemplated that the CDRs can be varied to provide specific binding to a selected target molecule. In some embodiments of any of the aspects, the first polypeptide is a nanobody comprising the sequence of any one of SEQ ID Nos: 4, 20, 5, 25, 6, 30, 7, 35, 8, and 40.

As described herein, the second polypeptide comprises an antibody, antigen-binding portion thereof, or antibody reagent that specifically binds the first polypeptide. In some embodiments of any of the aspects, the second polypeptide consists of an antibody, antigen-binding portion thereof, or antibody reagent that specifically binds the first polypeptide. In some embodiments of any of the aspects, the second polypeptide is an antibody, antigen-binding portion thereof, or antibody reagent that specifically binds the first polypeptide. In some embodiments of any of the aspects, the second polypeptide binds an epitope or portion of the first polypeptide that is not comprised by a CDR of the first polypeptide. In some embodiments of any of the aspects, the second polypeptide binds an epitope or portion of a nanobody framework sequence. In some embodiments of any of the aspects, the second polypeptide binds an epitope or portion of a framework sequence of any one of SEQ ID NOs: 24, 29, 34, 39, and 44.

In some embodiments of any of the aspects, the second polypeptide comprises a Fab. In some embodiments of any of the aspects, the second polypeptide consists of a Fab. In some embodiments of any of the aspects, the second polypeptide is a Fab.

In some embodiments of any of the aspects, the Fab comprises a framework sequence with a sequence having at least 95% sequence identity to any one of SEQ ID NOs: 58-59. In some embodiments of any of the aspects, the Fab comprises a framework sequence with a sequence having at least 98% sequence identity to any one of SEQ ID NOs: 58-59. In some embodiments of any of the aspects, the Fab comprises the framework sequence of any one of SEQ ID NOs: 58-59.

Described herein are Fab sequences comprising CDRs that can specifically bind to the nanobody framework sequences provided herein. Accordingly, in some embodiments of any of the aspects, the Fab comprises the sequence of any one of SEQ ID NOs: 1, 17, 2, 18, 3, or 19. In some embodiments of any of the aspects, the Fab comprises the sequence of any one of SEQ ID NOs: 1, 17, 2, 18, 3, or 19; and the first polypeptide comprises or consists of a nanobody comprising a framework sequence with the sequence of any one of SEQ ID NOs: 24, 29, 34, 39, and 44.

As described herein, the third polypeptide comprises:
i. at least one maltose binding protein (MBP) domain;
ii. at least one domain of Protein A; and
iii. at least one Protein G, Protein L, or Protein M domain.

As used herein, "maltose binding protein" or "MBP" refers to a bacterial protein which is part of the maltose/malodextrin system and participates in the uptake and catabolism of malodextrins and which is encoded by the malE gene. The DNA and polypeptide sequences for MBP are known in the art, e.g., *E. coli* MBP (NCBI Gene ID: 948538, NBCI protein sequence NP_418458.1, as of Sep. 8, 2022 (SEQ ID NO: 56)). Dozens of homologs of *E. coli* MBP are known in the art and their sequences are available, e.g., in the NCBI database. MBP has a precursor form of 396 amino acids and the 26 N-terminal amino acids are cleaved to provide the mature form. In some embodiments of any of the aspects, a MBP domain comprises the mature form of MBP. In some embodiments of any of the aspects, a MBP domain comprises the mature form of *E. coli* MBP.

As used herein, "Protein A" refers to a bacterial protein encoded by the spa gene and which binds Fc and Fab regions of immunoglubulins. The DNA and polypeptide sequences for Protein A are known in the art, e.g., *Staphylococcus* Protein A (NCBI protein sequence WP_000728777.1, as of Sep. 8, 2022 (SEQ ID NO: 57)). Dozens of homologs of Protein A are known in the art and their sequences are available, e.g., in the NCBI database. Protein A comprises 4 to 5 Ig-binding domains, named Domain A, Domain B, Domain C, Domain D, and Domain E. The structure of Protein A is known in the art, e.g, for further discussion see Santos-Junior et la. BMC Microbiology 2016 16:143. In some embodiments of any of the aspects, domain C of Protein A comprises or consists of amino acids 171-206 of SEQ ID NO: 57. In some embodiments of any of the aspects, domain D of Protein A comprises or consists of amino acids 224-233 of SEQ ID NO: 57.

In some embodiments of any of the aspects, a domain of Protein A comprises at least one of domain A, B, C, D, or E of Protein A. In some embodiments of any of the aspects, a domain of Protein A comprises or consists of a domain C of Protein A and a domain D of protein A.

As used herein, "Protein G" refers to a bacterial protein encoded by the isdF gene and which binds Fc and Fab regions of immunoglubulins. The DNA and polypeptide sequences for Protein G are known in the art, e.g., Protein G (UNIPROT protein sequence P06654, as of Sep. 8, 2022). Dozens of homologs of Protein G are known in the art and their sequences are available, e.g., in the NCBI and/or UNIPROT database. The structure of Protein G is known in the art. In some embodiments of any of the aspects, a Protein G domain comprises or consists of amino acids 480-536 of SEQ ID NO: 9.

As used herein, "Protein L" refers to a bacterial protein which binds Fc and Fab regions of immunoglubulins. The DNA and polypeptide sequences for Protein L are known in the art, e.g., Protein L (1YMH in the RCSB database, as of Sep. 8, 2022; see also Akerstrom et al. J Biol Chem 1989 264:19740-6, which is incorporated by reference herein in its entirety). Homologs of Protein L are known in the art and their sequences are available, e.g., in the NCBI and/or UNIPROT database. The structure of Protein L is known in the art.

As used herein, "Protein M" refers to a bacterial protein encoded by the MG281 gene and which binds Fc and Fab regions of immunoglubulins. The DNA and polypeptide sequences for Protein M are known in the art, e.g., Protein M (UNIPROT P47523, as of Sep. 8, 2022). Homologs of Protein M are known in the art and their sequences are available, e.g., in the NCBI and/or UNIPROT database. The structure of Protein M is known in the art.

In some embodiments of any of the aspects, the i) at least one maltose binding protein (MBP) domain; ii) at least one domain of Protein A; and iii) at least one Protein G, Protein L, or Protein M domain can be in any N- to C-terminal order. In some embodiments of any of the aspects, the third polypeptide comprises, from N-terminus to C-terminus: i) at least one maltose binding protein (MBP) domain; ii) at least one domain of Protein A; and iii) at least one Protein G, Protein L, or Protein M domain. In some embodiments of any of the aspects, the third polypeptide comprises, from N-terminus to C-terminus: i) at least one maltose binding protein (MBP) domain; ii) at least one domain of Protein A; and iii) at least one Protein G domain.

In some embodiments of any of the aspects, the third polypeptide comprises, from N-terminus to C-terminus: i) a one maltose binding protein (MBP) domain; ii) at least one domain of Protein A; and iii) a Protein G, Protein L, or Protein M domain. In some embodiments of any of the aspects, the third polypeptide comprises, from N-terminus to C-terminus: i) a one maltose binding protein (MBP) domain; ii) at least one domain of Protein A; and iii) a Protein G domain.

In some embodiments of any of the aspects, the at least one MBP domain and the at least one domain of Protein A are provided as i) a graft of the at least one MBP domain and the at least one domain of Protein A, the graft comprising a sequence with at least 95% sequence identity to the sequence of SEQ ID NO: 45. In some embodiments of any of the aspects, the third polypeptide comprises, from N-terminus to C-terminus: i) a graft of a MBP domain and at least one domain of Protein A, the graft comprising a sequence with at least 95% sequence identity to the sequence of SEQ ID NO; and ii) at least one Protein G, Protein L, or Protein M domain. In some embodiments of any of the aspects, the third polypeptide comprises, from N-terminus to C-terminus: i) a graft of a MBP domain and at least one domain of Protein A, the graft comprising a sequence with at least 95% sequence identity to the sequence of SEQ ID NO; and at least one Protein G domain. In some embodiments of any of the aspects, the third polypeptide comprises, from N-terminus to C-terminus: i) a graft of a MBP domain and at least one domain of Protein A, the graft comprising a sequence with at least 95% sequence identity to the sequence of SEQ ID NO; and a Protein G domain.

In some embodiments of any of the aspects, the third polypeptide comprises a sequence with at least 95% sequence identity to the sequence of any one of SEQ ID NOs: 9-13, 45 or 46. In some embodiments of any of the aspects, the third polypeptide comprises a sequence with at least 98% sequence identity to the sequence of any one of SEQ ID NOs: 9-13, 45 or 46. In some embodiments of any of the aspects, the third polypeptide comprises the sequence of any one of SEQ ID NOs: 9-13, 45 or 46.

In some embodiments of any of the aspects, the third polypeptide comprises a sequence with at least 95% sequence identity to the sequence of SEQ ID NO: 46. In some embodiments of any of the aspects, the third polypeptide comprises a sequence with at least 98% sequence identity to the sequence of SEQ ID NO: 46. In some embodiments of any of the aspects, the third polypeptide comprises the sequence of SEQ ID NO: 46.

In one aspect, described herein is a kit comprising one or more polypeptides as described herein. A kit is any manufacture (e.g., a package or container) comprising at least one article, e.g., a polypeptide described herein, the manufacture being promoted, distributed, or sold as a unit for performing the methods described herein.

The kits described herein can optionally comprise additional components useful for performing the methods described herein. By way of example, the kit can comprise one or more items for suspension or crystallization of the polypeptides or an instructional material which describes performance of a method as described herein, and the like. Additionally, the kit may comprise an instruction leaflet and/or may provide information as to the relevance of the obtained results. Instructions can be printed on a separate leaflet, on the device, or on the packaging of the kit itself.

In some embodiments of any of the aspects, the polypeptide composition or kit comprises or consists of a first polypeptide comprising an antibody, antigen-binding portion thereof, or antibody reagent that specifically binds a target molecule. In some embodiments of any of the aspects, the polypeptide composition or kit comprises or consists of a second polypeptide comprising an antibody, antigen-binding portion thereof, or antibody reagent that specifically binds the first polypeptide. In some embodiments of any of the aspects, the polypeptide composition or kit comprises or consists of a third polypeptide comprising:
  i. at least one maltose binding protein (MBP) domain;
  ii. at least one domain of Protein A; and
  iii. at least one Protein G, Protein L, or Protein M domain.

In some embodiments of any of the aspects, the polypeptide composition or kit comprises or consists of a first polypeptide comprising an antibody, antigen-binding portion thereof, or antibody reagent that specifically binds a target molecule; and a second polypeptide comprising an antibody, antigen-binding portion thereof, or antibody reagent that specifically binds the first polypeptide. In some embodiments of any of the aspects, the polypeptide composition or kit comprises or consists of a first polypeptide comprising an antibody, antigen-binding portion thereof, or antibody reagent that specifically binds a target molecule; and a third polypeptide comprising:
  i. at least one maltose binding protein (MBP) domain;
  ii. at least one domain of Protein A; and
  iii. at least one Protein G, Protein L, or Protein M domain.

In some embodiments of any of the aspects, the polypeptide composition or kit comprises or consists of a second polypeptide comprising an antibody, antigen-binding portion thereof, or antibody reagent that specifically binds the first polypeptide; and a third polypeptide comprising:
  iv. at least one maltose binding protein (MBP) domain;
  v. at least one domain of Protein A; and
  vi. at least one Protein G, Protein L, or Protein M domain.

In some embodiments of any of the aspects, the polypeptide composition or kit comprises or consists of a first polypeptide comprising an antibody, antigen-binding portion thereof, or antibody reagent that specifically binds a target molecule; a second polypeptide comprising an antibody, antigen-binding portion thereof, or antibody reagent that specifically binds the first polypeptide; and a third polypeptide comprising:
  i. at least one maltose binding protein (MBP) domain;
  ii. at least one domain of Protein A; and
  iii. at least one Protein G, Protein L, or Protein M domain.

In some embodiments of any of the aspects, the polypeptide composition or kit further comprises or consists of the target molecule.

In some embodiments of any of the aspects, the target molecule comprises a KDEL receptor or a SARS-CoV2 spike protein.

In one aspect of any of the embodiments, described herein is a method comprising: contacting a target protein with the polypeptide kit or composition comprising the first, second, and third polypeptides described herein, thereby providing a protein complex in which the first polypeptide is bound to the target polypeptide, the second polypeptide is bound to the first polypeptide, and the third polypeptide is bound to the first polytpeptide and the second polypeptide; and imaging or detecting the protein complex by electron microscopy.

Electron microscopy is well known in the art, and electron microscopes and reagents for their use are commercially available. In some embodiments of any of the aspects, the electron microscopy is cryo-electron microscopy. In some embodiments of any of the aspects, the cryo-electron microscopy is single-particle cryo-electron microscopy.

In one respect, the present invention relates to the herein described compositions, methods, and respective component(s) thereof, as essential to the technology, yet open to the inclusion of unspecified elements, essential or not ("comprising"). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "CDR" refers to the complementarity determining regions within antibody variable sequences. The exact boundaries of these CDRs have been defined differently according to different systems. CDRs may be defined according to the Kabat system (see Kabat, E. A. et al., 1991, "Sequences of Proteins of Immunological Interest", 5th edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR. The methods and compositions used herein may utilize CDRs defined according to any of these systems.

The term "antigen-binding portion" of an antibody refers to one or more portions of an antibody as described herein, said one or more portions still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only VL domains have also been shown to specifically bind to target eptiopes).

Although the two domains of the Fv portion, namely VL and VH, are encoded by separate genes, they may further be linked to one another using a synthetic linker, e.g., a poly-G4S amino acid sequence ('G4S'), and recombinant methods, making it possible to prepare them as a single protein chain in which the VL and VH regions combine in order to form monovalent molecules (known as single chain Fv (ScFv)).

The term "antigen-binding portion" of an antibody is also intended to comprise such single chain antibodies. Other forms of single chain antibodies such as "diabodies" can also be included. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody reagent as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cystein residue, a marker peptide and a C-terminal polyhistidinyl, e.g., hexahistidinyl tag ('hexahistidinyl tag') in order to produce bivalent and biotinylated scFv molecules.

In some embodiments of any of the aspects, the antibody reagent described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments of any of the aspects, the antibody reagent thereof is a fully human antibody. In some embodiments of any of the aspects, the antibody reagent is a humanized antibody or antibody reagent. In some embodiments of any of the aspects, the antibody reagent is a fully humanized antibody or antibody reagent. In some embodiments of any of the aspects, antibody reagent is a chimeric antibody or antibody reagent. In some embodiments of any of the aspects, the antibody reagent is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242).

According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments of any of the aspects, it is possible to make one or more conservative amino acid substitutions of CDR residues without appreciably affecting the binding affinity of the resulting humanized immunoglobulin or human antibody variant. In some embodiments of any of the aspects, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin).

The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments or camelid antibodies and antibody fragments with desired specificity are commercially available, for example, from Ablynx, Ghent, Belgium; ProteinTech, Rosemount, IL; Jackson ImmunoResearch, West Grove, PA; and Abcore, Ramona CA Nanobodies with specificity for a desired target are commercially available, e.g., from As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application 20040161738 published Aug. 19, 2004; which is incorporated by reference herein in its entirety. These features combined with the low antigenicity to humans indicate great therapeutic potential.

In some embodiments of any of the aspects, the antibody reagents described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments of any of the aspects, the antibody reagent is an isolated polypeptide. In some embodiments of any of the aspects, the antibody reagent is a purified polypeptide. In some embodiments of any of the aspects, the antibody reagent is an engineered polypeptide.

In some embodiments of any of the aspects, the antibody reagent or antigen-binding fragment thereof is fully human or fully humanized. In some embodiments of any of the aspects, the antibody reagent or antigen-binding fragment thereof is fully humanized except for the CDR sequences.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of 10-5 to 10-12 moles/liter or less, such as 10-7 to 10-12 moles/liter or less, or 10-8 to 10-12 moles/liter (i.e., with an association constant (KA) of 105 to 1012 liter/moles or more, such as 107 to 1012 liter/moles or 108 to 1012 liter/moles). Any KD value greater than 10-4 mol/liter (or any KA value lower than 104 M-1) is generally considered to indicate non-specific binding. The KD for biological interactions which are considered meaningful (e.g., specific) are typically in the range of 10-10 M (0.1 nM) to 10-5 M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some embodiments of any of the aspects, a reagent that binds specifically has the ability to bind to a target, such as an antigen present on the cell-surface, with a KD 10-5 M (10000 nM) or less, e.g., 10-6 M, 10-7 M, 10-8 M, 10-9 M, 10-10 M, 10-11 M, 10-12 M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody or antigen-binding portion thereof is said to specifically bind an antigen when it preferentially recognizes its target antigen in a complex mixture of proteins and/or macromolecules.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, e.g. binding activity of the full length polypeptide. Conservative substitution variants that maintain the activity of wildtype proteins will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant.

In some embodiments, a polypeptide can be a variant of a sequence described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can bind a target at least 50% as well as wildtype. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

One method of identifying amino acid residues which can be substituted is to align, for example, a human protein to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. binding activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide can comprise one or more amino acid substitutions or modifications. In some embodiments, the substitutions and/or modifications can prevent or reduce proteolytic degradation and/or prolong half-life of the polypeptide in a subject. In some embodiments, a polypeptide can be modified by conjugating or fusing it to other polypeptide or polypeptide domains such as, by way of non-limiting example, transferrin (W006096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

In some embodiments, the methods described herein relate to measuring, detecting, or determining a parameter. As used herein, the term "detecting" or "measuring" refers to observing a signal from, e.g. a probe, label, or target molecule to indicate a parameter of an analyte in a sample. In some embodiments of any of the aspects, measuring can be a quantitative observation.

In some embodiments of any of the aspects, a polypeptide as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, "contacting" refers to any suitable means for delivering, or exposing, a first agent with a second agent. Exemplary delivery methods include, but are not limited to, direct delivery to cell culture medium or a solution, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In all embodiments where a sample is obtained or has been obtained or provided, the sample can be sample taken, obtained, or provided via minimally invasive methods and/or involves only a minor intervention. In some embodiments of any of the aspects, a sample is taken, obtained, or provided by one or more of a blood draw or prick, an epidermal or mucus membrane swab, buccal sampling, saliva sample, a epidermal skin sampling technique, and/or collection of a secreted or expelled bodily fluid (e.g., mucus, urine, sweat, etc), fecal sampling, semen/seminal fluid sampling, or clippings (e.g., of hair or nails). In some embodiments of any of the aspects, the sample comprises, consists of, or consists essentially of blood (or any fraction or component thereof), serum, urine, mucus, epithelial cells, saliva, buccal cells, a secreted or expelled bodily fluid, and/or hair or nail clippings.

Other terms are defined herein within the description of the various aspects of the invention.

All patents and other publications; including literature references, issued patents, published patent applications, and patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A polypeptide comprising one or more of the sequences of SEQ ID NOs: 1-16.
2. A polypeptide comprising one or more of the sequences of SEQ ID NOs: 1-16, excluding the cleavable signal sequences thereof
3. An antibody, antigen-binding portion thereof, or antibody reagent comprising one or more of the CDRs of one of SEQ ID NOs: 1-8.
4. An antibody, antigen-binding portion thereof, or antibody reagent comprising one or more of the CDRs of SEQ ID NO: 4.

5. The antibody, antigen-binding portion thereof, or antibody reagent of paragraph 3 or 4, comprising the three or six CDRs of one of SEQ ID NOs: 1-8.

6. A method of binding or imaging a protein, the method comprising contacting the protein with:
   a. a polypeptide, antibody, antigen-binding portion thereof, or antibody reagent comprising the three CDRs of one of SEQ ID NOs: 4-8;
   b. a polypeptide, nanobody, antibody, antigen-binding portion thereof, or antibody reagent comprising the six CDRs of one of SEQ ID NOs: 1-3; and/or
   c. a polypeptide comprising the sequence of one of SEQ ID NO: 9-14.

7. The method of paragraph 6, wherein the protein is KDEL or SARS-CoV2 spike protein.

In any of the foregoing paragraphs, the polypeptide, nanobody, antibody, antigen-binding portion thereof, or antibody reagent can alternatively comprise a sequence having at least 60%, at least 70%, at least 80%, at least 85%, at least 90%, at least 95%, or greater sequence identity with the indicated SEQ ID NO.

In some embodiments, the present technology may be defined in any of the following numbered paragraphs:

1. A polypeptide composition or kit comprising at least one of:
   a) a first polypeptide comprising an antibody, antigen-binding portion thereof, or antibody reagent that specifically binds a target molecule;
   b) a second polypeptide comprising an antibody, antigen-binding portion thereof, or antibody reagent that specifically binds the first polypeptide; and
   c) a third polypeptide comprising:
      i) at least one maltose binding protein (MBP) domain;
      ii) at least one domain of Protein A; and
      iii) at least one Protein G, Protein L, or Protein M domain.

2. The polypeptide composition or kit of paragraph 1, wherein the first polypeptide is a nanobody.

3. The polypeptide composition or kit of any of the preceding paragraphs, wherein the first polypeptide is a nanobody comprising a framework sequence with at least 95% sequence identity to the sequence any one of SEQ ID NOs: 24, 29, 34, 39, and 44.

4. The polypeptide composition or kit of any of the preceding paragraphs, wherein the first polypeptide is a nanobody comprising the sequence of any one of SEQ ID Nos: 4, 20, 5, 25, 6, 30, 7, 35, 8, and 40.

5. The polypeptide composition or kit of any of the preceding paragraphs, wherein the second polypeptide specifically binds a portion of the first polypeptide that is not a CDR of the first polypeptide.

6. The polypeptide composition or kit of any of the preceding paragraphs, wherein the second polypeptide is a Fab.

7. The polypeptide composition or kit of any of the preceding paragraphs, wherein the second polypeptide is a Fab comprising the framework sequence of any one of SEQ ID NOs: 58-59.

8. The polypeptide composition or kit of any of the preceding paragraphs, wherein the second polypeptide is a Fab comprising the sequence of any one of SEQ ID NOs: 1, 17, 2, 18, 3, or 19.

9. The polypeptide composition or kit of any of the preceding paragraphs, wherein the at least one domain of Protein A comprises or consists of: a domain C of Protein A and a domain D of protein A.

10. The polypeptide composition or kit of any of the preceding paragraphs, wherein the at least one MBP domain and the at least one domain of Protein A are provided as a graft of the at least one MBP domain and the at least one domain of Protein A, the graft comprising a sequence with at least 95% sequence identity to the sequence of SEQ ID NO: 45.

11. The polypeptide composition or kit of any of the preceding paragraphs, wherein the third polypeptide comprises a sequence with at least 95% sequence identity to the sequence of one of SEQ ID NOs: 9-13, 45 or 46.

12. The polypeptide composition or kit of any of the preceding paragraphs, wherein the third polypeptide comprises a sequence with at least 95% sequence identity to the sequence of SEQ ID NO: 46.

13. The polypeptide composition or kit of any of the preceding paragraphs, comprising the first polypeptide, the second polypeptide, and the third polypeptide.

14. The polypeptide composition or kit of any of the preceding paragraphs, comprising the first polypeptide, the second polypeptide, and the third polypeptide.

15. The polypeptide composition or kit of any of the preceding paragraphs, further comprising the target molecule.

16. The polypeptide composition or kit of any of the preceding paragraphs, wherein the target molecule is a protein.

17. The polypeptide composition or kit of any of the preceding paragraphs, wherein the target molecule is 100 kDa or less in size.

18. The polypeptide composition or kit of any of the preceding paragraphs, wherein the target molecule is 70 kDa or less in size.

19. The polypeptide composition or kit of any of the preceding paragraphs, wherein the target molecule is 50 kDa or less in size.

20. The polypeptide composition or kit of any of the preceding paragraphs, wherein the target molecule is at least 3 kDa in size.

21. A method comprising:
   a) contacting a target protein with the polypeptide kit or composition of paragraph 1, thereby providing a protein complex in which the first polypeptide is bound to the target polypeptide, the second polypeptide is bound to the first polypeptide, and the third polypeptide is bound to the first polytpeptide and the second polypeptide; and
   b) imaging the protein complex by cryo-electron microscopy.

22. The method of paragraph 21, wherein the cryo-electron microscopy is single-particle cryo-electron microscopy.

23. The method of paragraph 21 or 22, wherein the protein is KDEL receptor or SARS-CoV2 spike protein.

The technology described herein is further illustrated by the following examples which in no way should be construed as being further limiting.

EXAMPLES

Example 1: Cryo-EM Structure Determination of Small Proteins by Nanobody-Binding Scaffolds (Legobody)

Described herein is a general method that allows structure determination of even the smallest proteins by single-particle cryo-electron microscopy (cryo-EM). The method is based on the availability of a target-binding nanobody, which is then rigidly attached to two scaffolds: (1) a Fab-fragment of an antibody directed against the nanobody, and (2) a nanobody-binding protein A fragment fused to maltose binding protein and Fab-binding domains. The overall ensemble of ~120 kDa, called Legobody, does not perturb the nanobody-target interaction and facilitates particle alignment in cryo-EM images. The method is demonstrated for the KDEL receptor, a 23 kDa membrane protein, resulting in a map at 3.2 Å resolution with density sufficient for de novo model building, and for the 22 kDa RBD of SARS-CoV2 spike protein, resulting in a map at 3.6 Å resolution that allows analysis of the binding interface to the nanobody. The Legobody approach thus overcomes the current size limitations of cryo-EM analysis.

Single-particle electron cryo-microscopy (cryo-EM) has become the method of choice for the determination of protein structures [1]. Compared to X-ray crystallography or NMR, cryo-EM analysis requires only small amounts of purified protein and can be carried out in a short time. However, the method becomes increasingly challenging for smaller proteins. Large molecules are relatively easy to identify in noisy low-dose images of vitrified samples and have sufficient contrast and features to determine their orientation and position for alignment and averaging. The structural analysis of small particles (~100 kDa or less) is much more difficult. Without symmetry, they require optimal conditions, such as high sample homogeneity, protein rigidity, and random particle distribution in thin ice, conditions that are difficult to achieve with most samples. However, structure determination of small proteins is of great interest, as most proteins have sizes below 100 kDa and ~50% are smaller than 50 kDa, including many membrane proteins and proteins of medical importance. It is thus a major goal in the field to expand the use of cryo-EM to the routine analysis of small proteins.

One approach to employ cryo-EM for small proteins is based on phase contrast methods, such as the use of Volta phase plates. This method has been used to determine the structure of streptavidin, a protein of 52 kDa, at 3.2 Å resolution [2]. However, the structure of this protein could be determined even without phase plates [3], likely because streptavidin forms rigid tetramers and the particles display a near-perfect distribution in very thin ice, which greatly facilitates structural analysis. Nevertheless, phase plates are a potential solution to the problems encountered with small proteins.

An alternative strategy is to make the target protein larger, either by fusing it to a rigid scaffold or by using a binding partner. The fusion approach has been tried with different scaffolds. For example, in a recent study, the BRIL domain was fused into a loop of a small GPCR protein by extending helices on both sides of the fusion point; the size of the scaffold was further increased by a Fab directed against the BRIL domain [4]. However, this approach is limited to proteins containing suitable α-helices; their extension has to be customized for each new target to generate a rigid connection, which is difficult to achieve without prior knowledge of the target structure. More promising is the use of a binding partner that can be selected with an efficient screening platform. One possibility is to use modified ankyrin repeat proteins (DARPins). In recent studies, DARPins selected against GFP were grafted onto large scaffolds and used to visualize GFP by cryoEM [5,6]. However, the intrinsic conformational heterogeneity of DARPins may limit their potential to achieve high-resolution structures of small proteins [6]. In addition, so far only a few DARPins have been selected against membrane proteins. Another option is to use Fab fragments of antibodies directed against a small target protein. While Fab fragments are routinely used in X-ray crystallography, only a few examples of their application for cryoEM analysis have been reported [7-9], in part because the selection of appropriate Fabs is not trivial, particularly in the case of membrane proteins. In addition, the size of the Fabs (~50 kDa) and the existence of a somewhat flexible hinge region between the two sub-domains still make structural analysis challenging.

Nanobodies, derived from single-chain antibodies of camelids, are also becoming popular as versatile binding partners of target proteins. Nanobodies have several attractive features. They form rigid structures that can bind to diverse shapes of target proteins, such as loops, convex surfaces, and cavities [10]. They can be selected from immunized camelids or from large in vitro libraries displayed by phages, yeast cells, or on ribosomes [10,11], and they can be produced in large quantities in a fairly short time. They often lock a protein into a fixed conformation, particularly in the case of membrane proteins, and have been used extensively to determine X-ray structures. The small size of nanobodies (12~15 kDa) limits their direct application in cryo-EM, but the problem might be overcome if one could increase their size with a large scaffold. One reported approach is to fuse a scaffold into a loop of the nanobody, generating a "megabody"[12]. However, the linker consisted of β-strands between the nanobody and scaffold, which caused some flexibility and limited the use of the scaffold for particle alignment in cryoEM analysis.

Described herein is a versatile method that allows cryo-EM analysis of even the smallest protein once a tightly binding nanobody is available. The size of the nanobody is increased to ~120 kDa by two rigidly attached scaffolds, which together facilitate particle alignment during cryo-EM analysis with the center of alignment at the position of the nanobody. The overall design is reminiscent of a Lego construction, so we propose to call the scaffolds/nanobody ensemble "Legobody". The utility of the Legobody method is demonstrated by structures of the KDEL receptor, a 23 kDa membrane protein at 3.2 Å resolution, and of the RBD domain derived from the spike protein of the SARS-CoV-2 virus (~22kDa) at 3.6 Å resolution. Both proteins have a size well below the estimated limit for direct cryoEM single-particle analysis [13]. The Legobody approach and variations of it can easily be applied to any target protein and should greatly expand the use of cryo-EM single-particle analysis by overcoming the current size limitations.

Results

Generation of a Nanobody-Binding Fab

A first exemplary nanobody-interacting scaffold is a Fab fragment of an antibody that is directed against a surface present in many nanobodies and not involved in target interaction. To generate such a Fab, monoclonal antibodies were raised in mice against a nanobody (Nb_0) that contains a framework sequence almost identical to that used in two libraries employed for rapid in vitro screening [10,11]. Amino acids in the antigen-interacting complementarity-determining regions (CDRs) of Nb_0 were chosen to minimize the immunogenicity of the antigen-interacting surface (see below for sequence). The nanobody used for immunization and hybridoma screening also contained two mutations in the common framework (S7Y and S17Y), but these ultimately did not affect Fab binding (see below). To select for monoclonals that do not perturb nanobody-antigen interaction, hybridoma clones were screened with a complex of a nanobody against MBP (Nb_MBP) and its antigen MBP [10]. After several rounds of selection, hybridoma clone 8D3 was obtained, which produced monoclonal antibodies that strongly bind to both Nb_0 and the Nb_MBP/MBP complex.

Although it is possible to directly use the antibodies secreted by clone 8D3 to generate Fab fragments, future applications are greatly facilitated if the Fabs can be made recombinantly. To this end, the DNA sequences of the regions coding for the variable regions of the light and heavy chains of clone 8D3 were first determined. These sequences were then combined with the sequences coding for the constant regions of murine IgG1, and both genes were expressed together in HEK293 cells. Because the yield of Fabs was rather low, the constant regions of the light and heavy chains were replaced with those of human IgG. The resulting Fab_8D3 was expressed in HEK293 cells as a secreted protein and purified by Ni-NTA chromatography on the basis of a His-tag attached to the heavy chain. The yield is about 5~8 mg from 1L of cell culture. Recombinantly purified Fab_8D3 forms a stable complex with nanobody Nb_0, as shown by co-migration of the proteins in size-exclusion chromatography (FIG. 1A).

Figures 6A, 6C:
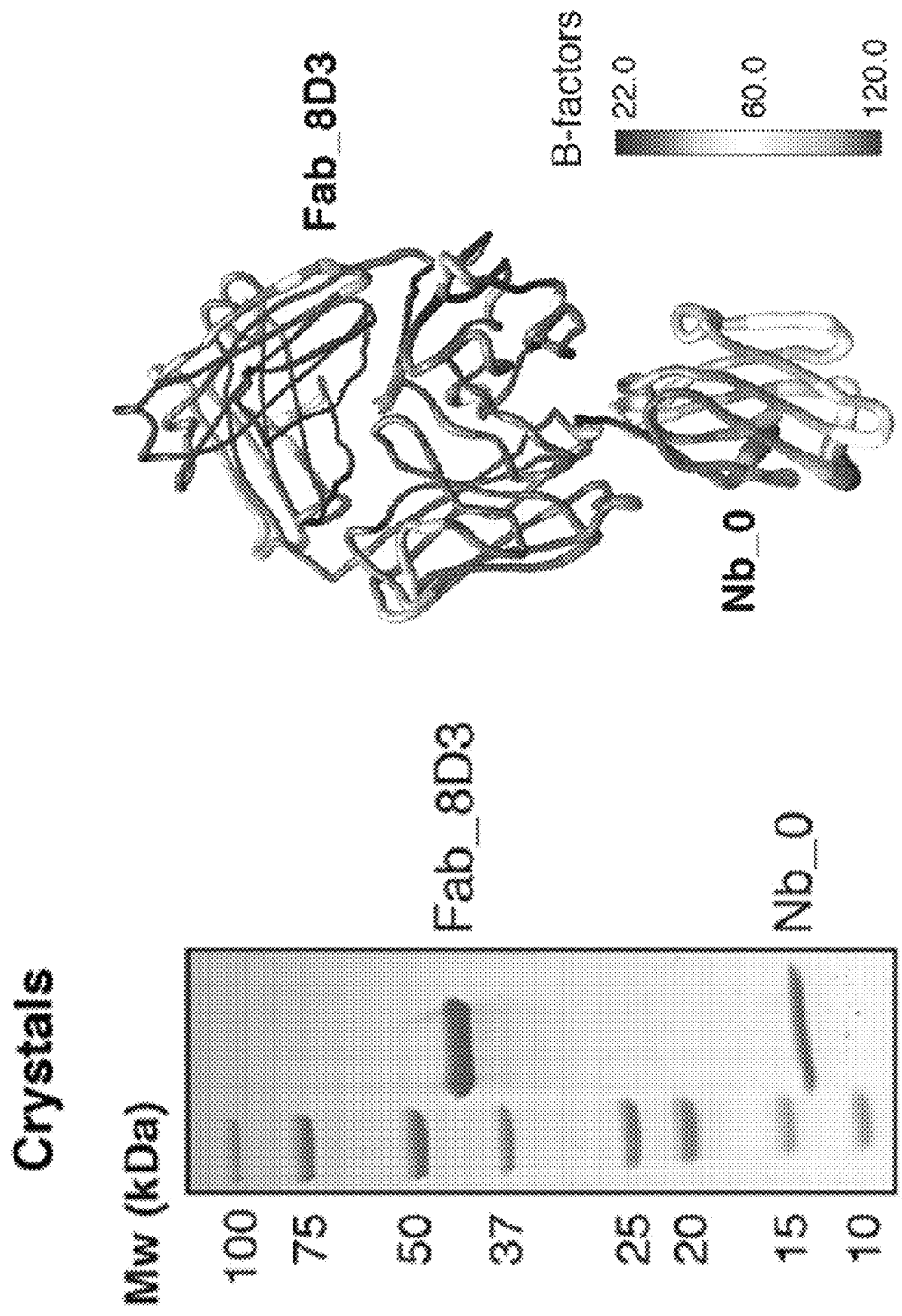
FIGS. 6A-6C depict the crystal structure of a nanobody/Fab complex (Nb_0/Fab_8D3).
Figure 6B:
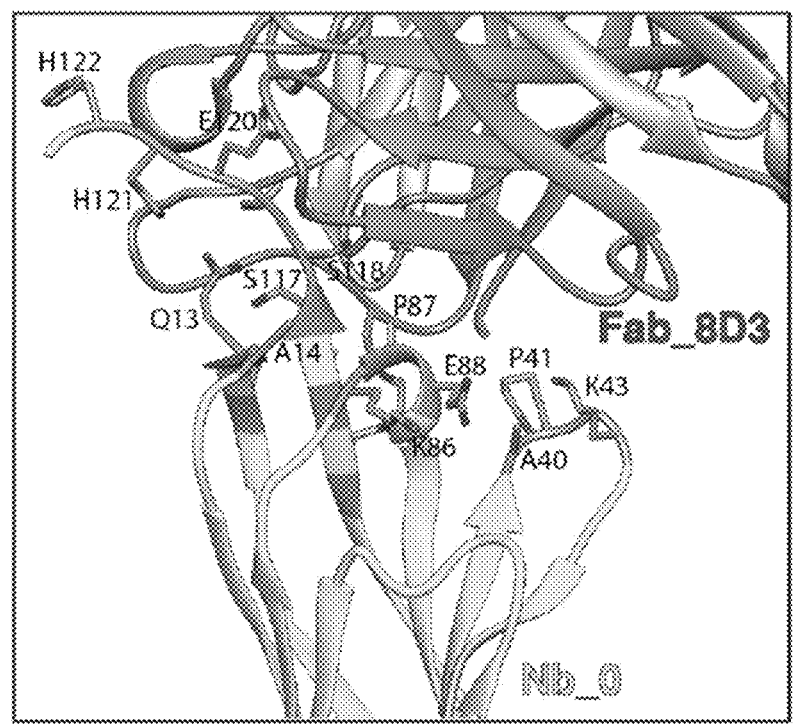
Figure 6B:
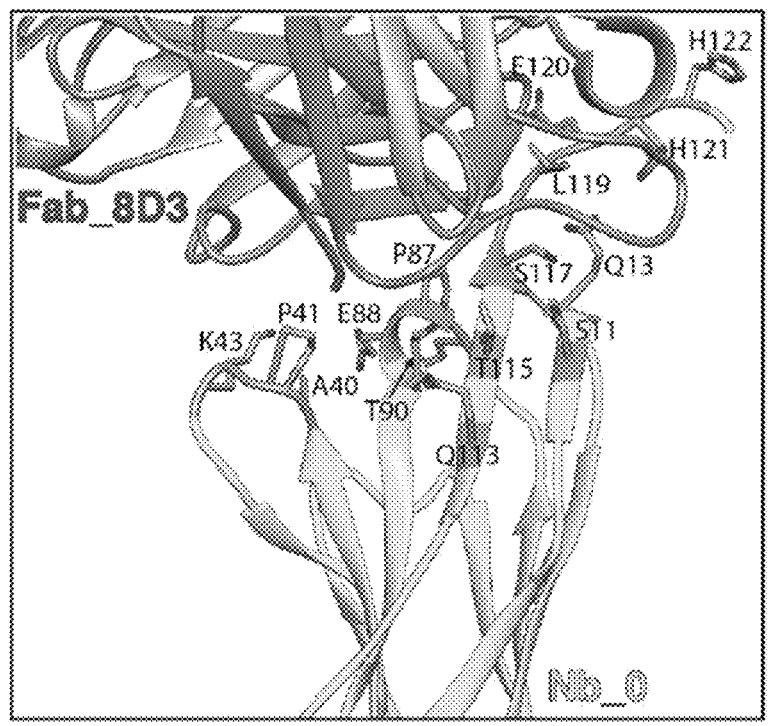

To identify the exact interaction surface, a crystal structure of the complex of Fab_8D3 and Nb_0 was determined. After confirming that the crystals contained both components (FIG. 6A), a structure of the complex was determined at 1.8 Å resolution (FIG. 1B; Table 2). As expected, Fab_8D3 binds to a surface of Nb_0 that is distal from the CDRs and contains conserved amino acids present in many nanobodies (FIG. 1C; FIG. 6B). The Fab-interacting amino acids of Nb_0 are located in loops between β-strands A and B, C and C', E and F, as well as in segments of the β-strands A and G (FIG. 1C). Amino acids introduced by the cloning of the His-tag are also involved. The extensive interactions between the Fab and nanobody generate a rigid interface, a conclusion supported by the B-factor profile of the X-Ray structure (FIG. 6C). The two tyrosines introduced into Nb_0 were not involved in the interaction.

Generation of an MBP-Based Scaffold Interacting with Nanobodies

Figure 7:
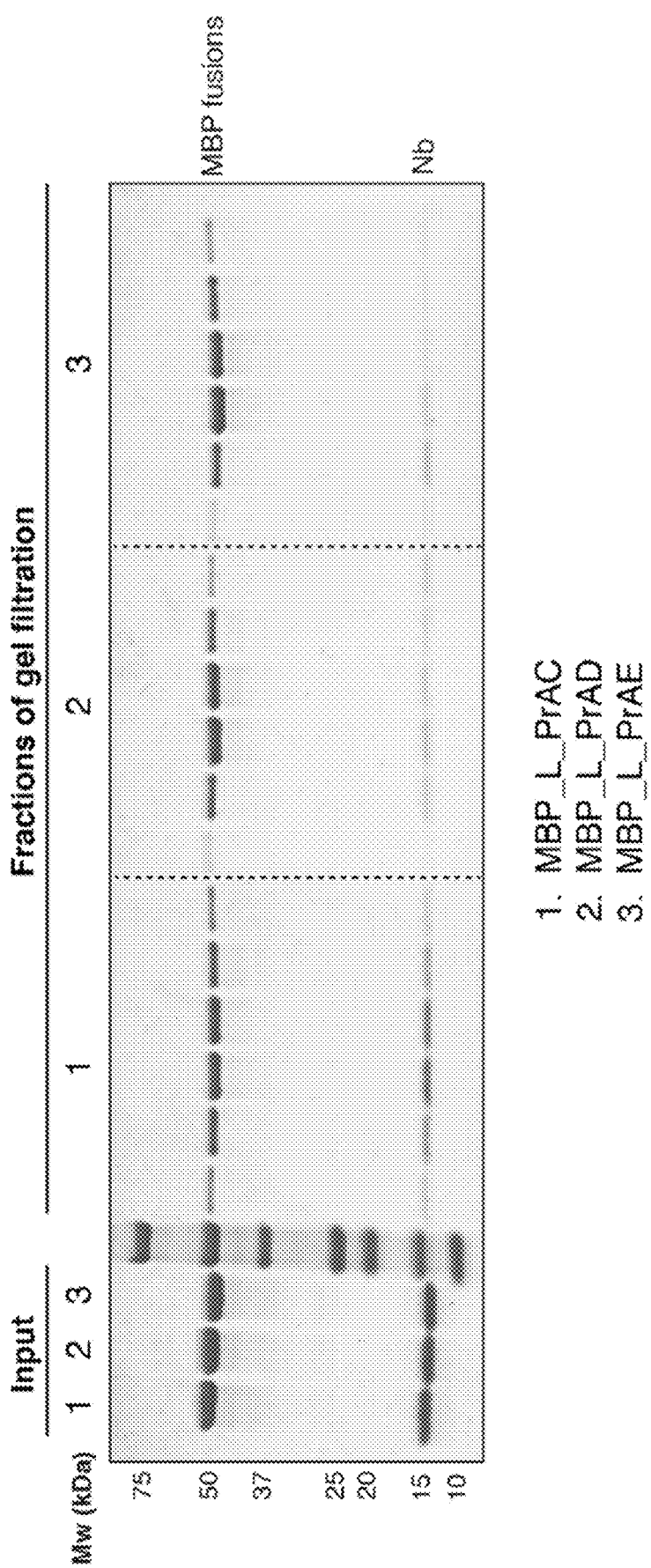
FIG. 7 depicts the interaction of nanobody with different PrA domains. Protein A domains C, D, or E (PrAC, PrAD, PrAE) were fused to MBP via a flexible linker (L). The fusion proteins were mixed with nanobody at a 1:3 molar ratio. The samples were subjected to size-exclusion chromatography and fractions were analyzed by SDS-PAGE and Coomassie-blue staining.
Figure 8A:
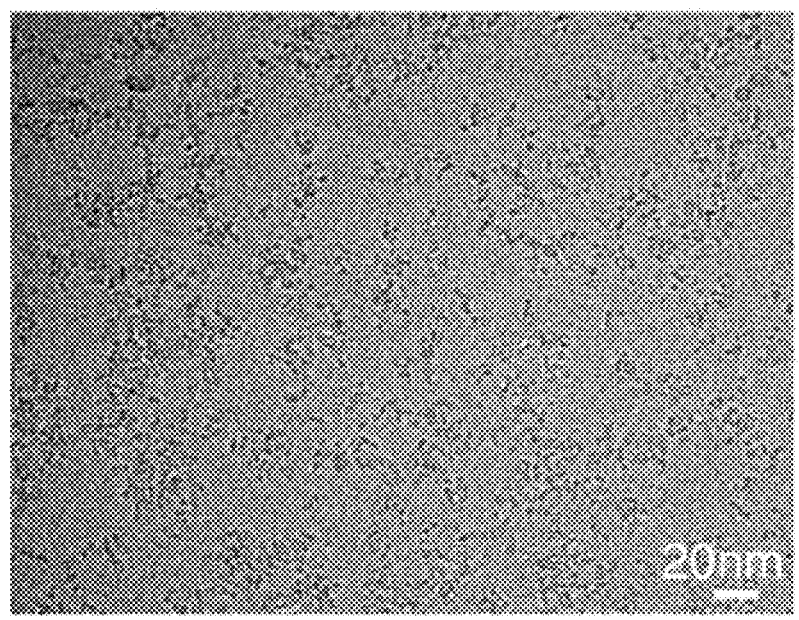
FIGS. 8A-8E depict Cryo-EM analysis of the KDELR/Legobody complex.
Figure 8B:
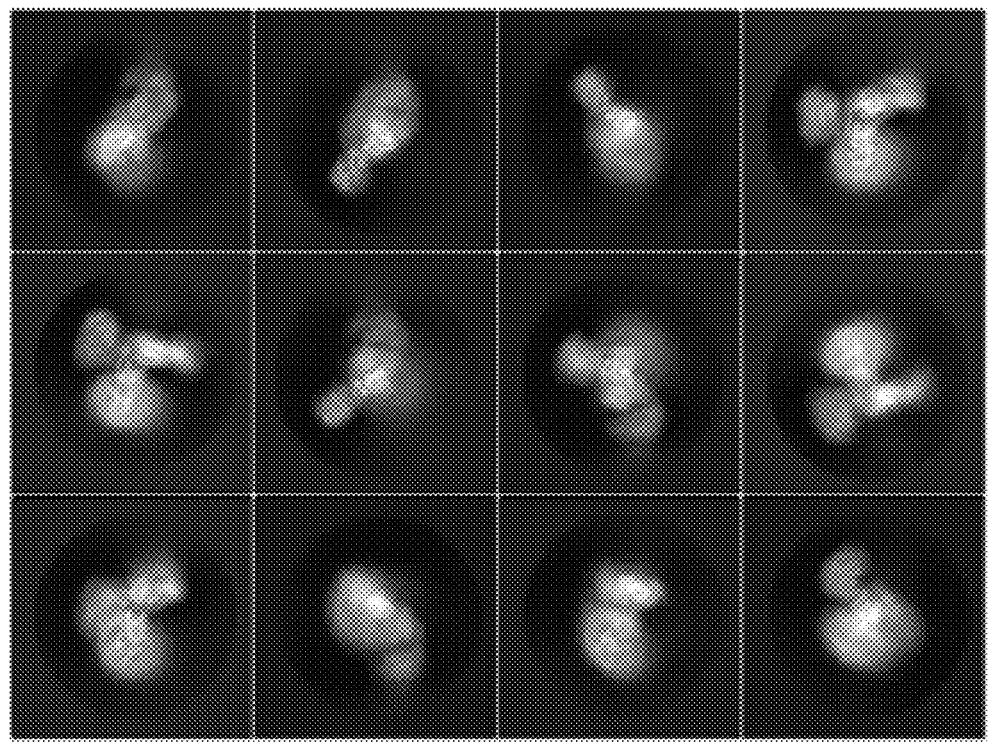
Figure 8C:
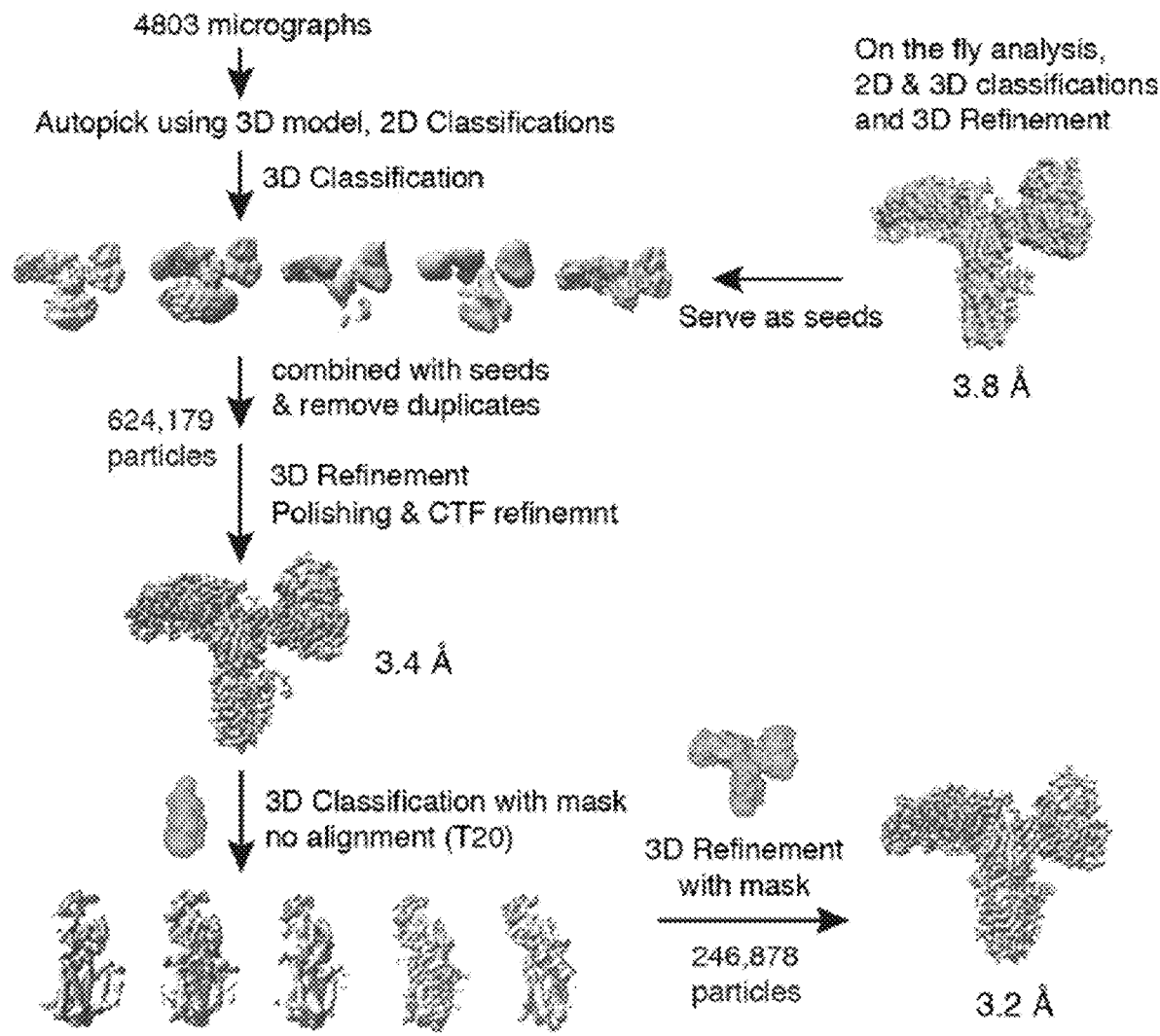
Figure 8D:
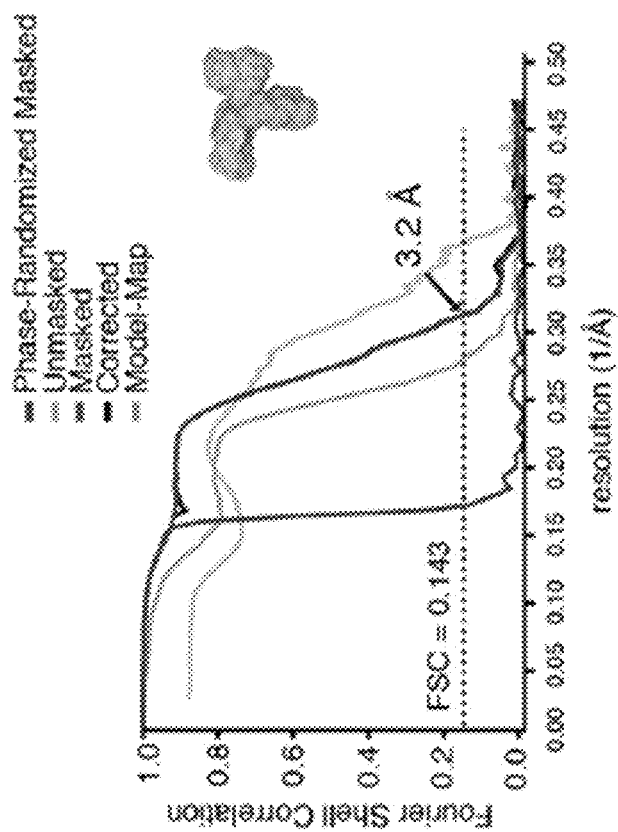
Figure 8E:
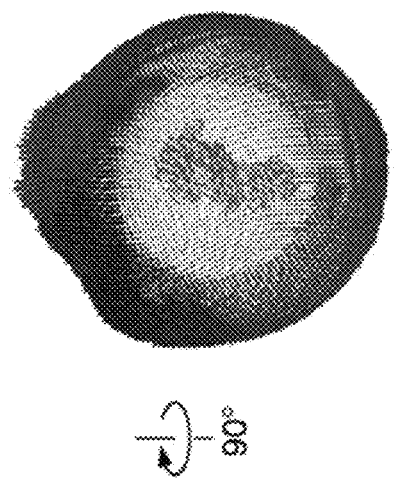
Figure 8E:
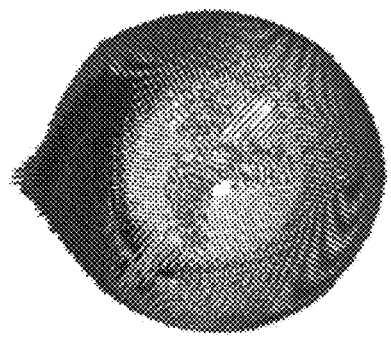

The second scaffold was developed on the basis of reports that protein A from *Staphylococcus aureus* can bind to nanobodies [14]. Protein A contains five repeats of three-helical bundles (domains A, B, C, D and E). All these domains associate with the constant region of IgG antibodies, but also bind with different affinities to the variable region of the heavy chain of some antibodies (human $V_H3$ family) [15], a region that is similar in sequence to the common framework of many nanobodies. Consistent with this sequence homology, protein A has been reported to interact with nanobodies in a similar way as with Fabs [16]. To identify the strongest binding protein A domain, domain D (PrAD) and the most divergent domains C and E (PrAC and PrAE) were fused through a long, flexible linker to MBP (MBP_L_PrAC, MBP_L_PrAD and MBP_L_PrAE) and tested these fusions for their interaction with a nanobody. Co-elution of the proteins in size-exclusion chromatography showed that all three domains interact with the nanobody, but domain C forms the most stable complex (FIG. 7).

Figure 1E:
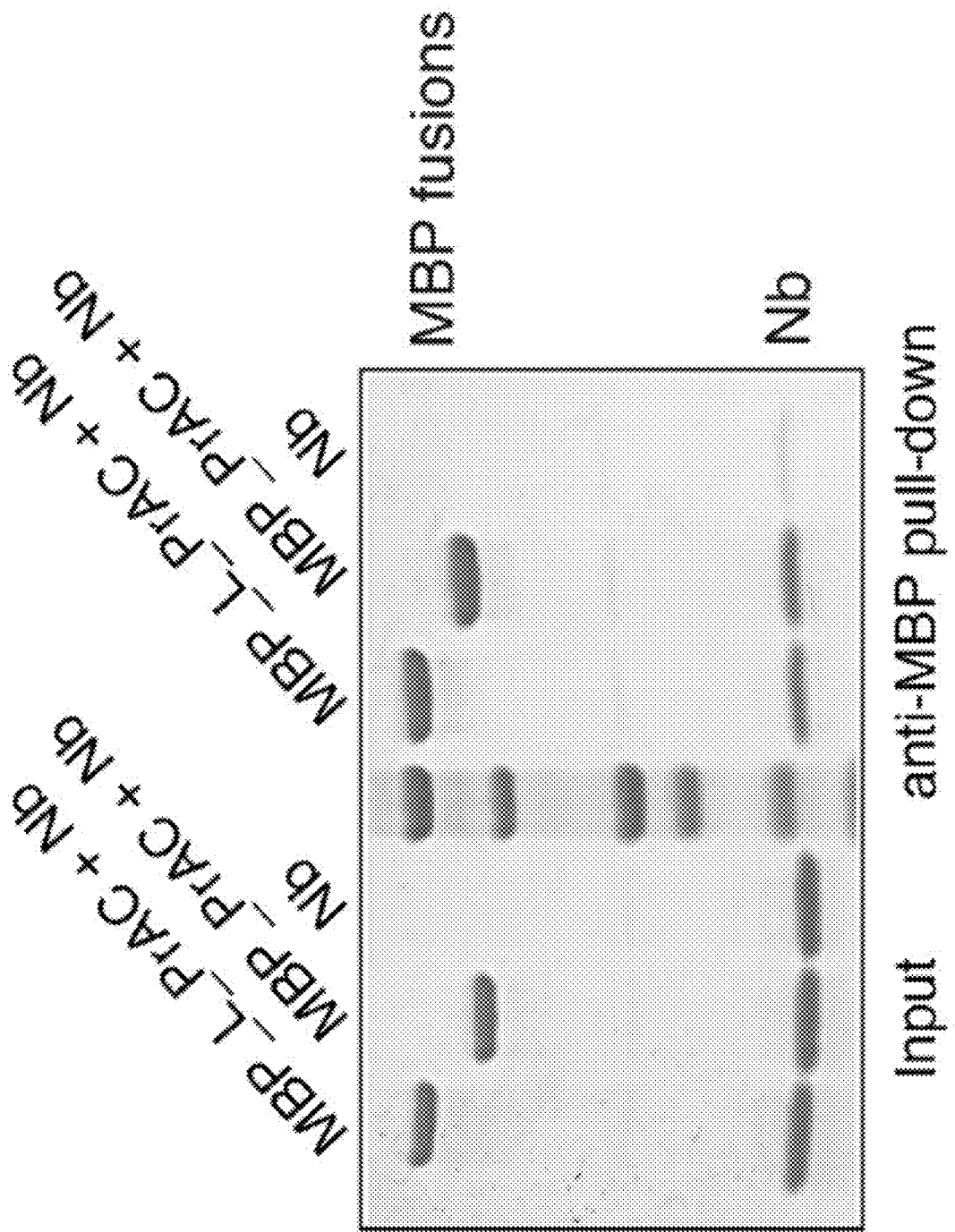

Next, domain C of protein A (PrAC; ~6 kDa) was grafted to MBP to generate a larger nanobody-binding partner. MBP is frequently used as an N-terminal fusion partner, as it can increase the solubility of its fusion partners. Although fusions can be designed as helical extensions of the C-terminal helix of MBP and have been extensively used in X-ray crystallography [17], such linkers are not rigid enough for cryoEM analysis. To generate a more rigid connection between PrAC and MBP, the "shared helix" approach [18] was used, applying it to a helix of domain C that is not involved in nanobody interaction. Residues on one side of this helix were mutated to those of MBP's C-terminal helix that face the core of MBP. The resulting construct MBP_PrAC (FIG. 1D) could be expressed in *E. coli* and purified in large quantities. It also readily crystalized (data not shown), suggesting that it is fairly rigid. Like the MBP fusion of PrAC containing a flexible linker (MBP_L_PrAC), MBP_PrAC interacted with the nanobody in pull-down experiments (FIG. 1E).

Legobody Assembly

Figure 2A:
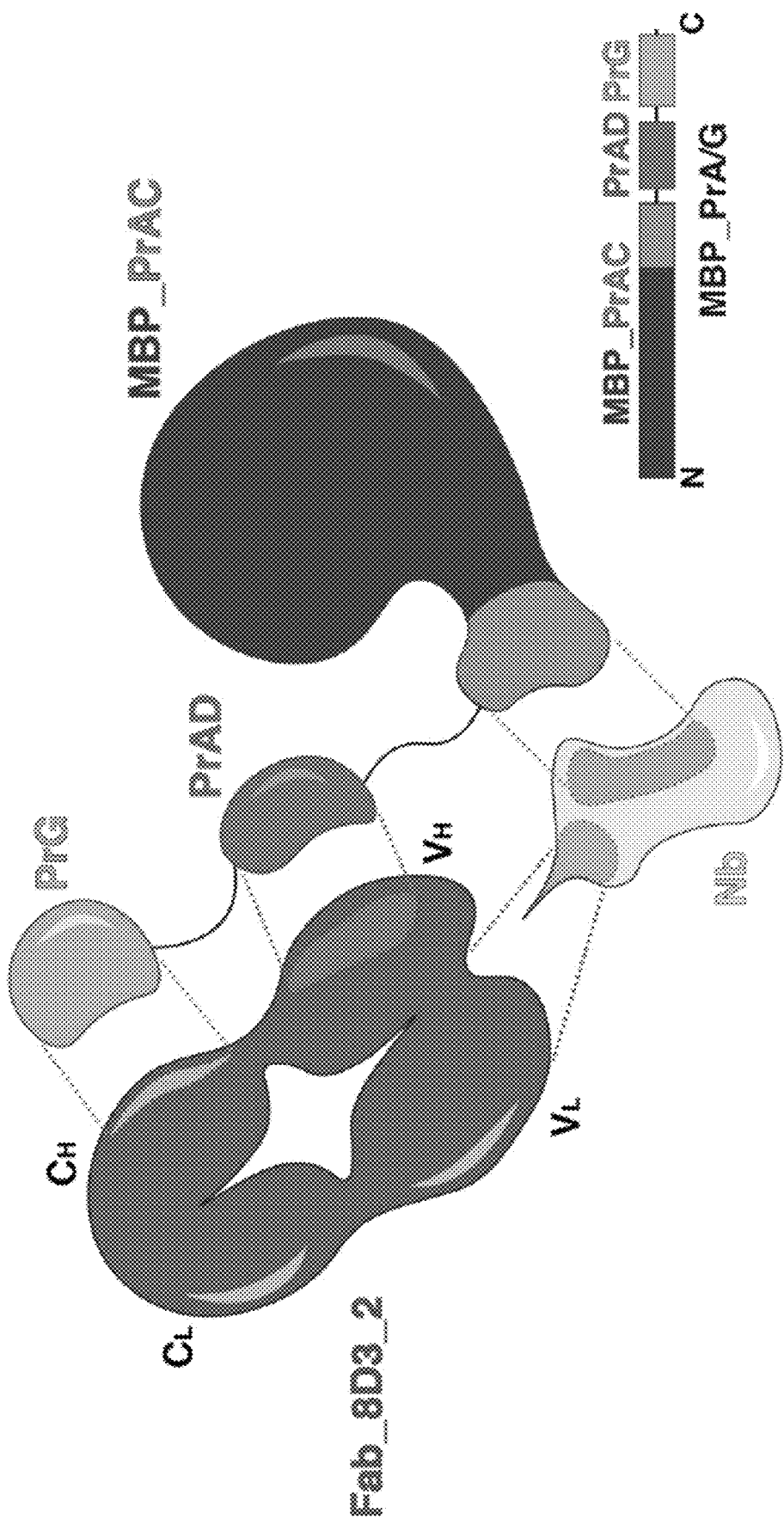
FIGS. 2A-2C depict the assembly and purification of the Legobody.
Figures 2B, 2C, 2D:
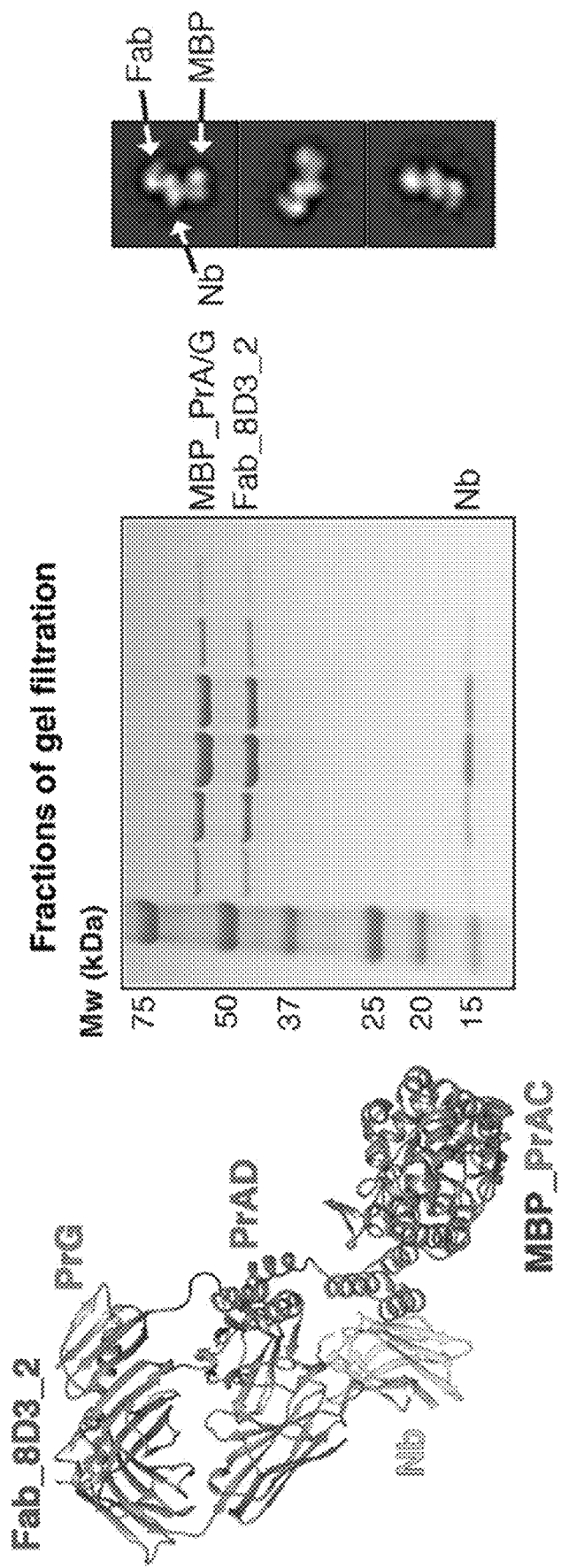
FIG. 2D, Purified Legobody was analyzed by negative-stain EM. Shown are representative 2D class averages, with density for MBP, Fab, and nanobody highlighted by arrows.

The nanobody surfaces interacting with Fab_8D3 and MBP_PrAC are not overlapping (FIGS. 2A and 2B), providing an opportunity to use both scaffolds at the same time. To increase the stability of the ensemble, two Fab-binding domains were fused to the C-terminus of MBP_PrAC. One is the domain D of protein A (PrAD), which has been shown to interact with the variable region of the heavy chain of Fabs [19]. The other is protein G (PrG), which is known to interact with the constant region of the heavy chain [20]. All domains were connected by short linkers, generating a scaffold designated MBP_PrA/G (FIGS. 2A and 2B). To allow the interaction of PrAD with Fab_8D3, some residues in the variable region of the heavy chain were mutated based on the crystal structure of a Fab/PrAD complex (PDB code 1DEE), generating Fab_8D3_2 and MBP_PrA/G.

The complex between Fab_8D3_2 and MBP_PrA/G was assembled before adding a nanobody. All three components co-migrated in size-exclusion chromatography (FIG. 2C). Negative-stain EM showed strong structural features for the Fab, MBP, and the nanobody (FIG. 2D), suggesting overall rigidity of the particles. The complex has a characteristic shape, with two lateral lobes corresponding to the two scaffolds, and a central lobe corresponding to the nanobody. The assembly of the complex from individual pieces is reminiscent of a Lego construction, so we propose to call it a "Legobody".

Case study I: KDEL Receptor (~23 kDa)

To test the utility of the Legobody method, a small membrane protein, the KDEL receptor was first chosen. This protein binds to the C-terminal KDEL sequence of luminal endoplasmic reticulum (ER) proteins that have escaped the ER, so that these proteins can be returned from the Golgi to the ER by vesicular transport [21]. The KDEL receptor has seven trans-membrane segments and a molecular weight of only ~23kDa. There are no domains outside membrane and no symmetry to facilitate particle alignment in EM images. The protein tends to aggregate during purification and on cryo-EM grids at the water-air interface of thin ice. All of these features pose challenges that are typical for the cryo-EM analysis of small membrane proteins, making KDEL receptor an ideal test object. A crystal structure of the KDEL receptor in complex with a tightly binding nanobody has been reported [22].

Figure 3A:
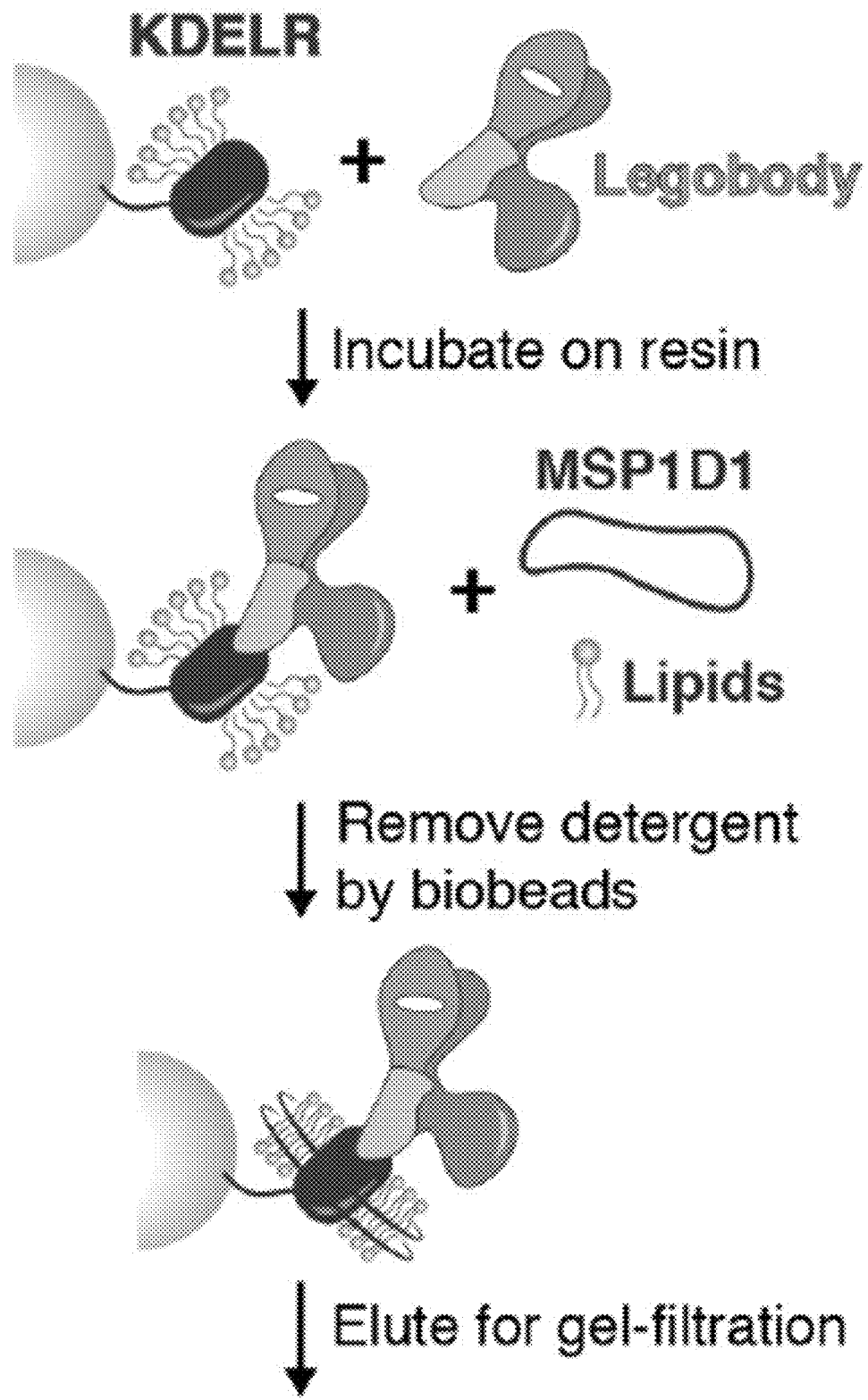
FIGS. 3A-3C depict the purification of a KDEL receptor (KDELR)/Legobody complex.
Figures 3B, 3C:
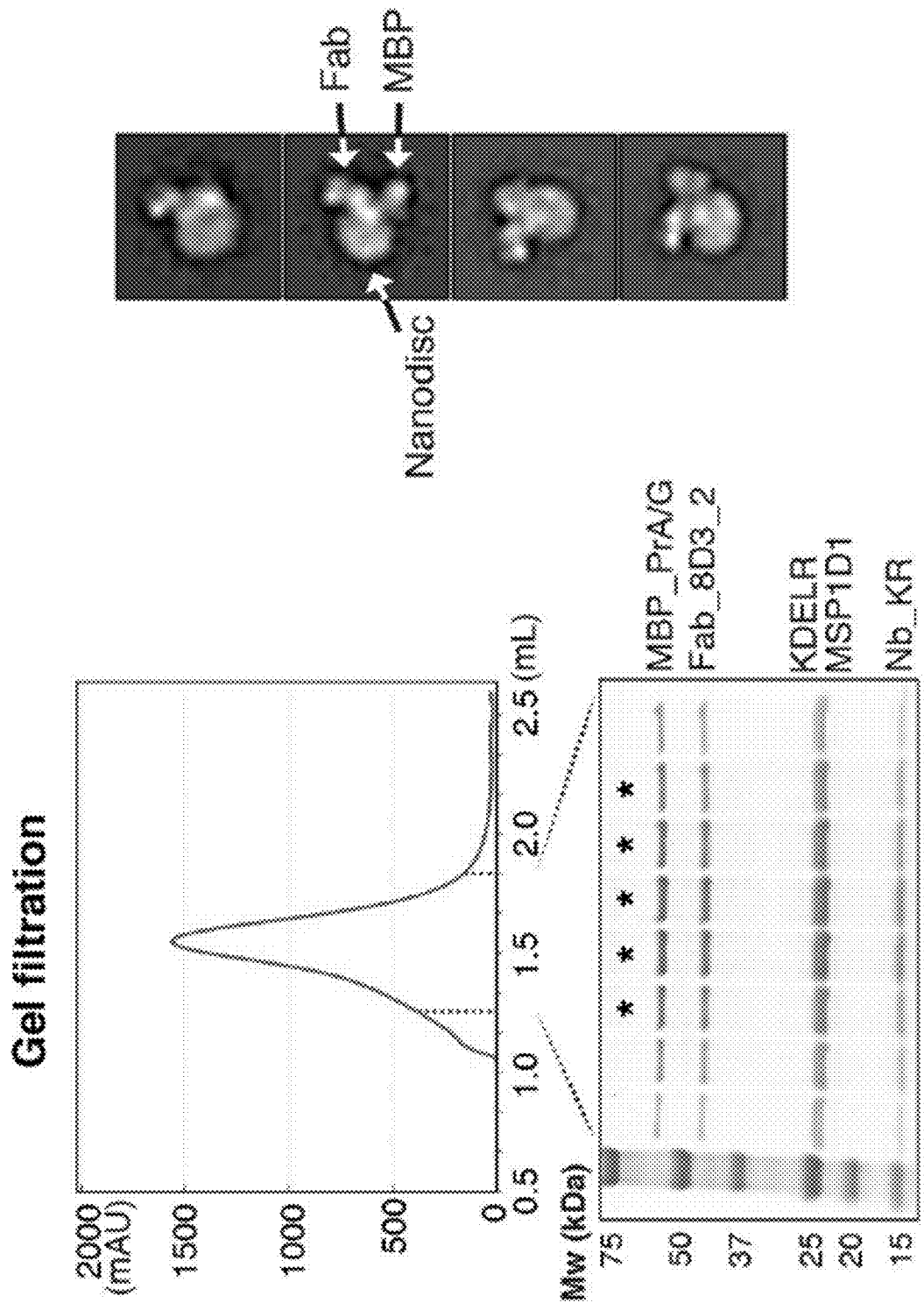

To generate a sample suitable for cryo-EM analysis, a protocol was devised that should be applicable to many other challenging membrane proteins (FIG. 3A). The solubilized KDEL receptor (KDELR), tagged with a streptavidin-binding peptide, was first immobilized on streptavidin beads. The detergent DMNG was employed, as it resulted in a more homogeneous sample than DDM used for the crystal structure [22]. The beads containing KDELR were then incubated with Legobody containing the reported nanobody against KDELR [22]. Finally, to reduce aggregation during purification, the complex was reconstituted into nanodisc on the beads. After elution from the beads with biotin, the complex of KDELR, Legobody, and nanodisc was further purified by size-exclusion chromatography (FIG. 3B). Negative-stain EM showed clear features for the Fab, MBP, and nanodisc (FIG. 3C).

Figure 4A:
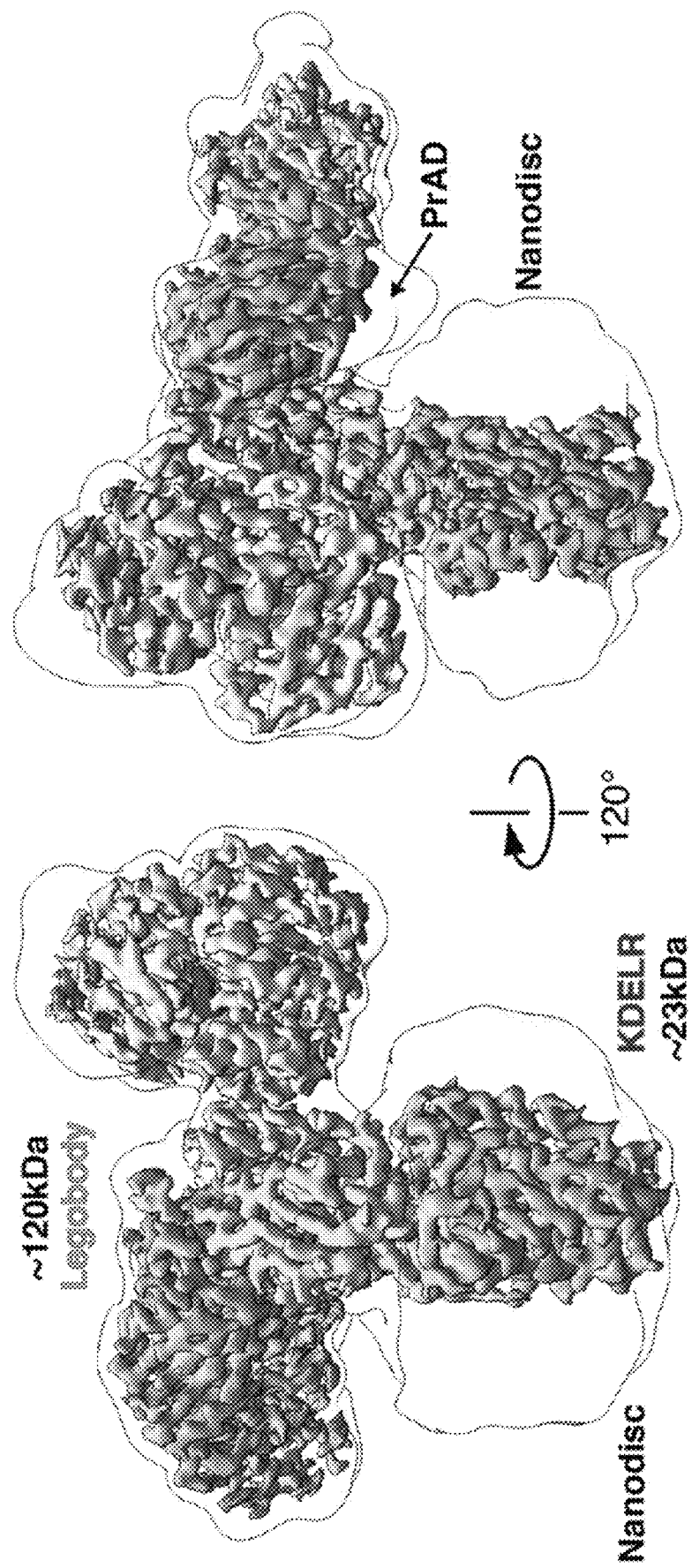
FIGS. 4A-4C depict the cryoEM structure of KDELR/Legobody complex.
Figure 4B:
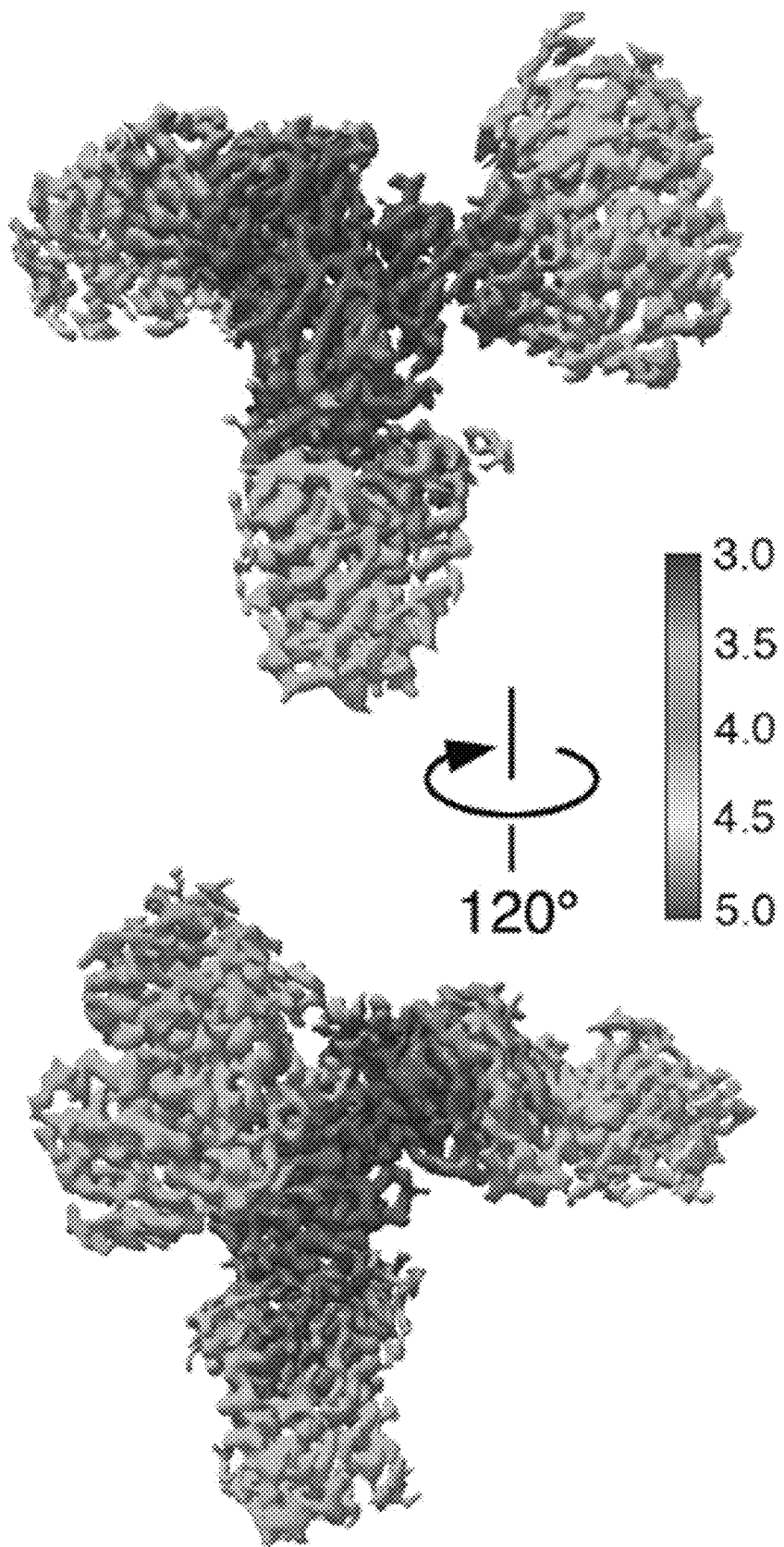
Figure 4C:
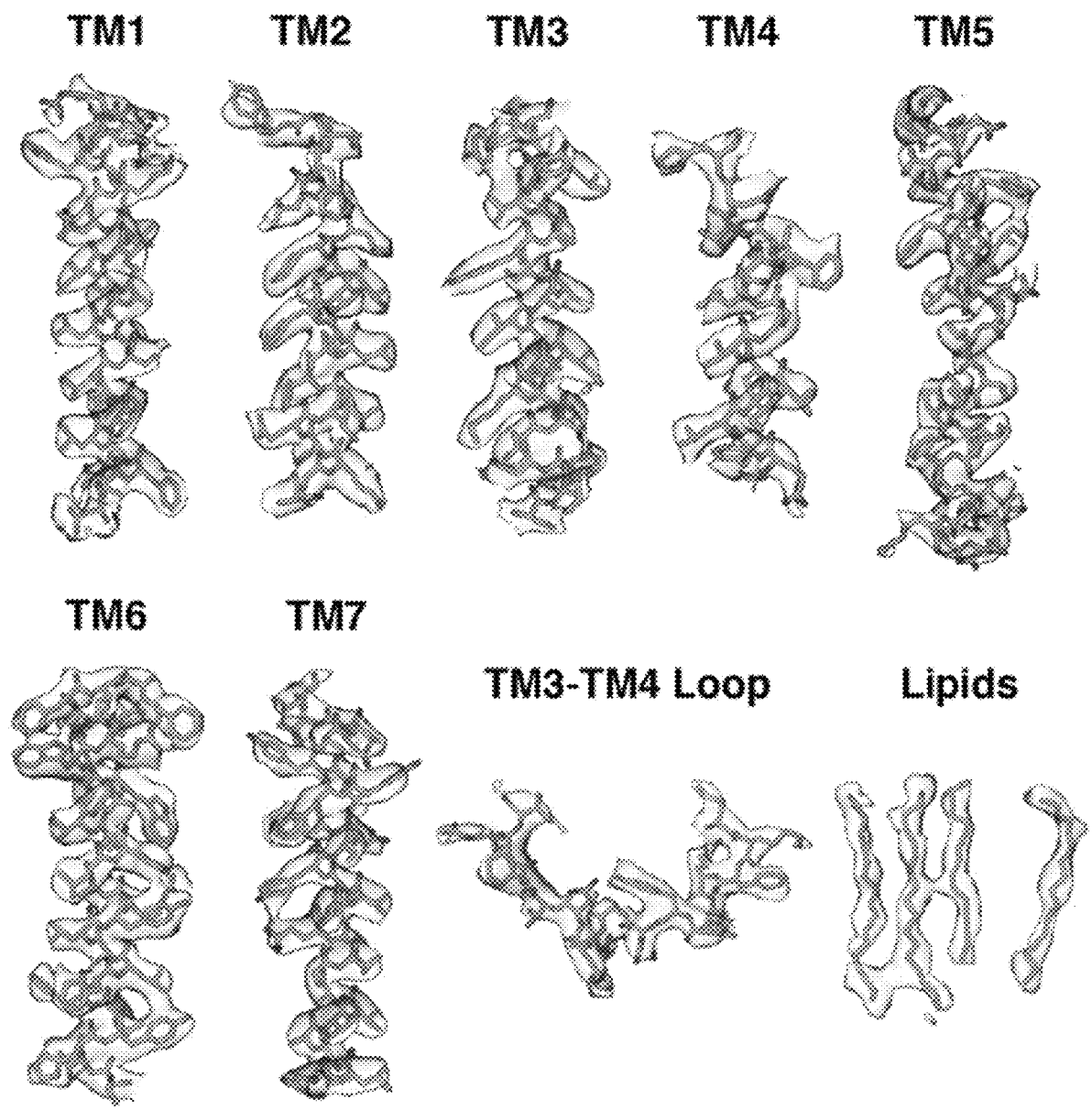
Figure 9A:
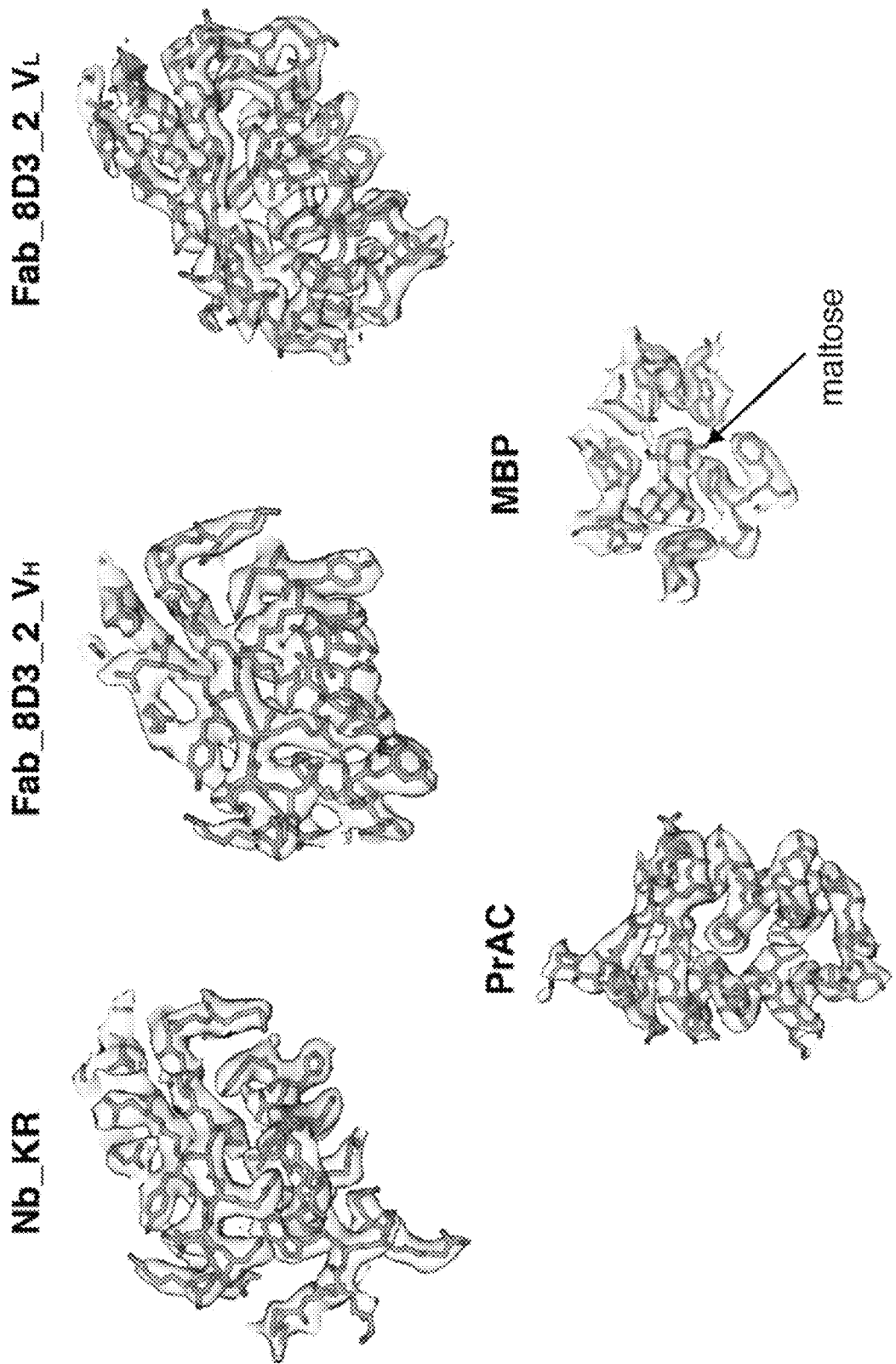
FIGS. 9A-9B depict fit of models for Legobody components and comparison of the cryoEM and crystal structures of the KDELR/nanobody complex.
Figure 9B:
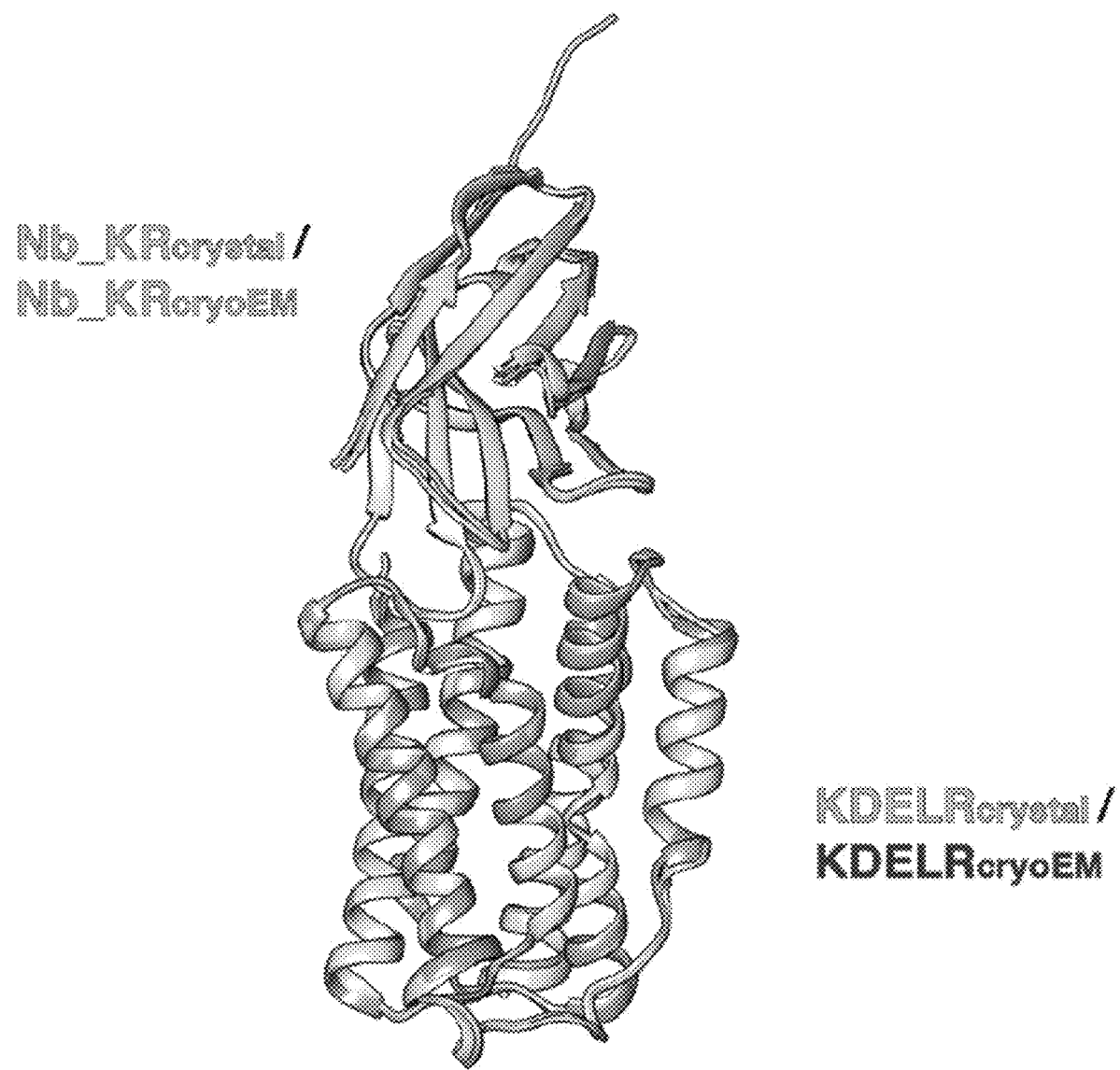
Figure 10A:
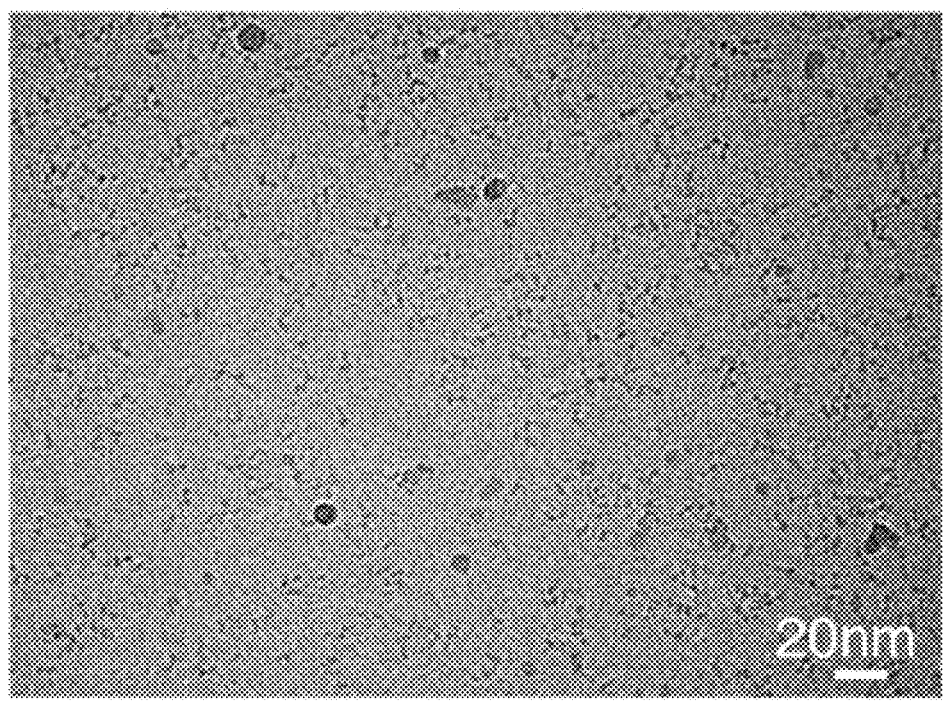
Figure 10B:
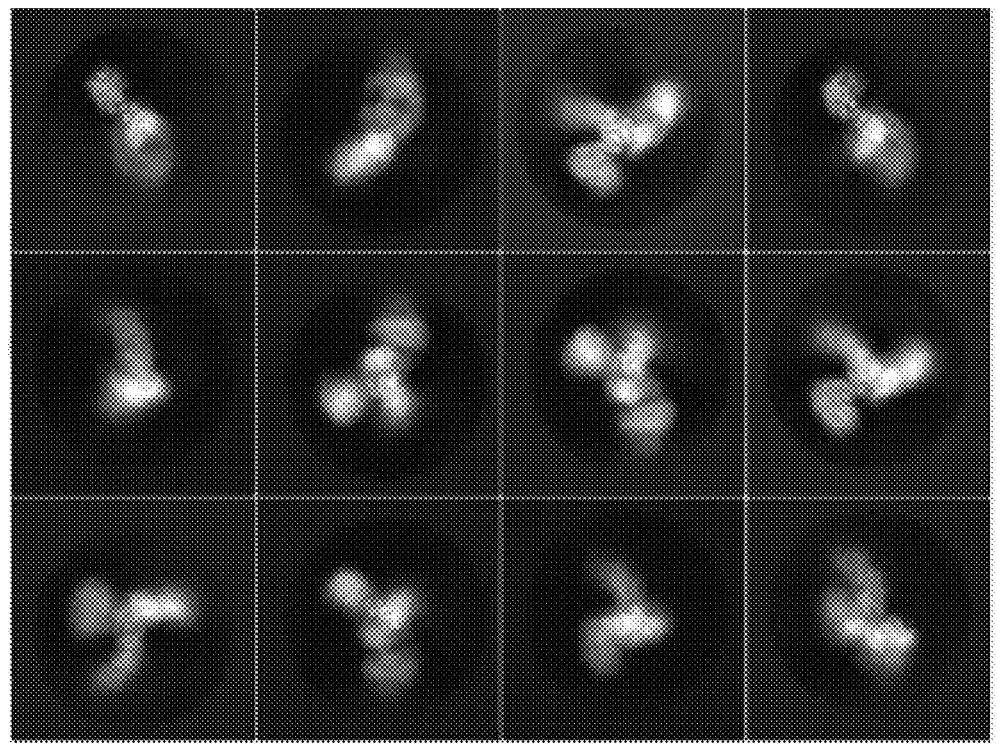
Figure 10C:
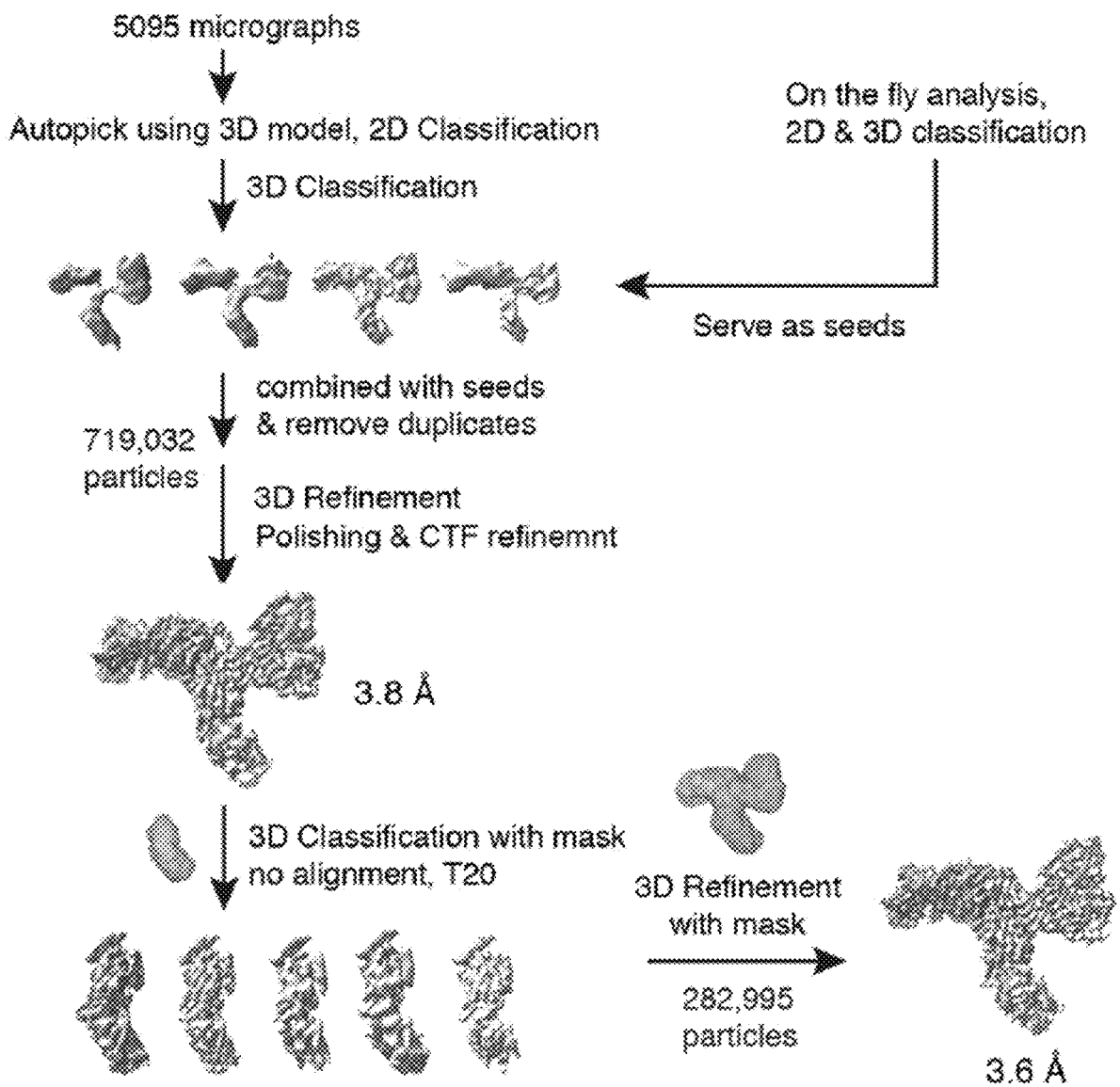
Figure 10F:
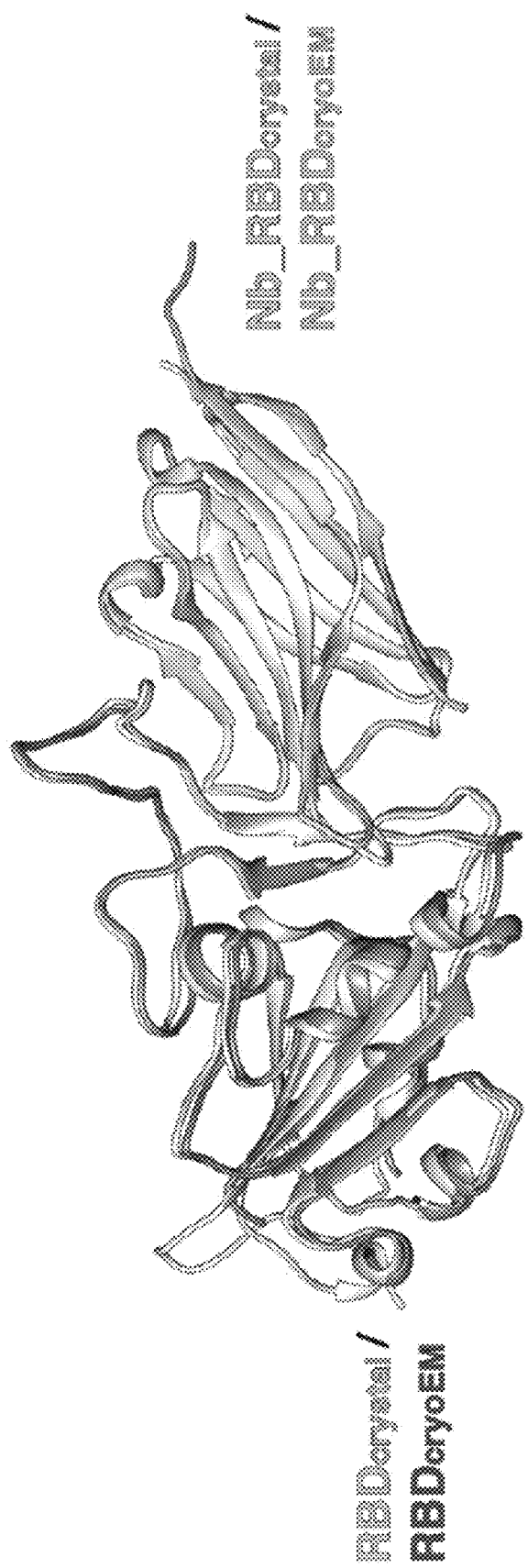

The complex was next analyzed by cryo-EM. When placed directly onto EM grids, the particles showed severe aggregation and strong preferred orientation, likely caused by denaturation of the molecules at the water-air interface. To alleviate this problem, surface lysine residues were modified with low molecular weight polyethylene glycol (PEG), a previously introduced method that makes the surface of proteins more hydrophilic and reduces their denaturation on the grids [23]. Although the particles were still not ideally distributed, the cryoEM analysis was straightforward, as the size and unique shape of the Legobody greatly facilitated particle picking and 2D and 3D classifications. The final 3D refinement of the selected particles resulted in a 3D reconstruction with an overall resolution of 3.2 Å (FIGS. 8A-8E; Table 3). With the exception of the relatively flexible PrAD domain, all parts of the Legobody and KDELR had well-resolved structural features, allowing even the visualization of the maltose molecule bound to MBP (FIG. 4A; FIG. 9A). The local resolution ranged from 3.0 to ~4.0 Å and showed that the interactions between the two scaffolds and the nanobody, as well as the connection between PrAC and MBP, are all rigid (FIG. 4B). Because the nanobody is tightly associated with the KDELR, and because the center of alignment of the Legobody is at the position of the nanobody, an excellent map was obtained for the KDELR (FIG. 4C). The local resolution of this part of the map ranged from 3.0 to ~3.5 Å and all amino acid side chains of the KDELR were clearly visible. In addition, several bound phospholipid molecules could easily be identified. The cryo-EM structure of the KDEL/nanobody complex is almost identical to that obtained by X-ray crystallography (FIG. 9B) [22]. Thus, the cryo-EM map would have allowed the de novo building of a model for the KDELR.

Case Study II: RBD of the SARS-CoV-2 Spike Protein (~22 kDa)

A second test protein for the Legobody method was the receptor-binding domain (RBD) of the SARS-CoV-2 spike protein. The RBD allows SARS-CoV-2 to bind to the ACE2 receptor and infect human cells [24]. This interaction is of great medical interest, particularly during the current pandemic, and therefore many RBD-neutralizing nanobodies have been generated [25]. The RBD has a molecular weight of only ~22 kDa and consists mainly of β-strands and extended polypeptide segments. Such structural elements are more difficult to trace in a map than α-helices.

Figure 5C:
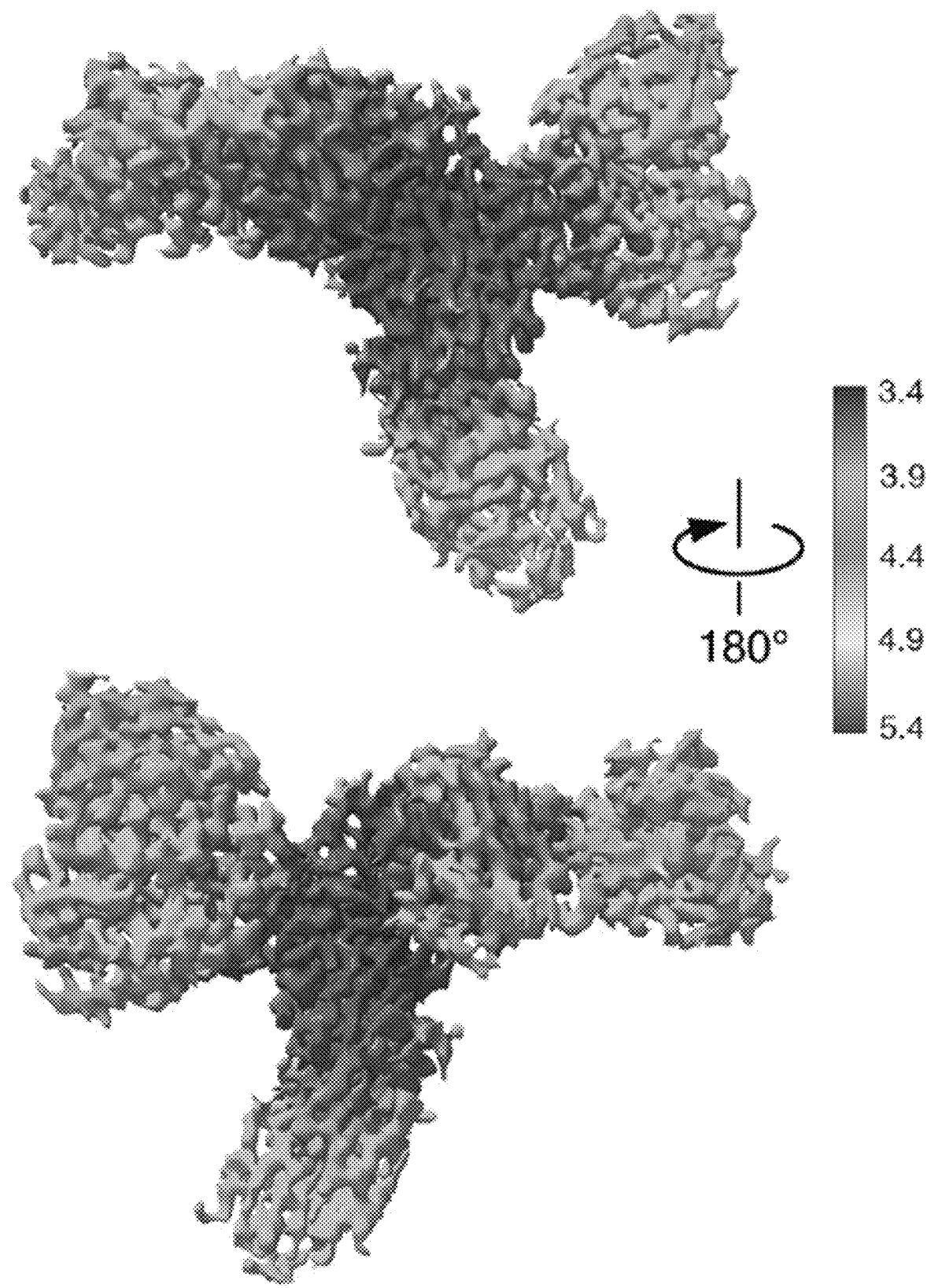
Figure 5D:
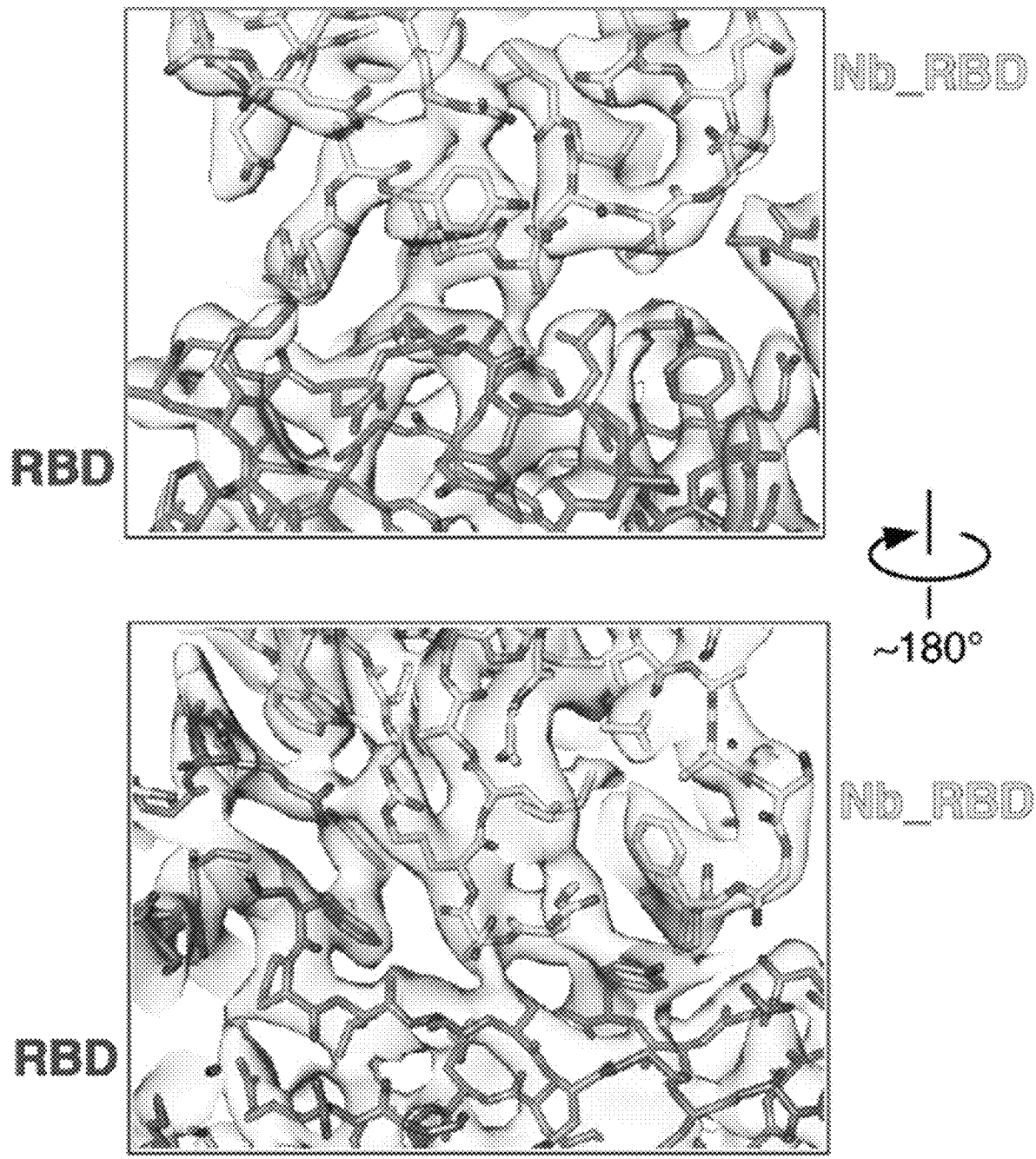

The RBD was expressed in HEK293 cells as a secreted protein and purified by Ni-NTA chromatography on the basis of an attached His-tag. The protein was mixed with the pre-assembled Legobody containing a reported nanobody against the RBD [26]. The complex was further purified by size-exclusion chromatography (FIG. 5A) and analyzed by cryo-EM. After 2D and 3D classifications, followed by 3D refinement, a map with an overall resolution of 3.6 Å was obtained (FIG. 5B; FIGS. 10A-10E; Table 3). The local resolution ranged from ~3.4 to ~4.4 Å and showed that the central regions of the scaffolds were rigid (FIG. 5C). The map for the RBD region showed good side-chain densities for amino acids at the interface with the nanobody (FIG. 5D). Some polypeptide loops distal to the binding interface were invisible (FIG. 5F), caused either by flexibility of the distal regions or by their denaturation at the water/air interface, i.e. issues unrelated to the Legobody method. The cryoEM structure of the RBD/nanobody complex is almost identical to that obtained by X-ray crystallography (FIG. 5F) [27].

Discussion

Described herein is a general method that allows cryo-EM structures to be determined for even the smallest proteins. This Legobody approach thus overcomes current limitations of cryo-EM analysis and greatly expands its use.

The new method can be applied to any target protein once a tightly binding nanobody is available. The nanobody is assembled into a Legobody by the binding of two scaffolds, a Fab fragment and a MBP molecule to which domain C of protein A domain has been grafted (MBP_PrAC). All interactions were designed to be rigid. In addition, Fab-interacting domains were fused to MBP_PrAC to further solidify the complex. The Legobody has a characteristic shape, consisting of two lateral lobes, formed by the two scaffolds, and a central lobe, contributed by the nanobody. The overall size (~120 kDa) and shape of the Legobody, and the center of alignment at the position of the nanobody, greatly facilitate all steps of cryo-EM analysis, from particle picking, classifications, to final refinement. Demonstrated herein is the utility of the Legobody method with two examples of small target proteins (KDELR (23 kDa) and the RBD (22 kDa) of the SARS-CoV-2 spike protein).

The membrane protein KDELR poses a particular challenge for cryoEM analysis, as it is small, very hydrophobic, and prone to aggregation. To determine its structure, the inventors not only used the Legobody approach, but also employed two other tricks, which likely are applicable to other challenging membrane proteins. First, a purification strategy was introduced, in which the KDELR/Legobody complex was incorporated into nanodisc while bound to beads (FIG. 3A). This strategy reduces aggregation of the receptor and increases its stability in solution. Second, before applying the sample to EM grids, surface lysines were modified with low-molecular weight PEG. This protocol has been used for other proteins [23,28,29], and it often dramatically reduces particle aggregation and preferred particle orientation. Using standard cryoEM data analysis, a high-quality map was obtained for the KDELR, with density visible for all amino acid side chains. The structure is virtually identical to that determined previously by X-ray crystallography, but the cryo-EM map would have allowed straight-forward de novo model building.

The KDELR is representative of a large group of membrane proteins, which are of small size and pose similar challenges for cryoEM analysis. Examples include G-protein coupled receptors, solute carrier transporters, and membrane-embedded enzymes, many of which are of great interest for drug development. The Legobody method now makes all these proteins accessible to cryoEM analysis.

The RBD of the SARS-CoV-2 spike protein also presents a challenge for cryo-EM analysis, as it is small and consists mainly of β-strands and extended polypeptide segments, which are more difficult to model into a map than α-helices. The map obtained with the Legobody approach was of good quality, especially at the RBD/nanobody interface, with side-chain density for all interacting amino acids. Because this interface is the region of medical interest, these results show that cryo-EM can be used to optimize RBD-neutralizing nanobodies, which may be important for the quick response to future virus pandemics. By comparison with X-ray crystallography, cryo-EM requires only small amounts of protein and can be performed in a significantly shorter time period.

Figures 11A, 11B:
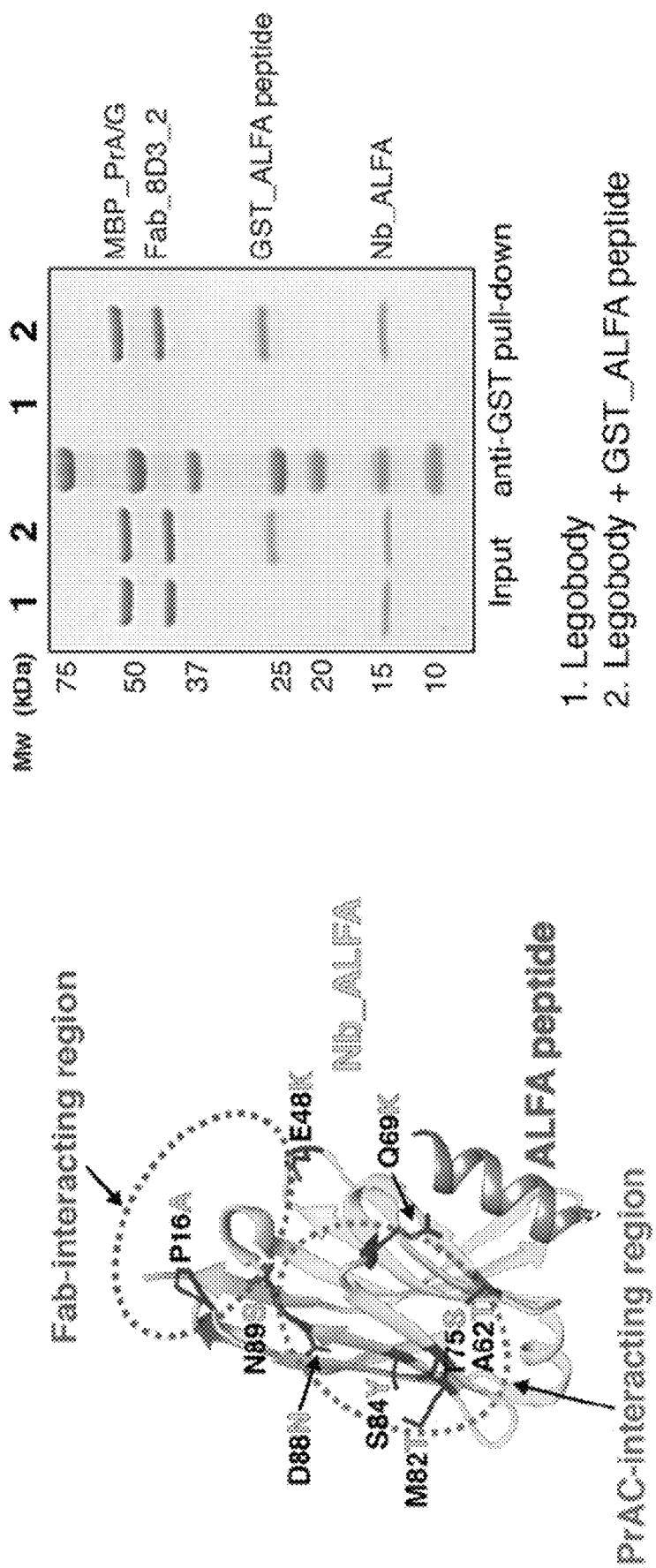
FIGS. 11A-11B depict the generation of a Legobody-compatible ALFAtag nanobody.

The Legobody method was developed using nanobodies that have a common framework similar to that used in two in vitro libraries [10,11]. However, the method can be applied to nanobodies that originally have a different framework, such as those often generated in alpaca. For example, a nanobody directed against the ALFAtag peptide, which is frequently used to purify or visualize fusion proteins [30], differs significantly in its framework sequence (sequence identity ~75%) and would therefore not allow interactions with the scaffolds. However, after mutating nine amino acid residues in the Fab- and PrAC-interacting regions, the resulting Nb_ALFA could be assembled into a Legobody (FIGS. 11A-11B). These mutations did not affect antigen binding, as GST-tagged ALFA peptide was able to pull-down the pre-assembled Legobody containing the modified nanobody (FIG. 11B). We therefore believe that all nanobodies can be used, regardless of whether they are obtained from in vitro libraries or from animal species.

A possible limitation of the Legobody method could arise from steric clashes between the scaffolds and targets. To test whether this is a serious problem, crystal structures of complexes of nanobody with small monomeric target proteins were aligned with the Legobody structure on the basis of the nanobody. Observed steric clashes are listed in FIGS. 12A-12E. For soluble proteins, only three examples were found in which the Fab or MBP_PrAC would clash with the target. For membrane proteins embedded into detergent micelles, nanodiscs, or lipid cubic phase, clashes would sometimes be caused by the PrAD domain or the MBP_PrAC scaffold. No clashes were observed for the Fab, but the number of available structures is too small to exclude their existence in other cases. Clashes with the PrAD domain can be avoided by deleting this domain and connecting MBP_PrAC directly to PrG via a suitable linker. In fact, this domain bound only weakly to its intended binding site on the Fab and should therefore be dispensable even in the original design. Clashes with MBP_PrAC or Fab can be avoided by using only one of the scaffolds. If only the MBP_PrAC scaffold can be used, it is recommended to fuse the nanobody to the N-terminus of MBP_PrAC via a flexible linker, as the fusion would increase the solubility of the nanobody and the stability of the final Legobody complex. Tests for the compatibility of the scaffolds with the nanobody/target interaction are straightforward (similar to the experiments in FIG. 11B). Such pull-down experiments could also be used to screen right-away for nanobodies that are compatible with both scaffolds, avoiding nanobodies that would cause steric clashes.

The Legobody used in this study could easily be modified to further increase its molecular mass, stability, and rigidity. For example, the three-helix bundle of PrAC could be engineered to increase its binding affinity or it could be grafted onto other large proteins. In addition, fusions could be generated with protein L (ref. [31]) or a modified version of protein M (ref. [32]), which bind to the Fab at different sites than the fusion partners used in the current Legobody design. It is contemplated herein that the current Legobodies and their possible variations will make cryoEM structure determination of small proteins a routine method.

Methods

Purification of Nanobodies

Genes for His-tagged or Strep II-tagged nanobodies were cloned into the pET 26b vector (Novagen). The expression and purification of all His-tagged nanobodies have been described previously [11]. For immunization of mice, the His-tag was removed by treating purified nanobody Nb_0 with carboxypeptidase A (Sigma) and B (Roche) overnight at 4° C. The treated nanobodies were passed through a Ni-NTA column and the flow-through fraction was further purified by size-exclusion chromatography on a S75 increase column in 25 mM HEPES pH 7.4, 150 mM NaCl, 5% glycerol. Strep II-tagged nanobody Nb_MBP was purified using streptactin resin (IBA). The beads were washed with 25 mM HEPES pH 7.4, 150 mM NaCl, and the protein was eluted in 25 mM HEPES pH 7.4, 150 mM NaCl, 2 mM desthiobiotin. For screening of hybridoma cell clones, a complex of Strep II-tagged nanobody Nb_MBP and MBP was used. The eluted Strep II-tagged Nb_MBP protein was mixed with separately purified MBP protein at a molar ratio of 3:1. The mixture was subjected to size-exclusion chromatography on a S200 increase column in 25 mM HEPES pH 7.4, 150 mM NaCl, 5% glycerol. The peak fractions of the complex were stored for future use.

Generating Antibodies Against Nanobodies

Monoclonal antibodies were generated by immunizing mice with purified tagless nanobody Nb_0 at the VGTI Monoclonal Core. Hybridoma clones were screened under non-denaturing condition using the purified complex consisting of Strep II-tagged Nb_MBP and MBP. Antibodies secreted by clone 8D3 bound both Nb_0 and the Nb_MBP/MBP complex with high affinity. The 8D3 clone was expanded for further characterization. The sequences of the variable light ($V_L$) and heavy ($V_H$) chain regions of the monoclonal antibody were determined by Syd Labs.

Recombinant Expression of Fabs

To increase the yield of recombinant expression of the Fabs in HEK293 cells, the constant regions of the light and heavy chains were replaced by sequences from human Fabs (for sequences, see below). The resulting chimera genes for the light chain and the His-tagged heavy chain of the Fabs were separately cloned into the pCAGEN vector (a gift from Connie Cepko (Addgene plasmid #11160)) [33]. For co-transfection of a 1L HEK293$^{freestyle}$ (Thermo Fisher) culture, 0.5 mg of both plasmids were incubated with 3 mg of Linear PEI 25K (Polysciences) in 100 ml of Opti-MEM (Thermo Fisher) medium at room temperature for 30 mins. The mixture was then added drop-wise into the medium containing HEK293$^{freestyle}$ cells to reach a final cell density of 2 million/ml. The cells were cultured at 37° C. for 12~16 hrs before addition of 10 mM sodium butyrate to boost expression. Medium containing secreted Fabs was harvested 48~62 hrs post-transfection. Purification of the Fabs was carried out as follows. Harvested medium free of cells was supplemented with 50 mM TRIS pH 8.0, 200 mM NaCl, 20 mM imidazole and 1 μM NiSO$_4$. His-tagged Fabs were purified by Ni-NTA chromatography. The beads were washed extensively with 25 mM HEPES pH 7.4, 200 mM NaCl, 20 mM imidazole. Fabs were eluted in 25 mM HEPES pH 7.4, 200 mM NaCl, 300 mM imidazole. Eluted Fabs were concentrated and buffer-exchanged into 25 mM HEPES pH 7.4, 150 mM NaCl, 5% glycerol. Aliquots were snap-frozen for future use.

Based on reports that Fabs interact preferentially with domain D of protein A [15] and on a crystal structure of a complex of Fab and this domain (PDB code 1DEE), several mutations were introduced in the variable region of the heavy chain of the partially humanized Fab_8D3 (see above), resulting in Fab_8D3_2 (mutations: G16K, R18L, K19R, I58K, F80Y, T84N; the sequence is shown below). Fab_8D3_2 was purified in the same way as the original Fab_8D3.

Determination of a Crystal Structure of the Nb_0/Fab_8D3 Complex

Purified His-tagged Fab_8D3 was mixed with purified His-tagged Nb_0 nanobody at a molar ratio of 1:3. The mixture was treated with carboxypeptidase A (Sigma) overnight at 4° C. to remove the His-tags. The sample was subjected to size-exclusion chromatography on a S200 increase column in 25 mM HEPES pH 7.4, 150 mM NaCl.

The peak fractions of the complex were pooled and concentrated to 10 mg/ml and used to set up crystal screens.

Purified Nb_0/Fab_8D3 complex (0.2 µl of a 10 mg/ml solution) was mixed with 0.2 µl of mother liquor containing 0.2M ammonium formate, 20-22% w/v PEG 3,350 using a Mosquito robot (TTP Labtech). Crystals were grown at 4° C. with the hanging drop method over a reservoir of 100 µl mother liquor and reached full size in about two weeks. Crystals were cryo-protected before harvest in a solution containing mother liquor supplemented with 25 mM HEPES 7.5 and 18% ethylene glycol. X-ray diffraction data were collected on the 24-ID-E beamline at the Advanced Photon Source (APS). Initial phases were obtained by Molecular Replacement using crystal structures of Fabs and nanobodies with similar amino acid sequences as search models. In both search models, the CDR regions were removed.

Purification of MBP Fusions

The sequences of all MBP fusion proteins are given below. Based on crystal structures and modeling, we predicted residue Ala405 of MBP_PrA/G-His6 to be close to the Fab and therefore mutated it to histidine to boost the interaction.

All variants of MBP fusion proteins were purified as follows. The genes were cloned into the pET28b vector (Novagen) with either an N- or C-terminal His6 tag. The expression was induced by addition of 1 mM IPTG for 4 hrs at 37° C. The cells were lysed by sonication in 25 mM HEPES pH 7.4, 400 mM NaCl, 20 mM imidazole. The proteins were purified by Ni-NTA chromatography using lysis buffer as washing buffer. After elution with imidazole, proteins were subjected to size-exclusion chromatography on a S200 increase column in 25 mM HEPES pH 7.4, 150 mM NaCl, 5% glycerol. The peak fractions were stored for future use.

Purification of GST Fused ALFA Peptide

GST fused ALFA peptide was purified as follows. The gene for the ALFA peptide was cloned into the pGEX6p1 vector (Cytiva). The expression was induced by addition of 1 mM IPTG for 5 hrs at 30° C. The cells were lysed by sonication in 25 mM HEPES pH 7.4, 400 mM NaCl. The proteins were purified by GST resins using lysis buffer as washing buffer. After elution with reduced glutathione (GSH), proteins were subjected to size-exclusion chromatography on a S200 increase column in 25 mM HEPES pH 7.4, 150 mM NaCl, 5% glycerol. The peak fractions were stored for future use.

Purification of Legobodies

Legobodies were assembled by first incubating purified MBP_PrA/G with Fab_8D3_2 at a molar ratio of 1:1.1 in 25 mM HEPES pH 7.4, 150 mM NaCl. Then, the mixture was incubated with a chosen nanobody added at a 3-fold molar excess over MBP_PrA/G. The sample was applied to an amylose resin and the complex was eluted with 25 mM HEPES pH 7.4, 150 mM NaCl, 20 mM maltose. The Legobodies were further purified by size-exclusion chromatography on a S200 increase column in 25 mM HEPES pH 7.4, 150 mM NaCl, 5% glycerol, 2 mM maltose. The peak fractions of the complexes were concentrated and stored for future use.

Purification of a Complex of KDEL-Receptor (KDELR) and Legobody

The codon-optimized gene for the full-length KDELR with a SBP tag at its C-terminus was cloned into the pRS425-Gal1 vector (ATCC® 87331)[34] The expression of the receptor and preparations of the membrane fractions were carried out as previously described[23]. Membranes from 15 g of INVScl (Invitrogen) cells expressing the receptor were solubilized in 30 ml of 25 mM HEPES pH 7.4, 400 mM NaCl, 1% DMNG for 1hr. After removing insoluble material by ultra-centrifugation, the lysate was incubated with 250 µl streptavidin resin (Thermo Fisher) for 1.5 hr. The beads were collected and an excess of purified Legobody was added to the bound KDEL receptor to promote complex formation on the resin. After 1 hr of incubation, the resin was washed with 8 column volumes of 25 mM HEPES pH 7.4, 150 mM NaCl, 2 mM maltose, 0.02% DMNG. Nanodiscs were assembled on the resin by adding 1.25 mM lipids (POPC/DOPE at a 4:1 ratio in DDM) and 25 µM nanodisc-scaffolding protein MSP1D1 in 700 µl of washing buffer. After 30 mins of incubation, the detergents were removed by the addition of two aliquots of 40 mg of Biobeads and overnight incubation. The next day, the streptavidin resins were separated from Biobeads, taking advantage of their different rates of sedimentation by gravity. The streptavidin resins were washed by 25 mM HEPES pH 7.4, 150 mM NaCl, 2 mM maltose and bound material was eluted with biotin. The KDEL receptor/Legobody complex in nanodisc was then purified by size-exclusion chromatography on a S200 increase column in 25 mM HEPES pH 7.4, 150 mM NaCl, 2 mM maltose. The peak fractions of the complex were concentrated, snap-frozen and stored for cryo-EM analysis.

Purification of a Complex of the SARS-CoV-2 Spike RBD Domain and Legobody

The codon-optimized gene for the RBD domain (residues 334-526) of SARS-CoV-2 spike protein with an N-terminal Flag tag and a C-terminal His8 tag was cloned into the pCAGEN vector. The RBD was expressed and purified in the same way as the Fabs. After elution from Ni-NTA beads, the protein was subjected to size-exclusion chromatography on a S75 increase column in 25 mM HEPES pH 7.4, 150 mM NaCl. Peak fractions were mixed with Legobody at a molar ratio of 3:1. The mixture was subjected to size-exclusion chromatography on a S200 increase column in 25 mM HEPES pH 7.4, 150 mM NaCl, 2 mM maltose. The peak fractions of the complex were concentrated, snap-frozen, and stored for cryo-EM analysis.

Cryo-EM Sample Preparation and Data Acquisition

The KDELR/Legobody complex at 0.8 mg/ml was PEGylated by incubation with MS(PEG)12 methyl-PEG-NHS-ester (Thermo Fisher) at a 1:40 molar ratio for 2 hrs on ice to reduce preferred particle orientation on the grids. The chosen ratio allows a maximum of ⅓ of the total lysines to be modified, which minimizes effects of PEG modification on the stability of the complex. The PEGylated sample was then applied to a glow-discharged quantifoil gold grid (1.2/1.3, 400 mesh). The grids were blotted for 6~7 s at 100% humidity and plunge-frozen in liquid ethane using a Vitrobot Mark IV instrument (Thermo Fisher). The RBD/Legobody complex at 2.5 mg/ml were incubated with MS(PEG)12 methyl-PEG-NHS-ester (Thermo Fisher) at a 1:25~28 molar ratio for 2 hrs on ice. Right before plunge freezing, the PEGylated samples were diluted, using the gel-filtration buffers supplemented with detergent IGEPAL® CA-630 (Sigma), so that the final protein and detergent concentrations were 1.2 mg/ml and 0.005%, respectively. The grids were frozen in the same way as described for the KDELR/Legobody sample.

Cryo-EM data for all samples were collected on a Titan Krios electron microscope (FEI) operated at 300 kV and equipped with a K3 direct electron detector (Gatan) at Harvard Cryo-EM Center for Structural Biology. A Gatan Imaging filter with a slit width of 25 eV was used to remove inelastically scattered electrons. All cryo-EM movies were recorded in counting-mode using SerialEM. For the KDELR/Legobody sample, the nominal magnification of 81,000× corresponds to a calibrated pixel size of 1.06 Å on the specimen. The dose rate was 23.38 electrons/Å$^2$/s. The total exposure time was 2.2 s, resulting a total dose of 51.44 electrons/Å$^2$, fractionated into 50 frames (44 ms per frame). For the RBD/Legobody sample, the calibrated pixel size was 1.06 Å. The dose rate was 23.3 electrons/Å$^2$/s. The total exposure time was 2.164 s, resulting a total dose of 50.42 electrons/Å$^2$, fractionated into 50 frames (44 ms per frame). The defocus range for both samples was between −1.0 and −2.6 μm.

Cryo-EM Image Processing

For the KDELR/Legobody complex, dose-fractionated movies were subjected to motion correction using the program MotionCor2 [35] with dose-weighting. The program CtfFind4 [36] was used to estimate defocus values of the summed images from all movie frames. During data collection, the initially picked particles by YOLO [37] were subjected to 2D and 3D classifications in Relion 3.1 [38]. There was only one class with clear protein secondary structure features. Particles of this class were selected for 3D refinement, resulting a reconstruction at 3.8 Å overall nominal resolution. This initial 3D reconstruction was used as a template to perform autopick in Relion 3.1 on the entire dataset. After 2D classifications, re-picked particles were "seeded" with particles used in the previous 3D refinement for 3D classification. After 3D classification, only the class showing clear protein secondary structure features of the whole complex was selected. After removing duplicates, the particles were subjected to 3D refinement, followed by polishing, CTF refinement, and another round of 3D refinement. Local 3D classification without image alignment (T20) was performed using a mask including only the nanobody and KDELR. Particles were finally selected for 3D refinement using a mask excluding the nanodisc and the more flexible D domain of protein A.

For the RBD/Legobody complex, data analysis was performed in a similar way. Local resolution calculation and map sharpening were both performed in Relion 3.1. All reported resolutions are based on gold-standard refinement procedures and the FSC=0.143 criterion.

Model Building

All model building was done in Coot. For the crystal structure of Nb_0/Fab_8D3, an initial model was obtained by molecular replacement. For the cryoEM structures, initial models were based on the crystal structure of the Nb_0/Fab_8D3 complex, modified to account for the mutations in Fab_8D3_2, and the crystal structures of the KDEL receptor (6I6J), RBD (7KGJ), the manually grafted MBP_PrAC (1ANF and 4PND), the D domain of Protein A (1DEE), and protein G (1IGC). These structures were docked into the maps and manually modified based on the cryo-EM density. All models were then refined using Phenix [39].

REFERENCES

1. Fernandez-Leiro, R. & Scheres, S. H. W. Unravelling biological macromolecules with cryo-electron microscopy. *Nature* 537, 339-346 (2016).
2. Fan, X. et al. Single particle cryo-EM reconstruction of 52 kDa streptavidin at 3.2 Angstrom resolution. *Nature communications* 10, 2386-11 (2019).
3. Han, Y. et al. High-yield monolayer graphene grids for near-atomic resolution cryoelectron microscopy. *Proceedings of the National Academy of Sciences of the United States of America* 117, 1009-1014 (2020).
4. Tsutsumi, N. et al. Structure of human Frizzled5 by fiducial-assisted cryo-EM supports a heterodimeric mechanism of canonical Wnt signaling. *eLife* 9, (2020).
5. Liu, Y., Huynh, D. T. & Yeates, T. O. A 3.8 Å resolution cryo-EM structure of a small protein bound to an imaging scaffold. *Nature communications* 10, 1864-7 (2019).
6. Yao, Q., Weaver, S. J., Mock, J.-Y. & Jensen, G. J. Fusion of DARPin to Aldolase Enables Visualization of Small Protein by Cryo-EM. *Structure* 27, 1148-1155.e3 (2019).
7. Lee, Y. et al. Cryo-EM structure of the human L-type amino acid transporter 1 in complex with glycoprotein CD98hc. *Nature structural & molecular biology* 26, 510-517 (2019).
8. Bloch, J. S. et al. Structure and mechanism of the ER-based glucosyltransferase ALG6. *Nature* 579, 443-447 (2020).
9. Kim, J. et al. Structure and drug resistance of the Plasmodium falciparum transporter PfCRT. *Nature* 576, 315-320 (2019).
10. Zimmermann, I. et al. Synthetic single domain antibodies for the conformational trapping of membrane proteins. *eLife* 7, (2018).
11. McMahon, C. et al. Yeast surface display platform for rapid discovery of conformationally selective nanobodies. *Nature structural & molecular biology* 25, 289-296 (2018).
12. Uchański, T. et al. Megabodies expand the nanobody toolkit for protein structure determination by single-particle cryo-EM. *Nat. Methods* 18, 60-68 (2021).
13. Henderson, R. The potential and limitations of neutrons, electrons and X-rays for atomic resolution microscopy of unstained biological molecules. *Quarterly Reviews of Biophysics* 28, 171-193 (1995).
14. Frenken, L. G. et al. Isolation of antigen specific llama VHH antibody fragments and their high level secretion by Saccharomyces cerevisiae. *J Biotechnol* 78, 11-21 (2000).
15. Jansson, B., Uhlén, M. & Nygren, P. A. All individual domains of staphylococcal protein A show Fab binding. *FEMS Immunol Med Microbiol* 20, 69-78 (1998).
16. Fridy, P. C., Thompson, M. K., Ketaren, N. E. & Rout, M. P. Engineered high-affinity nanobodies recognizing staphylococcal Protein A and suitable for native isolation of protein complexes. *Analytical Biochemistry* 477, 92-94 (2015).
17. Waugh, D. S. Crystal structures of MBP fusion proteins. Protein science: a publication of the *Protein Society* 25, 559-571 (2016).
18. Youn, S.-J. et al. Construction of novel repeat proteins with rigid and predictable structures using a shared helix method. *Sci Rep* 7, 2595-11 (2017).
19. Graille, M. et al. Crystal structure of a *Staphylococcus aureus* protein A domain complexed with the Fab fragment of a human IgM antibody: structural basis for recognition of B-cell receptors and superantigen activity. *Proceedings of the National Academy of Sciences of the United States of America* 97, 5399-5404 (2000).
20. Derrick, J. P. & Wigley, D. B. The third IgG-binding domain from streptococcal protein G. An analysis by X-ray crystallography of the structure alone and in a complex with Fab. *Journal of molecular biology* 243, 906-918 (1994).
21. Semenza, J. C., Hardwick, K. G., Dean, N. & Pelham, H. R. ERD2, a yeast gene required for the receptor-mediated retrieval of luminal ER proteins from the secretory pathway. *Cell* 61, 1349-1357 (1990).

22. Bräuer, P. et al. Structural basis for pH-dependent retrieval of ER proteins from the Golgi by the KDEL receptor. *Science* 363, 1103-1107 (2019).
23. Wu, X. et al. Structural basis of ER-associated protein degradation mediated by the Hrd1 ubiquitin ligase complex. *Science* 368, (2020).
24. Hoffmann, M. et al. SARS-CoV-2 Cell Entry Depends on ACE2 and TMPRSS2 and Is Blocked by a Clinically Proven Protease Inhibitor. *Cell* 181, 271-280.e8 (2020).
25. Czajka, T. F., Vance, D. J. & Mantis, N. J. Slaying SARS-CoV-2 One (Single-domain) Antibody at a Time. *Trends Microbiol* 29, 195-203 (2021).
26. Walter, J. D. et al. Synthetic nanobodies targeting the SARS-CoV-2 receptor-binding domain. *bioRxiv* 2020.04.16.045419 (2020). doi:10.1101/2020.04.16.045419
27. Ahmad, J., Jiang, J., Boyd, L. F., Natarajan, K. & Margulies, D. H. Synthetic nanobody-SARS-CoV-2 receptor-binding domain structures identify distinct epitopes. *bioRxiv* 2021.01.27.428466 (2021). doi: 10.1101/2021.01.27.428466
28. Wu, X., Cabanos, C. & Rapoport, T. A. Structure of the post-translational protein translocation machinery of the ER membrane. *Nature* 566, 136-139 (2019).
29. Chung, J. et al. LDAF1 and Seipin Form a Lipid Droplet Assembly Complex. *Dev Cell* 51, 551-563.e7 (2019).
30. Götzke, H. et al. The ALFA-tag is a highly versatile tool for nanobody-based bioscience applications. *Nature communications* 10, 4403-12 (2019).
31. Graille, M. et al. Complex between Peptostreptococcus magnus protein L and a human antibody reveals structural convergence in the interaction modes of Fab binding proteins. *Structure* 9, 679-687 (2001).
32. Grover, R. K. et al. A structurally distinct human mycoplasma protein that generically blocks antigen-antibody union. *Science* 343, 656-661 (2014).
33. Matsuda, T. & Cepko, C. L. Electroporation and RNA interference in the rodent retina in vivo and in vitro. *Proceedings of the National Academy of Sciences of the United States of America* 101, 16-22 (2004).
34. Mumberg, D., Muller, R. & Funk, M. Regulatable promoters of Saccharomyces cerevisiae: comparison of transcriptional activity and their use for heterologous expression. *Nucleic Acids Research* 22, 5767-5768 (1994).
35. Zheng, S. Q. et al. MotionCor2: anisotropic correction of beam-induced motion for improved cryo-electron microscopy. *Nat. Methods* 14, 331-332 (2017).
36. Rohou, A. & Grigorieff, N. CTFFIND4: Fast and accurate defocus estimation from electron micrographs. *Journal of structural biology* 192, 216-221 (2015).
37. Wagner, T. et al. SPHIRE-crYOLO is a fast and accurate fully automated particle picker for cryo-EM. *Commun Biol* 2, 218-13 (2019).
38. Zivanov, J. et al. New tools for automated high-resolution cryo-EM structure determination in RELION-3. *eLife* 7, (2018).
39. Liebschner, D. et al. Macromolecular structure determination using X-rays, neutrons and electrons: recent developments in Phenix. *Acta Crystallogr D Struct Biol* 75, 861-877 (2019).

TABLE 1

| Name | Sequence | SEQ ID NO |
|---|---|---|
| Fab_8D3_H-H6 | MDWTWRVFCLLAVAPGAHSDVQLVESGGGLVQPGGSRKLSCAASGFTFS NFGMHWVRQAPEMGLEWVAYISSGSTTIYYGDTVKGRFTISRDNPKNTLF LQMTSLRSEDTAMYYCARRPLYDGDYGYPMDYWGQGTSVTVSSASTKGP SVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCGSHHH HHH | 1 |
| Fab_8D3_H-H6 CDR1 | NFGMH | 47 |
| Fab_8D3_H-H6 CDR2 | YISSGSTTIYYGDTVKG | 48 |
| Fab_8D3_H-H6 CDR3 | RPLYDGDYGYPMDY | 49 |
| Fab_8D3_H-H6 Framework | DVQLVESGGGLVQPGGSRKLSCAASGFTFS[$X_{3-13}$]WVRQAPEMGLEWV A[$X_{7-19}$]RFTISRDNPKNTLFLQMTSLRS EDTAMYYCAR[$X_{3-25}$]WGQGTSVTV SSASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPKS CGS<br>Where X is any amino acid, and in $X_{a-b}$, a indicates the minimum number of amino acids and b indicates the maximum number of amino acids | 58 |
| Fab_8D3_H-H6 without signal sequence | DVQLVESGGGLVQPGGSRKLSCAASGFTFSNFGMHWVRQAPEMGLEWVA YISSGSTTIYYGDTVKGRFTISRDNPKNTLFLQMTSLRSEDTAMYYCARRPL YDGDYGYPMDYWGQGTSVTVSSASTKGPSVFPLAPSSKSTSGGTAALGCL VKDYFPEPVTVSWNSGALTSGVHTFPAVLQSSGLYSLSSVVTVPSSSLGTQT YICNVNHKPSNTKVDKKVEPKSCGSHHHHHH | 17 |
| Fab_8D3_2_H-H6 | MDWTWRVFCLLAVAPGAHSDVQLVESGGGLVQPGKSLRLSCAASGFTFS NFGMHWVRQAPEMGLEWVAYISSGSTTKYYGDTVKGRFTISRDNPKNTLY LQMNSLRSEDTAMYYCARRPLYDGDYGYPMDYWGQGTSVTVSSASTKGP SVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCGSHHH HHH | 2 |

TABLE 1-continued

| Name | Sequence | SEQ ID NO |
|---|---|---|
| Fab_8D3_2_H-H6 without signal sequence | DVQLVESGGGLVQPGKSLRLSCAASGFTFSNFGMHWVRQAPEMGLEWVA YISSGSTTKYYGDTVKGRFTISRDNPKNTLYLQMNSLRSEDTAMYYCARRP LYDGDYGYPMDYWGQGTSVTVSSASTKGPSVFPLAPSSKSTSGGTAALGC LVKDYFPEPVTVSWNSGALTSGVHTFPAVLQSSGLYSLSSVVTVPSSSLGTQ TYICNVNHKPSNTKVDKKVEPKSCGSHHHHHH | 18 |
| Fab_8D3_2_H-H6 CDR1 | NFGMH | 50 |
| Fab_8D3_2_H-H6 CDR2 | YISSGSTTKYYGDTVKG | 51 |
| Fab_8D3_2_H-H6 CDR3 | RPLYDGDYGYPMDY | 52 |
| Fab_8D3_L & Fab_8D3_2_L | MVLQTQVFISLLLWISGAYGNIMLTQSPSSLAVSAGERVTMSCKSTQSILYN SNQKTYLAWYQQKPGQSPKLLIYWASTRASGVPDRFTGSGSGTDFTLTINS VQPEDLAVYYCHQYLSAWTFGGGTKLEIKRTVAAPSVFIFPPSDEQLKSGT ASVVCLLNNFYPREAKVQWKVDNALQSGNSQESVTEQDSKDSTYSLSSTL TLSKADYEKHKVYACEVTHQGLSSPVTKSFNRGEC | 3 |
| Fab_8D3_L & Fab_8D3_2_L without signal sequence | NIMLTQSPSSLAVSAGERVTMSCKSTQSILYNSNQKTYLAWYQQKPGQSPK LLIYWASTRASGVPDRFTGSGSGTDFTLTINSVQPEDLAVYYCHQYLSAWT FGGGTKLEIKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 19 |
| Fab_8D3_L & Fab_8D3_2_L framework | NIMLTQSPSSLAVSAGERVTMSC[$X_{3-17}$]WYQQKPGQSPKLLIYW[$X_{3-17}$] GVPDRFTGSGSGTDFTLTINSVQPEDLAVYYC[$X_{3-25}$] GGGTKLEIKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC<br>Where X is any amino acid, and in $X_{a-b}$, a indicates the minimum number of amino acids and b indicates the maximum number of amino acids | 59 |
| Fab_8D3_L & Fab_8D3_2_L CDR1 | KSTQSILYNSNQKTYLA | 53 |
| Fab_8D3_L & Fab_8D3_2_L CDR2 | WASTRAS | 54 |
| Fab_8D3_L & Fab_8D3_2_L CDR3 | HQYLSAWTF | 55 |
| Nb_N0-H6 | MKYLLPTAAAGLLLLAAQPAMAQVQLVEYGGGSVQAGGYLRLSCVASGS ISLSSGMGWYRQAPGKERELVASISGGSSTNYADSVKGRFTISRDNAKNTV YLQMNSLKPEDTAVYYCAASEQLTSGHAYWGQGTQVTVSSLEHHHHHH | 4 |
| Nb_N0-H6 without signal sequence | QVQLVEYGGGSVQAGGYLRLSCVASGSISLSSGMGWYRQAPGKERELVAS ISGGSSTNYADSVKGRFTISRDNAKNTVYLQMNSLKPEDTAVYYCAASEQL TSGHAYWGQGTQVTVSSLEHHHHHH | 20 |
| Nb_N0-H6 CDR1 | SISLSSG | 21 |
| Nb_N0-H6 CDR2 | LVASISGGSSTN | 22 |
| Nb_N0-H6 CDR3 | ASEQLTSGHA | 23 |

TABLE 1-continued

| Name | Sequence | SEQ ID NO |
|---|---|---|
| Nb_N0-H6 framework | QVQLVEYGGGSVQAGGYLRLSCVASG[X$_{3-13}$]MGWYRQAPGKERE[X$_{7-19}$]YADSVKGRFTISRDNAKNTVYLQMNSLKPEDTAVYYCA[X$_{3-28}$]YWGQGTQVTVSSLE (where X is any amino acid)<br>Where X is any amino acid, and in X$_{a-b}$, a indicates the minimum number of amino acids and b indicates the maximum number of amino acids | 24 |
| Nb MBP-Strep2 (derived from Sb_MBP#1) | MKYLLPTAAAGLLLLAAQPAMAQVQLVEYGGGSVQAGGSLRLSCVASGDIKYISYLGWFRQAPGKEREGVAALYTSTGRTYYADSVKGRFTVSLDNAKNTVYLQMNSLKPEDTAVYYCAAAEWGSQSPLTQWFYRYWGQGTQVTVSSGGENLYFQSGSSAWSHPQFEKGGGSGGGSGGSAWSHPQFEK | 5 |
| Nb MBP-Strep2 (derived from Sb_MBP#1) without signal sequence | QVQLVEYGGGSVQAGGSLRLSCVASGDIKYISYLGWFRQAPGKEREGVAALYTSTGRTYYADSVKGRFTVSLDNAKNTVYLQMNSLKPEDTAVYYCAAAEWGSQSPLTQWFYRYWGQGTQVTVSSGGENLYFQSGSSAWSHPQFEKGGGSGGGSGGSAWSHPQFEK | 25 |
| Nb_MBP-Strep2 CDR1 | DIKYISY | 26 |
| Nb_MBP-Strep2 CDR2 | GVAALYTSTGRTY | 27 |
| Nb_MBP-Strep2 CDR3 | AEWGSQSPLTQWFYR | 28 |
| Nb_MBP-Strep2 (derived from Sb_MBP#1) framework | QVQLVEYGGGSVQAGGSLRLSCVASG[X$_{3-13}$]LGWFRQAPGKERE[X$_{7-19}$]YADSVKGRFTVSLDNAKNTVYLQMNSLKPEDTAVYYCAA[X$_{3-28}$]YWGQGTQVTVSSGGENLYFQSGSSAWSHPQFEKGGGSGGGSGGSAWSHPQFEK<br>Where X is any amino acid, and in X$_{a-b}$, a indicates the minimum number of amino acids and b indicates the maximum number of amino acids | 29 |
| Nb_KR-H6 (derived from Syb37) | MKYLLPTAAAGLLLLAAQPAMAQVQLVESGGGLVQAGGSLRLSCAASGFPVKRWSMTWYRQAPGKEREWVAAIRSAGHWTHYADSVKGRFTISRDNAKNTVYLQMNSLKPEDTAVYYCNVKDEGDFSYWYDYWGQGTQVTVSSLEHHHHHH | 6 |
| Nb_KR-H6 (derived from Syb37) without signal sequence | QVQLVESGGGLVQAGGSLRLSCAASGFPVKRWSMTWYRQAPGKEREWVAAIRSAGHWTHYADSVKGRFTISRDNAKNTVYLQMNSLKPEDTAVYYCNVKDEGDFSYWYDYWGQGTQVTVSSLEHHHHHH | 30 |
| Nb_KR-H6 CDR1 | FPVKRWS | 31 |
| Nb_KR-H6 CDR2 | WVAAIRSAGHWTH | 32 |
| Nb_KR-H6 CDR3 | VKDEGDFSYWYD | 33 |
| Nb_KR-H6 (derived from Syb37) framework | QVQLVESGGGLVQAGGSLRLSCAASG[X$_{3-13}$]MTWYRQAPGKERE[X$_{7-19}$]YADSVKGRFTISRDNAKNTVYLQMNSLKPEDTAVYYCN[X$_{3-28}$]YWGQGTQVTVSSLE<br>Where X is any amino acid, and in X$_{a-b}$, a indicates the minimum number of amino acids and b indicates the maximum number of amino acids | 34 |
| Nb_ALFA-H6 | MKYLLPTAAAGLLLLAAQPAMAEVQLQESGGGLVQAGGSLRLSCTASGVTISALNAMAMGWYRQAPGKRRVMVAAVSERGNTMYRESVKGRFTVSRDFTNKTVYLQMNSLKPEDTAVYYCHVLEDRVDSFHDYWGQGTQVTVSSLEHHHHHH | 7 |

TABLE 1-continued

| Name | Sequence | SEQ ID NO |
|---|---|---|
| Nb_ALFA-H6 without signal sequence | EVQLQESGGGLVQAGGSLRLSCTASGVTISALNAMAMGWYRQAPGKRRV MVAAVSERGNTMYRESVKGRFTVSRDFTNKTVYLQMNSLKPEDTAVYYC HVLEDRVDSFHDYWGQGTQVTVSSLEHHHHHH | 35 |
| Nb_ALFA-H6 CDR1 | VTISALNAMA | 36 |
| Nb_ALFA-H6 CDR2 | MVAAVSERGNTM | 37 |
| Nb_ALFA-H6 CDR3 | VLEDRVDSFHD | 38 |
| Nb_ALFA-H6 framework | EVQLQESGGGLVQAGGSLRLSCTASG[$X_{3-13}$]MGWYRQAPGKRRV[$X_{7-19}$] YRESVKGRFTVSRDFTNKTV¥LQMNSLKPEDTAVYYCH[$X_{3-28}$] YWGQGTQVTVSSLE<br>Where X is any amino acid, and in $X_{a-b}$, a indicates the minimum number of amino acids and b indicates the maximum number of amino acids | 39 |
| Nb_RBD-H6 (derived from Sb#45) | MKYLLPTAAAGLLLLAAQPAMAQVQLVESGGGLVQAGGSLRLSCAASGF PVYRDRMAWYRQAPGKEREWVAAIYSAGQQTRYADSVKGRFTISRDNAK NTVYLQMNSLKPEDTAVYYCNVKDVGHHYEYYDYWGQGTQVTVSSLEH HHHHH | 8 |
| Nb_RBD-H6 (derived from Sb#45) without signal sequence | QVQLVESGGGLVQAGGSLRLSCAASGFPVYRDRMAWYRQAPGKEREWV AAIYSAGQQTRYADSVKGRFTISRDNAKNTVYLQMNSLKPEDTAVYYCNV KDVGHHYEYYDYWGQGTQVTVSSLEHHHHHH | 40 |
| Nb_RBD-H6 CDR1 | FPVYRDR | 41 |
| Nb_RBD-H6 CDR2 | WVAAIYSAGQQTR | 42 |
| Nb_RBD-H6 CDR3 | VKDVGHHYEYYD | 43 |
| Nb_RBD-H6 framework | QVQLVESGGGLVQAGGSLRLSCAASG[$X_{3-13}$]MAWYRQAPGKERE[$X_{7-19}$] YADSVKGRFTISRDNAKNTVYLQMNSLKPEDTAVYYCN[$X_{3-28}$] WGQGTQVTVSSLE<br>Where X is any amino acid, and in $X_{a-b}$, a indicates the minimum number of amino acids and b indicates the maximum number of amino acids | 44 |
| MBP_PrA/G-H6 | MKIEEGKLVIWINGDKGYNGLAEVGKKFEKDTGIKVTVEHPDKLEEKFPQ VAATGDGPDIIFWAHDRFGGYAQSGLLAEITPDKAFQDKLYPFTWDAVRY NGKLIAYPIAVEALSLIYNKDLLPNPPKTWEEIPALDKELKAKGKSALMFNL QEPYFTWPLIAADGGYAFKYENGKYDIKDVGVDNAGAKAGLTFLVDLIKN KHMNADTDYSIAEAAFNKGETAMTINGPWAWSNIDTSKVNYGVTVLPTFK GQPSKPFVGVLSAGINAASPNKELAKEFLENYLLTDEGLEAVNKDKPLGAV ALKSYEEELAKDPRIAATMENAQKGEIMPNIPQMSAFWYAVRTAVINAAS GRQTVDQALAFAQILIMPNLTEEQRNGFIQSLKDDPSVSKEILAEAKKLNEH QAPKGGSGGAGSGDQQSAFYEILNMPNLNEAQRNGFIQSLKDDPSQSTNVL GEAKKLNESQAGGGSGGGSGGSAVTTYKLVINGKTLKGETTTKAVDAETA EKAFKQYANDNGVDGVWTYDDATKTFTVTEGSGHHHHHH | 9 |
| H6-MBP_PrAC | MGHHHHHHKIEEGKLVIWINGDKGYNGLAEVGKKFEKDTGIKVTVEHPDK LEEKFPQVAATGDGPDIIFWAHDRFGGYAQSGLLAEITPDKAFQDKLYPFT WDAVRYNGKLIAYPIAVEALSLIYNKDLLPNPPKTWEEIPALDKELKAKGK SALMFNLQEPYFTWPLIAADGGYAFKYENGKYDIKDVGVDNAGAKAGLT FLVDLIKNKHMNADTDYSIAEAAFNKGETAMTINGPWAWSNIDTSKVNYG VTVLPTFKGQPSKPFVGVLSAGINAASPNKELAKEFLENYLLTDEGLEAVN KDKPLGAVALKSYEEELAKDPRIAATMENAQKGEIMPNIPQMSAFWYAVR TAVINAASGRQTVDQALAFAQILIMPNLTEEQRNGFIQSLKDDPSVSKEILA EAKKLNEAQAPK | 10 |
| MBP_PrAC | KIEEGKLVIWINGDKGYNGLAEVGKKFEKDTGIKVTVEHPDKLEEKFPQVA ATGDGPDIIFWAHDRFGGYAQSGLLAEITPDKAFQDKLYPFTWDAVRYNG KLIAYPIAVEALSLIYNKDLLPNPPKTWEEIPALDKELKAKGKSALMFNLQE PYFTWPLIAADGGYAFKYENGKYDIKDVGVDNAGAKAGLTFLVDLIKNKH MNADTDYSIAEAAFNKGETAMTINGPWAWSNIDTSKVNYGVTVLPTFKGQ | 45 |

TABLE 1-continued

| Name | Sequence | SEQ ID NO |
|------|----------|-----------|
| | PSKPFVGVLSAGINAASPNKELAKEFLENYLLTDEGLEAVNKDKPLGAVAL KSYEEELAKDPRIAATMENAQKGEIMPNIPQMSAFWYAVRTAVINAASGR QTVDQALAFAQILIMPNLTEEQRNGFIQSLKDDPSVSKEILAEAKKLNEAQA PK | |
| MBP_PrA/G | MKIEEGKLVIWINGDKGYNGLAEVGKKFEKDTGIKVTVEHPDKLEEKFPQ VAATGDGPDIIFWAHDRFGGYAQSGLLAEITPDKAFQDKLYPFTWDAVRY NGKLIAYPIAVEALSLIYNKDLLPNPPKTWEEIPALDKELKAKGKSALMFNL QEPYFTWPLIAADGGYAFKYENGKYDIKDVGVDNAGAKAGLTFLVDLIKN KHMNADTDYSIAEAAFNKGETAMTINGPWAWSNIDTSKVNYGVTVLPTFK GQPSKPFVGVLSAGINAASPNKELAKEFLENYLLTDEGLEAVNKDKPLGAV ALKSYEEELAKDPRIAATMENAQKGEIMPNIPQMSAFWYAVRTAVINAAS GRQTVDQALAFAQILIMPNLTEEQRNGFIQSLKDDPSVSKEILAEAKKLNEH QAPKGGSGGAGSGDQQSAFYEILNMPNLNEAQRNGFIQSLKDDPSQSTNVL GEAKKLNESQAGGGSGGGSGGSAVTTYKLVINGKTLKGETTTKAVDAETA EKAFKQYANDNGVDGVWTYDDATKTFTVTEGSG | 46 |
| H6-MBP_L_PrAC | MGHHHHHHKIEEGKLVIWINGDKGYNGLAEVGKKFEKDTGIKVTVEHPDK LEEKFPQVAATGDGPDIIFWAHDRFGGYAQSGLLAEITPDKAFQDKLYPFT WDAVRYNGKLIAYPIAVEALSLIYNKDLLPNPPKTWEEIPALDKELKAKGK SALMFNLQEPYFTWPLIAADGGYAFKYENGKYDIKDVGVDNAGAKAGLT FLVDLIKNKHMNADTDYSIAEAAFNKGETAMTINGPWAWSNIDTSKVNYG VTVLPTFKGQPSKPFVGVLSAGINAASPNKELAKEFLENYLLTDEGLEAVN KDKPLGAVALKSYEEELAKDPRIAATMENAQKGEIMPNIPQMSAFWYAVR TAVINAASGRQTVDEALKDAQTNSSSNNNNNNNNNLGENLYFQGEGSEQ QNAFYEILHLPNLTEEQRNGFIQSLKDDPSVSKEILAEAKKLNDAQAPK | 11 |
| H6-MBP_L_PrAD | MGHHHHHHKIEEGKLVIWINGDKGYNGLAEVGKKFEKDTGIKVTVEHPDK LEEKFPQVAATGDGPDIIFWAHDRFGGYAQSGLLAEITPDKAFQDKLYPFT WDAVRYNGKLIAYPIAVEALSLIYNKDLLPNPPKTWEEIPALDKELKAKGK SALMFNLQEPYFTWPLIAADGGYAFKYENGKYDIKDVGVDNAGAKAGLT FLVDLIKNKHMNADTDYSIAEAAFNKGETAMTINGPWAWSNIDTSKVNYG VTVLPTFKGQPSKPFVGVLSAGINAASPNKELAKEFLENYLLTDEGLEAVN KDKPLGAVALKSYEEELAKDPRIAATMENAQKGEIMPNIPQMSAFWYAVR TAVINAASGRQTVDEALKDAQTNSSSNNNNNNNNNLGENLYFQGEGSD QQSAFYEILNMPNLNEAQRNGFIQSLKDDPSQSTNVLGEAKKLNESQAPK | 12 |
| H6-MBP_L_PrAE | MGHHHHHHKIEEGKLVIWINGDKGYNGLAEVGKKFEKDTGIKVTVEHPDK LEEKFPQVAATGDGPDIIFWAHDRFGGYAQSGLLAEITPDKAFQDKLYPFT WDAVRYNGKLIAYPIAVEALSLIYNKDLLPNPPKTWEEIPALDKELKAKGK SALMFNLQEPYFTWPLIAADGGYAFKYENGKYDIKDVGVDNAGAKAGLT FLVDLIKNKHMNADTDYSIAEAAFNKGETAMTINGPWAWSNIDTSKVNYG VTVLPTFKGQPSKPFVGVLSAGINAASPNKELAKEFLENYLLTDEGLEAVN KDKPLGAVALKSYEEELAKDPRIAATMENAQKGEIMPNIPQMSAFWYAVR TAVINAASGRQTVDEALKDAQTNSSSNNNNNNNNNLGENLYFQGEGSA QQNAFYQVLNMPNLNADQRNGFIQSLKDDPSQSANVLGEAQKLNDSQAP K | 13 |
| KDELR-SBP | MNIFRLTGDLSHLAAIIILLLKIWKSRSCAGISGKSQLLFALVFTTRYLDLFTS FISLYNTSMKLIYIACSYATVYLIYMKFKATYDGNHDTFRVEFLIVPVGGLS FLVNHDFSPLEILWTFSIYLESVAILPQLFMISKTGEAETITTHYLFFLGLYRA LYLVNWIWRYYFEGFFDLIAVVAGVVQTVLYCDFFYLYVTKVLKGKKLSL PAGSGGENLYFQSGGGMDEKTTGWRGGHVVEGLAGELEQLRARLEHHPQ GQREP | 14 |
| FLAG-19RBD-H8 | MDWTWRVFCLLAVAPGAHSGDYKDDDDKGGENLYFQGGSGDSTGSSNL CPFGEVFNATRFASVYAWNRKRISNCVADYSVLYNSASFSTFKCYGVSPTK LNDLCFTNVYADSFVIRGDEVRQIAPGQTGKIADYNYKLPDDFTGCVIAWN SNNLDSKVGGNYNYLYRLFRKSNLKPFERDISTEIYQAGSTPCNGVEGFNC YFPLQSYGFQPTNGVGYQPYRVVVLSFELLHAPATVCGGGGSGSGHHHHH HHH | 15 |
| GST_ALFA peptide | MSPILGYWKIKGLVQPTRLLLEYLEEKYEEHLYERDEGDKWRNKKFELGL EFPNLPYYIDGDVKLTQSMAIIRYIADKHNMLGGCPKERAEISMLEGAVLDI RYGVSRIAYSKDFETLKVDFLSKLPEMLKMFEDRLCHKTYLNGDHVTHPD FMLYDALDVVLYMDPMCLDAFPKLVCFKKRIEAIPQIDKYLKSSKYIAWPL QGWQATFGGGDHPPKSDLEVLFQGPLGSGSGGSPSRLEEELRRRLTEP | 16 |
| E. coli MBP, mature form | kiee gklviwingd kgynglaevg kkfekdtgik vtvehpdkle ekfpqvaatg dgpdiifwah drfggyaqsg llaeitpdka fqdklypftw davryngkli aypiaveals liynkdllpn ppktweeipa ldkelkakgk salmfnlqep yftwpliaad ggyafkyeng kydikdvgvd nagakagltf lvdliknkhm nadtdysiae aafnkgetam tingpwawsn idtskvnygv tvlptfkgqp skpfvgvlsa ginaaspnke lakeflenyl ltdegleavn kdkplgaval ksyeeelakd priaatmena qkgeimpnip qmsafwyavr tavinaasgr qtvdealkda qtritk | 56 |

TABLE 1-continued

| Name | Sequence | SEQ ID NO |
|---|---|---|
| Protein A | 1 mkkkniysir klgvgiasvt lgtllisggv tpaanaaqhn eaqqnafyqv lnmpnlnaeq<br>61 rngfiqslkd dpsqsanvlg eaqklndsqa pkaeaqqnnf nkdqqsafyq ilnmpnlnee<br>121 qrngfiqslk ddpsqsnnll geaqklndsq apkadnkfnq eqqnafyeil hlpnlneeqr<br>181 ngfiqslkdd psqsanllae akklndsqap kadnkfnkeq qnafyeilhl pnlteeqrng<br>241 fiqslkddps vskeilaeak klndaqapkd ednnkpgked gnkpgkedgn kpgkedgnkp<br>301 gkedgnkpgk edgnkpgked gnkpgkedgn kpgkedgnkp gkedgnkpgk edgnkpgked<br>361 gngvhvvkpg dtvndiakah gttadkiaad nkladknmik pgqelvvdkk qqanhaeank<br>421 aqalpetgee npfigttvfg glslalgaal lagrrrel | 57 |

TABLE 2

X-ray data collection and refinement statistics.

| | Nb_0/Fab_8D3 |
|---|---|
| Data Accession | |
| PDB | xxxx |
| Data collection | |
| Space group | P 1 21 1 |
| Cell dimensions | |
| a, b, c (Å) | 64.51, 60.287, 77.244 |
| α, β, γ (°) | 90.00, 109.341, 90.00 |
| Resolution (Å) | 1.83 (1.895-1.83) * |
| $R_{merge}$ | 0.068 (0.55) |
| I/σI | 16.46 (2.95) |
| Completeness (%) | 99.35 (99.15) |
| Redundancy | 7.6 (7.1) |
| Model Refinement | |
| Software | Phenix |
| Resolution (Å) | 1.83 |
| No. Reflections | 49251 |
| $R_{work}/R_{free}$ | 0.18/0.21 |
| Number of non-hydrogen atoms | 4705 |
| Protein | 4211 |
| Water | 494 |
| Protein Residues | 554 |
| Average B factors (Å²) | |
| Protein | 36.13 |
| R.m.s. deviations | |
| Bond lengths (Å) | 0.01 |
| Bond angles (°) | 0.91 |
| Ramachandran statistics (%) | |
| Outliers | 0 |
| Allowed | 2.38 |
| Favored | 97.62 |
| MolProbity score | 1.37 |
| All-atom clashscore | 5.43 |
| Poor rotamers (%) | 0.64 |

* Values in parantheses are for highest-resolution shell.

TABLE 3

Cryo-EM data collection, refinement, and validation statistics.

| Structure | KDELR/Legobody | RBD/Legobody |
|---|---|---|
| Date Accession | | |
| PDB | 7RXC | 7RXD |
| EMDB | EMD-24728 | EMD-24729 |
| Data Collection | | |
| Microscope | Titan Krios | Titan Krios |
| Voltage (kV) | 300 | 300 |
| Exposure navigation | Stage Movement &beamshift | Stage Movement &beamshift |
| Automation software | SerialEM | SerialEM |
| Detector | Gatan K3 (Counting) | Gatan K3 (Counting) |
| Energy filter | 25 eV | 25 eV |
| Nominal magnification | 81k | 81k |
| Pixel Size (Å/pixel) | 1.06 | 1.06 |
| Exposure time (s), frames | 2.2, 50 | 2.16, 50 |
| Exposure rate (e⁻ pixel⁻¹ s⁻¹) | 26.31 | 26.18 |
| Electron exposure (e⁻/Å²) | 51.44 | 50.42 |
| Defocus range (μm) | −1.0 to −2.6 | −1.0 to −2.6 |
| Micrographs collected | 4,863 | 5795 |
| Reconstruction | | |
| Software | Relion 3.1 | Relion 3.1 |
| Micrographs used | 4,803 | 5095 |
| Particles used in refinement | 246,878 | 282,995 |
| Symmetry | C1 | C1 |
| Overall resolution (Å) | 3.2 | 3.6 |
| FSC = 0.143 (masked) | | |
| Map sharpening B-factor (Å2) | −100 | −130 |
| Local resolution range (Å) | 3.0-5.0 | 3.4-5.4 |
| Model Refinement | | |
| Software | Phenix | Phenix |
| Non-hydrogen atoms | 9361 | 9008 |
| Protein residues | 1178 | 1148 |
| Ligands | 5 | 1 |
| Average B factors (Å²) | | |
| Protein | 42.4 | 34.64 |
| Ligands | 34.2 | 34.45 |
| R.M.S. deviations | | |
| Bond length (Å) | 0.003 | 0.003 |
| Bond angle (°) | 0.578 | 0.615 |
| Ramachandran statistics (%) | | |
| Outliers | 0 | 0 |
| Allowed | 1.91 | 2.59 |
| Favored | 98.09 | 97.41 |
| MolProbity score | 1.45 | 1.64 |
| Clashscore | 8.22 | 10.03 |
| Poor rotamers (%) | 0 | 0 |
| Model vs. Map FSC | | |
| FSC = 0.5 (masked, Å) | 3.3 | 3.8 |

Example 2

Challenges for Cryo-EM include size, symmetry, compositional heterogeneity, conformational flexibility, and stability in solution and ice. As the target protein's size decreases, cryo-EM becomes more challenging as it is necessary to make the complex larger. Approaches to making the protein larger have included fusion based scaffolds and binder based scaffolds.

Fusion-based scaffolds, e.g., BRIL/Fab, MBP/Fab, were introduced as helical extensions at the N or C terminal or in loops of the target protein. Far from being an "universal scaffold", this approach is very tricky. When the fit is too tight, it may cause structure perturbation and if the fit is too loose it is not useful. This approach also requires prior structure knowledge to design the fusion.

Binder based scaffolds include DARpins that were obtained from a screening system. However, DARpin repeats are flexible by nature and this approach is not compatible with membrane proteins which have little exposure outside the membrane. When DARpin fusion scaffold may seem rigid, the resolution degenerates over distances. Another approach includes Fabs, and putting membrane proteins in a nanodisc. A further approach are nanobodies.

Although too small to be useful in cryo-electron microscopy by themselves, nanobodies can be made bigger with a fusion based approach (MEGABODY™). While this may guide initial alignment (20-30A), this level of flexibility will deteriorate alignment at secondary structure level, and is not good for driving alignments for small proteins.

Figure 13:
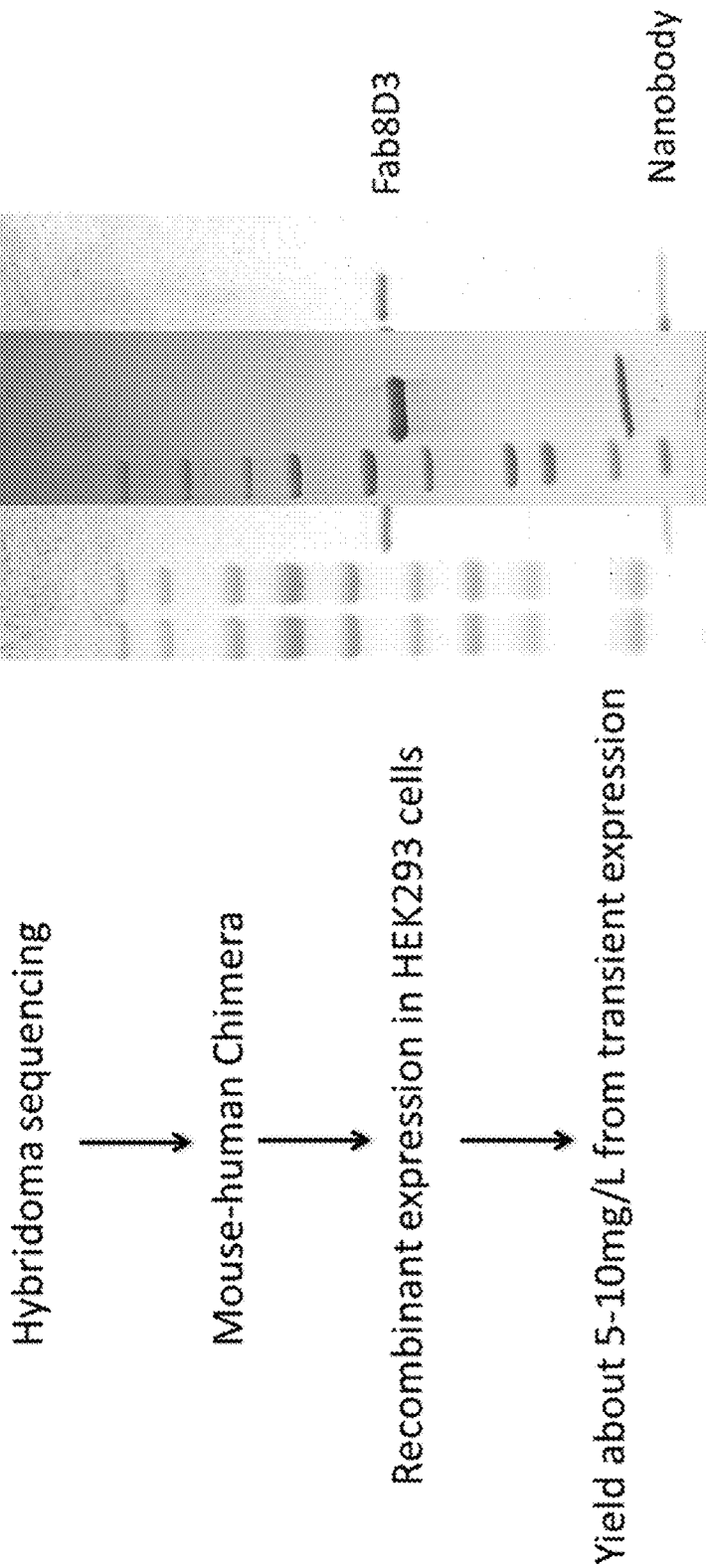
FIG. 13 depicts a schematic of an anti-nanobody antibody screen.

Described herein is an approach called Legobody. Using the experimental work flow shown in FIG. 13, an anti-nanobody antibody was identified. Crystal structure of the Fab bound to the nanobody was determined at 1.8A resolution (data not shown). A schematic is depicted in FIG. 2A and testing is shown in FIGS. 2B-2D.

The approach described herein permits cryo-EM of small membrane proteins, e.g., membrane-embedded enzymes, transporters, and GPCRs. This is demonstrated by cryo-EM of the KDEL receptor. KDELR was purified as shown in FIGS. 3B-3C, and bound by Legobody as shown in FIG. 4A. This demonstrates that by using a nanobody that binds the target well, the structure of the target can be determined immediately using cryoEM.

What is claimed herein is:

1. A polypeptide composition or kit comprising at least one of:
   a) a first polypeptide comprising:
      a nanobody that:
         i) specifically binds a target molecule, and
         ii) comprises a framework sequence with at least 95% sequence identity to the sequence any one of SEQ ID NOS: 24, 29, 34, 39, and 44;
   b) a second polypeptide comprising:
      an antibody that specifically binds the first polypeptide,
      an antigen-binding portion of an antibody that specifically binds the first polypeptide, or
      an antibody reagent that specifically binds the first polypeptide; and
   c) a third polypeptide comprising:
      i) at least one maltose binding protein (MBP) domain;
      ii) at least one domain of Protein A; and
      iii) at least one Protein G domain, Protein L domain, or Protein M domain).

2. The polypeptide composition or kit of claim 1, wherein the first polypeptide is a nanobody comprising the sequence of any one of SEQ ID Nos: 4, 20, 5, 25, 6, 30, 7, 35, 8, and 40.

3. The polypeptide composition or kit of claim 1, wherein the second polypeptide specifically binds a portion of the first polypeptide that is not a CDR of the first polypeptide.

4. The polypeptide composition or kit of claim 1, wherein the second polypeptide is a Fab.

5. The polypeptide composition or kit of claim 4, wherein the second polypeptide is a Fab comprising the framework sequence of any one of SEQ ID NOs: 58-59.

6. The polypeptide composition or kit of claim 5, wherein the second polypeptide is a Fab comprising the sequence of any one of SEQ ID NOs: 1, 17, 2, 18, 3, or 19.

7. The polypeptide composition or kit of claim 1, wherein the at least one domain of Protein A comprises or consists of: a domain C of Protein A and a domain D of protein A.

8. The polypeptide composition or kit of claim 1, wherein the at least one MBP domain and the at least one domain of Protein A are provided as a graft of the at least one MBP domain and the at least one domain of Protein A, the graft comprising a sequence with at least 95% sequence identity to the sequence of SEQ ID NO: 45.

9. The polypeptide composition or kit of claim 1, wherein the third polypeptide comprises a sequence with at least 95% sequence identity to the sequence of one of SEQ ID NOs: 9-13, 45 or 46.

10. The polypeptide composition or kit of claim 1, wherein the third polypeptide comprises a sequence with at least 95% sequence identity to the sequence of SEQ ID NO: 46.

11. The polypeptide composition or kit of claim 1, comprising the first polypeptide, the second polypeptide, and the third polypeptide.

12. The polypeptide composition or kit of claim 1, further comprising the target molecule.

13. The polypeptide composition or kit of claim 1, wherein the target molecule is a protein.

14. The polypeptide composition or kit of claim 1, wherein the target molecule is 100 kDa or less in size.

15. The polypeptide composition or kit of claim 1, wherein the target molecule is 70 kDa or less in size.

16. The polypeptide composition or kit of claim 1, wherein the target molecule is 50 kDa or less in size.

17. The polypeptide composition or kit of claim 1, wherein the target molecule is at least 3 kDa in size.

* * * * *

```
                            SEQUENCE LISTING

Sequence total quantity: 59
SEQ ID NO: 1            moltype = AA  length = 253
FEATURE                 Location/Qualifiers
source                  1..253
                        mol_type = protein
                        organism = synthetic construct
SEQUENCE: 1
MDWTWRVFCL LAVAPGAHSD VQLVESGGGL VQPGGSRKLS CAASGFTFSN FGMHWVRQAP   60
EMGLEWVAYI SSGSTTIYYG DTVKGRFTIS RDNPKNTLFL QMTSLRSEDT AMYYCARRPL  120
YDGDYGYPMD YWGQGTSVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCGSHHH HHH                                                    253

SEQ ID NO: 2            moltype = AA  length = 253
FEATURE                 Location/Qualifiers
source                  1..253
                        mol_type = protein
                        organism = synthetic construct
SEQUENCE: 2
MDWTWRVFCL LAVAPGAHSD VQLVESGGGL VQPGKSLRLS CAASGFTFSN FGMHWVRQAP   60
EMGLEWVAYI SSGSTTKYYG DTVKGRFTIS RDNPKNTLYL QMNSLRSEDT AMYYCARRPL  120
YDGDYGYPMD YWGQGTSVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCGSHHH HHH                                                    253

SEQ ID NO: 3            moltype = AA  length = 239
FEATURE                 Location/Qualifiers
source                  1..239
                        mol_type = protein
                        organism = synthetic construct
SEQUENCE: 3
MVLQTQVFIS LLLWISGAYG NIMLTQSPSS LAVSAGERVT MSCKSTQSIL YNSNQKTYLA   60
WYQQKPGQSP KLLIYWASTR ASGVPDRFTG SGSGTDFTLT INSVQPEDLA VYYCHQYLSA  120
WTFGGGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 4            moltype = AA  length = 148
FEATURE                 Location/Qualifiers
source                  1..148
                        mol_type = protein
                        organism = synthetic construct
SEQUENCE: 4
MKYLLPTAAA GLLLLAAQPA MAQVQLVEYG GGSVQAGGYL RLSCVASGSI SLSSGMGWYR   60
QAPGKERELV ASISGGSSTN YADSVKGRFT ISRDNAKNTV YLQMNSLKPE DTAVYYCAAS  120
EQLTSGHAYW GQGTQVTVSS LEHHHHHH                                    148

SEQ ID NO: 5            moltype = AA  length = 188
FEATURE                 Location/Qualifiers
source                  1..188
                        mol_type = protein
                        organism = synthetic construct
SEQUENCE: 5
```

```
MKYLLPTAAA GLLLLAAQPA MAQVQLVEYG GGSVQAGGSL RLSCVASGDI KYISYLGWFR    60
QAPGKEREGV AALYTSTGRT YYADSVKGRF TVSLDNAKNT VYLQMNSLKP EDTAVYYCAA   120
AEWGSQSPLT QWFYRYWGQG TQVTVSSGGE NLYFQSGSSA WSHPQFEKGG GSGGGSGGSA   180
WSHPQFEK                                                           188

SEQ ID NO: 6           moltype = AA   length = 151
FEATURE                Location/Qualifiers
source                 1..151
                       mol_type = protein
                       organism = synthetic construct
SEQUENCE: 6
MKYLLPTAAA GLLLLAAQPA MAQVQLVESG GGLVQAGGSL RLSCAASGFP VKRWSMTWYR    60
QAPGKEREWV AAIRSAGHWT HYADSVKGRF TISRDNAKNT VYLQMNSLKP EDTAVYYCNV   120
KDEGDFSYWY DYWGQGTQVT VSSLEHHHHH H                                 151

SEQ ID NO: 7           moltype = AA   length = 152
FEATURE                Location/Qualifiers
source                 1..152
                       mol_type = protein
                       organism = synthetic construct
SEQUENCE: 7
MKYLLPTAAA GLLLLAAQPA MAEVQLQESG GGLVQAGGSL RLSCTASGVT ISALNAMAMG    60
WYRQAPGKRR VMVAAVSERG NTMYRESVKG RFTVSRDFTN KTVYLQMNSL KPEDTAVYYC   120
HVLEDRVDSF HDYWGQGTQV TVSSLEHHHH HH                                152

SEQ ID NO: 8           moltype = AA   length = 151
FEATURE                Location/Qualifiers
source                 1..151
                       mol_type = protein
                       organism = synthetic construct
SEQUENCE: 8
MKYLLPTAAA GLLLLAAQPA MAQVQLVESG GGLVQAGGSL RLSCAASGFP VYRDRMAWYR    60
QAPGKEREWV AAIYSAGQQT RYADSVKGRF TISRDNAKNT VYLQMNSLKP EDTAVYYCNV   120
KDVGHHYEYY DYWGQGTQVT VSSLEHHHHH H                                 151

SEQ ID NO: 9           moltype = AA   length = 545
FEATURE                Location/Qualifiers
source                 1..545
                       mol_type = protein
                       organism = synthetic construct
SEQUENCE: 9
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDQ   360
ALAFAQILIM PNLTEEQRNG FIQSLKDDPS VSKEILAEAK KLNEHQAPKG GSGGAGSGDQ   420
QSAFYEILNM PNLNEEQRNG FIQSLKDDPS QSTNVLGEAK KLNESQAGGG SGGGSGGSAV   480
TTYKLVINGK TLKGETTTKA VDAETAEKAF KQYANDNGVD GVWTYDDATK TFTVTEGSGH   540
HHHHH                                                              545

SEQ ID NO: 10          moltype = AA   length = 416
FEATURE                Location/Qualifiers
source                 1..416
                       mol_type = protein
                       organism = synthetic construct
SEQUENCE: 10
MGHHHHHHKI EEGKLVIWIN GDKGYNGLAE VGKKFEKDTG IKVTVEHPDK LEEKFPQVAA    60
TGDGPDIIFW AHDRFGGYAQ SGLLAEITPD KAFQDKLYPF TWDAVRYNGK LIAYPIAVEA   120
LSLIYNKDLL PNPPKTWEEI PALDKELKAK GKSALMFNLQ EPYFTWPLIA ADGGYAFKYE   180
NGKYDIKDVG VDNAGAKAGL TFLVDLIKNK HMNADTDYSI AEAAFNKGET AMTINGPWAW   240
SNIDTSKVNY GVTVLPTFKG QPSKPFVGVL SAGINAASPN KELAKEFLEN YLLTDEGLEA   300
VNKDKPLGAV ALKSYEEELA KDPRIAATME NAQKGEIMPN IPQMSAFWYA VRTAVINAAS   360
GRQTVDQALA FAQILIMPNL TEEQRNGFIQ SLKDDPSVSK EILAEAKKLN EAQAPK       416

SEQ ID NO: 11          moltype = AA   length = 451
FEATURE                Location/Qualifiers
source                 1..451
                       mol_type = protein
                       organism = synthetic construct
SEQUENCE: 11
MGHHHHHHKI EEGKLVIWIN GDKGYNGLAE VGKKFEKDTG IKVTVEHPDK LEEKFPQVAA    60
TGDGPDIIFW AHDRFGGYAQ SGLLAEITPD KAFQDKLYPF TWDAVRYNGK LIAYPIAVEA   120
LSLIYNKDLL PNPPKTWEEI PALDKELKAK GKSALMFNLQ EPYFTWPLIA ADGGYAFKYE   180
NGKYDIKDVG VDNAGAKAGL TFLVDLIKNK HMNADTDYSI AEAAFNKGET AMTINGPWAW   240
SNIDTSKVNY GVTVLPTFKG QPSKPFVGVL SAGINAASPN KELAKEFLEN YLLTDEGLEA   300
VNKDKPLGAV ALKSYEEELA KDPRIAATME NAQKGEIMPN IPQMSAFWYA VRTAVINAAS   360
GRQTVDEALK DAQTNSSSNN NNNNNNNLG ENLYFQGEGS EQQNAFYEIL HLPNLTEEQR    420
```

```
NGFIQSLKDD PSVSKEILAE AKKLNDAQAP K                                451

SEQ ID NO: 12           moltype = AA  length = 451
FEATURE                 Location/Qualifiers
source                  1..451
                        mol_type = protein
                        organism = synthetic construct
SEQUENCE: 12
MGHHHHHHKI EEGKLVIWIN GDKGYNGLAE VGKKFEKDTG IKVTVEHPDK LEEKFPQVAA   60
TGDGPDIIFW AHDRFGGYAQ SGLLAEITPD KAFQDKLYPF TWDAVRYNGK LIAYPIAVEA  120
LSLIYNKDLL PNPPKTWEEI PALDKELKAK GKSALMFNLQ EPYFTWPLIA ADGGYAFKYE  180
NGKYDIKDVG VDNAGAKAGL TFLVDLIKNK HMNADTDYSI AEAAFNKGET AMTINGPWAW  240
SNIDTSKVNY GVTVLPTFKG QPSKPFVGVL SAGINAASPN KELAKEFLEN YLLTDEGLEA  300
VNKDKPLGAV ALKSYEEELA KDPRIAATME NAQKGEIMPN IPQMSAFWYA VRTAVINAAS  360
GRQTVDEALK DAQTNSSSNN NNNNNNNNLG ENLYFQGEGS DQQSAFYEIL NMPNLNEAQR  420
NGFIQSLKDD PSQSTNVLGE AKKLNESQAP K                                451

SEQ ID NO: 13           moltype = AA  length = 451
FEATURE                 Location/Qualifiers
source                  1..451
                        mol_type = protein
                        organism = synthetic construct
SEQUENCE: 13
MGHHHHHHKI EEGKLVIWIN GDKGYNGLAE VGKKFEKDTG IKVTVEHPDK LEEKFPQVAA   60
TGDGPDIIFW AHDRFGGYAQ SGLLAEITPD KAFQDKLYPF TWDAVRYNGK LIAYPIAVEA  120
LSLIYNKDLL PNPPKTWEEI PALDKELKAK GKSALMFNLQ EPYFTWPLIA ADGGYAFKYE  180
NGKYDIKDVG VDNAGAKAGL TFLVDLIKNK HMNADTDYSI AEAAFNKGET AMTINGPWAW  240
SNIDTSKVNY GVTVLPTFKG QPSKPFVGVL SAGINAASPN KELAKEFLEN YLLTDEGLEA  300
VNKDKPLGAV ALKSYEEELA KDPRIAATME NAQKGEIMPN IPQMSAFWYA VRTAVINAAS  360
GRQTVDEALK DAQTNSSSNN NNNNNNNNLG ENLYFQGEGS AQQNAFYQVL NMPNLNADQR  420
NGFIQSLKDD PSQSANVLGE AQKLNDSQAP K                                451

SEQ ID NO: 14           moltype = AA  length = 264
FEATURE                 Location/Qualifiers
source                  1..264
                        mol_type = protein
                        organism = synthetic construct
SEQUENCE: 14
MNIFRLTGDL SHLAAIIILL LKIWKSRSCA GISGKSQLLF ALVFTTRYLD LFTSFISLYN   60
TSMKLIYIAC SYATVYLIYM KFKATYDGNH DTFRVEFLIV PVGGLSFLVN HDFSPLEILW  120
TFSIYLESVA ILPQLFMISK TGEAETITTH YLFFLGLYRA LYLVNWIWRY YFEGFFDLIA  180
VVAGVVQTVL YCDFFYLYVT KVLKGKKLSL PAGSGGENLY FQSGGGMDEK TTGWRGGHVV  240
EGLAGELEQL RARLEHHPQG QREP                                        264

SEQ ID NO: 15           moltype = AA  length = 254
FEATURE                 Location/Qualifiers
source                  1..254
                        mol_type = protein
                        organism = synthetic construct
SEQUENCE: 15
MDWTWRVFCL LAVAPGAHSG DYKDDDDKGG ENLYFQGGSG DSTGSSNLCP FGEVFNATRF   60
ASVYAWNRKR ISNCVADYSV LYNSASFSTF KCYGVSPTKL NDLCFTNVYA DSFVIRGDEV  120
RQIAPGQTGK IADYNYKLPD DFTGCVIAWN SNNLDSKVGG NYNYLYRLFR KSNLKPFERD  180
ISTEIYQAGS TPCNGVEGFN CYFPLQSYGF QPTNGVGYQP YRVVVLSFEL LHAPATVCGG  240
GGSGSGHHHH HHHH                                                   254

SEQ ID NO: 16           moltype = AA  length = 251
FEATURE                 Location/Qualifiers
source                  1..251
                        mol_type = protein
                        organism = synthetic construct
SEQUENCE: 16
MSPILGYWKI KGLVQPTRLL LEYLEEKYEE HLYERDEGDK WRNKKFELGL EFPNLPYYID   60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LEVLFQGPLG SGSGGSPSRL  240
EEELRRRLTE P                                                      251

SEQ ID NO: 17           moltype = AA  length = 234
FEATURE                 Location/Qualifiers
source                  1..234
                        mol_type = protein
                        organism = synthetic construct
SEQUENCE: 17
DVQLVESGGG LVQPGGSRKL SCAASGFTFS NFGMHWVRQA PEMGLEWVAY ISSGSTTIYY   60
GDTVKGRFTI SRDNPKNTLF LQMTSLRSED TAMYYCARRP LYDGDYGYPM DYWGQGTSVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGSHH HHHH        234
```

```
SEQ ID NO: 18             moltype = AA  length = 234
FEATURE                   Location/Qualifiers
source                    1..234
                          mol_type = protein
                          organism = synthetic construct
SEQUENCE: 18
DVQLVESGGG LVQPGKSLRL SCAASGFTFS NFGMHWVRQA PEMGLEWVAY ISSGSTTKYY    60
GDTVKGRFTI SRDNPKNTLY LQMNSLRSED TAMYYCARRP LYDGDYGYPM DYWGQGTSVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCGSHH HHHH         234

SEQ ID NO: 19             moltype = AA  length = 219
FEATURE                   Location/Qualifiers
source                    1..219
                          mol_type = protein
                          organism = synthetic construct
SEQUENCE: 19
NIMLTQSPSS LAVSAGERVT MSCKSTQSIL YNSNQKTYLA WYQQKPGQSP KLLIYWASTR    60
ASGVPDRFTG SGSGTDFTLT INSVQPEDLA VYYCHQYLSA WTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 20             moltype = AA  length = 126
FEATURE                   Location/Qualifiers
source                    1..126
                          mol_type = protein
                          organism = synthetic construct
SEQUENCE: 20
QVQLVEYGGG SVQAGGYLRL SCVASGSISL SSGMGWYRQA PGKERELVAS ISGGSSTNYA    60
DSVKGRFTIS RDNAKNTVYL QMNSLKPEDT AVYYCAASEQ LTSGHAYWGQ GTQVTVSSLE   120
HHHHHH                                                              126

SEQ ID NO: 21             moltype = AA  length = 7
FEATURE                   Location/Qualifiers
source                    1..7
                          mol_type = protein
                          organism = synthetic construct
SEQUENCE: 21
SISLSSG                                                             7

SEQ ID NO: 22             moltype = AA  length = 12
FEATURE                   Location/Qualifiers
source                    1..12
                          mol_type = protein
                          organism = synthetic construct
SEQUENCE: 22
LVASISGGSS TN                                                       12

SEQ ID NO: 23             moltype = AA  length = 10
FEATURE                   Location/Qualifiers
source                    1..10
                          mol_type = protein
                          organism = synthetic construct
SEQUENCE: 23
ASEQLTSGHA                                                          10

SEQ ID NO: 24             moltype = AA  length = 94
FEATURE                   Location/Qualifiers
source                    1..94
                          mol_type = protein
                          organism = synthetic construct
VARIANT                   41
                          note = This site may encompass 7-19 amino acids, where X is
                           any amino acid
VARIANT                   27
                          note = This site may encompass 3-13 amino acids, where X is
                           any amino acid
VARIANT                   80
                          note = This site may encompass 3-28 amino acids, where X is
                           any amino acid
REGION                    1..94
                          note = Description of Artificial Sequence: Synthetic
                           polypeptide
SEQUENCE: 24
QVQLVEYGGG SVQAGGYLRL SCVASGXMGW YRQAPGKERE XYADSVKGRF TISRDNAKNT    60
VYLQMNSLKP EDTAVYYCAX YWGQGTQVTV SSLE                                94

SEQ ID NO: 25             moltype = AA  length = 166
FEATURE                   Location/Qualifiers
```

```
source                  1..166
                        mol_type = protein
                        organism = synthetic construct
SEQUENCE: 25
QVQLVEYGGG SVQAGGSLRL SCVASGDIKY ISYLGWFRQA PGKEREGVAA LYTSTGRTYY    60
ADSVKGRFTV SLDNAKNTVY LQMNSLKPED TAVYYCAAAE WGSQSPLTQW FYRYWGQGTQ   120
VTVSSGGENL YFQSGSSAWS HPQFEKGGGS GGGSGGSAWS HPQFEK                  166

SEQ ID NO: 26           moltype = AA   length = 7
FEATURE                 Location/Qualifiers
source                  1..7
                        mol_type = protein
                        organism = synthetic construct
SEQUENCE: 26
DIKYISY                                                               7

SEQ ID NO: 27           moltype = AA   length = 13
FEATURE                 Location/Qualifiers
source                  1..13
                        mol_type = protein
                        organism = synthetic construct
SEQUENCE: 27
GVAALYTSTG RTY                                                       13

SEQ ID NO: 28           moltype = AA   length = 15
FEATURE                 Location/Qualifiers
source                  1..15
                        mol_type = protein
                        organism = synthetic construct
SEQUENCE: 28
AEWGSQSPLT QWFYR                                                     15

SEQ ID NO: 29           moltype = AA   length = 134
FEATURE                 Location/Qualifiers
REGION                  1..134
                        note = Description of Artificial Sequence: Synthetic
                          polypeptide
VARIANT                 27
                        note = This site may encompass 3-13 amino acids, where X is
                          any amino acid
VARIANT                 41
                        note = This site may encompass 7-19 amino acids, where X is
                          any amino acid
VARIANT                 81
                        note = This site may encompass 3-28 amino acids, where X is
                          any amino acid
source                  1..134
                        mol_type = protein
                        organism = synthetic construct
SEQUENCE: 29
QVQLVEYGGG SVQAGGSLRL SCVASGXLGW FRQAPGKERE XYADSVKGRF TVSLDNAKNT    60
VYLQMNSLKP EDTAVYYCAA XYWGQGTQVT VSSGGENLYF QSGSSAWSHP QFEKGGGSGG   120
GSGGSAWSHP QFEK                                                     134

SEQ ID NO: 30           moltype = AA   length = 129
FEATURE                 Location/Qualifiers
source                  1..129
                        mol_type = protein
                        organism = synthetic construct
SEQUENCE: 30
QVQLVESGGG LVQAGGSLRL SCAASGFPVK RWSMTWYRQA PGKEREWVAA IRSAGHWTHY    60
ADSVKGRFTI SRDNAKNTVY LQMNSLKPED TAVYYCNVKD EGDFSYWYDY WGQGTQVTVS   120
SLEHHHHHH                                                           129

SEQ ID NO: 31           moltype = AA   length = 7
FEATURE                 Location/Qualifiers
source                  1..7
                        mol_type = protein
                        organism = synthetic construct
SEQUENCE: 31
FPVKRWS                                                               7

SEQ ID NO: 32           moltype = AA   length = 13
FEATURE                 Location/Qualifiers
source                  1..13
                        mol_type = protein
                        organism = synthetic construct
SEQUENCE: 32
WVAAIRSAGH WTH                                                       13
```

-continued

| | | |
|---|---|---|
| SEQ ID NO: 33 | moltype = AA length = 12 | |
| FEATURE | Location/Qualifiers | |
| source | 1..12 | |
| | mol_type = protein | |
| | organism = synthetic construct | |
| SEQUENCE: 33 | | |
| VKDEGDFSYW YD | | 12 |
| | | |
| SEQ ID NO: 34 | moltype = AA length = 94 | |
| FEATURE | Location/Qualifiers | |
| REGION | 1..94 | |
| | note = Description of Artificial Sequence: Synthetic polypeptide | |
| VARIANT | 27 | |
| | note = This site may encompass 3-13 amino acids, where X is any amino acid | |
| VARIANT | 41 | |
| | note = This site may encompass 7-19 amino acids, where X is any amino acid | |
| VARIANT | 80 | |
| | note = This site may encompass 3-28 amino acids, where X is any amino acid | |
| source | 1..94 | |
| | mol_type = protein | |
| | organism = synthetic construct | |
| SEQUENCE: 34 | | |
| QVQLVESGGG LVQAGGSLRL SCAASGXMTW YRQAPGKERE XYADSVKGRF TISRDNAKNT | | 60 |
| VYLQMNSLKP EDTAVYYCNX YWGQGTQVTV SSLE | | 94 |
| | | |
| SEQ ID NO: 35 | moltype = AA length = 130 | |
| FEATURE | Location/Qualifiers | |
| source | 1..130 | |
| | mol_type = protein | |
| | organism = synthetic construct | |
| SEQUENCE: 35 | | |
| EVQLQESGGG LVQAGGSLRL SCTASGVTIS ALNAMAMGWY RQAPGKRRVM VAAVSERGNT | | 60 |
| MYRESVKGRF TVSRDFTNKT VYLQMNSLKP EDTAVYYCHV LEDRVDSFHD YWGQGTQVTV | | 120 |
| SSLEHHHHHH | | 130 |
| | | |
| SEQ ID NO: 36 | moltype = AA length = 10 | |
| FEATURE | Location/Qualifiers | |
| source | 1..10 | |
| | mol_type = protein | |
| | organism = synthetic construct | |
| SEQUENCE: 36 | | |
| VTISALNAMA | | 10 |
| | | |
| SEQ ID NO: 37 | moltype = AA length = 12 | |
| FEATURE | Location/Qualifiers | |
| source | 1..12 | |
| | mol_type = protein | |
| | organism = synthetic construct | |
| SEQUENCE: 37 | | |
| MVAAVSERGN TM | | 12 |
| | | |
| SEQ ID NO: 38 | moltype = AA length = 11 | |
| FEATURE | Location/Qualifiers | |
| source | 1..11 | |
| | mol_type = protein | |
| | organism = synthetic construct | |
| SEQUENCE: 38 | | |
| VLEDRVDSFH D | | 11 |
| | | |
| SEQ ID NO: 39 | moltype = AA length = 94 | |
| FEATURE | Location/Qualifiers | |
| source | 1..94 | |
| | mol_type = protein | |
| | organism = synthetic construct | |
| VARIANT | 41 | |
| | note = This region encompasses 7-19 amino acids, where X is any amino acid | |
| VARIANT | 80 | |
| | note = This region encompasses 3-28 amino acids, where X is any amino acid | |
| VARIANT | 27 | |
| | note = This region encompasses 3-13 amino acids, where X is any amino acid | |
| SEQUENCE: 39 | | |

```
EVQLQESGGG LVQAGGSLRL SCTASGXMGW YRQAPGKRRV XYRESVKGRF TVSRDFTNKT   60
VYLQMNSLKP EDTAVYYCHX YWGQGTQVTV SSLE                              94

SEQ ID NO: 40          moltype = AA  length = 129
FEATURE                Location/Qualifiers
source                 1..129
                       mol_type = protein
                       organism = synthetic construct
SEQUENCE: 40
QVQLVESGGG LVQAGGSLRL SCAASGFPVY RDRMAWYRQA PGKEREWVAA IYSAGQQTRY   60
ADSVKGRFTI SRDNAKNTVY LQMNSLKPED TAVYYCNVKD VGHHYEYYDY WGQGTQVTVS  120
SLEHHHHHH                                                         129

SEQ ID NO: 41          moltype = AA  length = 7
FEATURE                Location/Qualifiers
source                 1..7
                       mol_type = protein
                       organism = synthetic construct
SEQUENCE: 41
FPVYRDR                                                             7

SEQ ID NO: 42          moltype = AA  length = 13
FEATURE                Location/Qualifiers
source                 1..13
                       mol_type = protein
                       organism = synthetic construct
SEQUENCE: 42
WVAAIYSAGQ QTR                                                     13

SEQ ID NO: 43          moltype = AA  length = 12
FEATURE                Location/Qualifiers
source                 1..12
                       mol_type = protein
                       organism = synthetic construct
SEQUENCE: 43
VKDVGHHYEY YD                                                      12

SEQ ID NO: 44          moltype = AA  length = 93
FEATURE                Location/Qualifiers
source                 1..93
                       mol_type = protein
                       organism = synthetic construct
VARIANT                27
                       note = This site may encompass 3-13 amino acids, where X is
                         any amino acid
VARIANT                41
                       note = This site may encompass 7-19 amino acids, where X is
                         any amino acid
VARIANT                80
                       note = This site may encompass 3-28 amino acids, where X is
                         any amino acid
REGION                 1..93
                       note = Description of Artificial Sequence: Synthetic
                         polypeptide
SEQUENCE: 44
QVQLVESGGG LVQAGGSLRL SCAASGXMAW YRQAPGKERE XYADSVKGRF TISRDNAKNT   60
VYLQMNSLKP EDTAVYYCNX WGQGTQVTVS SLE                               93

SEQ ID NO: 45          moltype = AA  length = 408
FEATURE                Location/Qualifiers
source                 1..408
                       mol_type = protein
                       organism = synthetic construct
SEQUENCE: 45
KIEEGKLVIW INGDKGYNGL AEVGKKFEKD TGIKVTVEHP DKLEEKFPQV AATGDGPDII   60
FWAHDRFGGY AQSGLLAEIT PDKAFQDKLY PFTWDAVRYN GKLIAYPIAV EALSLIYNKD  120
LLPNPPKTWE EIPALDKELK AKGKSALMFN LQEPYFTWPL IAADGGYAFK YENGKYDIKD  180
VGVDNAGAKA GLTFLVDLIK NKHMNADTDY SIAEAAFNKG ETAMTINGPW AWSNIDTSKV  240
NYGVTVLPTF KGQPSKPFVG VLSAGINAAS PNKELAKEFL ENYLLTDEGL EAVNKDKPLG  300
AVALKSYEEE LAKDPRIAAT MENAQKGEIM PNIPQMSAFW YAVRTAVINA ASGRQTVDQA  360
LAFAQILIMP NLTEEQRNGF IQSLKDDPSV SKEILAEAKK LNEAQAPK              408

SEQ ID NO: 46          moltype = AA  length = 539
FEATURE                Location/Qualifiers
source                 1..539
                       mol_type = protein
                       organism = synthetic construct
SEQUENCE: 46
MKIEEGKLVI WINGDKGYNG LAEVGKKFEK DTGIKVTVEH PDKLEEKFPQ VAATGDGPDI   60
```

```
IFWAHDRFGG YAQSGLLAEI TPDKAFQDKL YPFTWDAVRY NGKLIAYPIA VEALSLIYNK    120
DLLPNPPKTW EEIPALDKEL KAKGKSALMF NLQEPYFTWP LIAADGGYAF KYENGKYDIK    180
DVGVDNAGAK AGLTFLVDLI KNKHMNADTD YSIAEAAFNK GETAMTINGP WAWSNIDTSK    240
VNYGVTVLPT FKGQPSKPFV GVLSAGINAA SPNKELAKEF LENYLLTDEG LEAVNKDKPL    300
GAVALKSYEE ELAKDPRIAA TMENAQKGEI MPNIPQMSAF WYAVRTAVIN AASGRQTVDQ    360
ALAFAQILIM PNLTEEQRNG FIQSLKDDPS VSKEILAEAK KLNEHQAPKG GSGGAGSGDQ    420
QSAFYEILNM PNLNEAQRNG FIQSLKDDPS QSTNVLGEAK KLNESQAGGG SGGGSGGSAV    480
TTYKLVINGK TLKGETTTKA VDAETAEKAF KQYANDNGVD GVWTYDDATK TFTVTEGSG     539

SEQ ID NO: 47          moltype = AA  length = 5
FEATURE                Location/Qualifiers
source                 1..5
                       mol_type = protein
                       organism = synthetic construct
SEQUENCE: 47
NFGMH                                                                  5

SEQ ID NO: 48          moltype = AA  length = 17
FEATURE                Location/Qualifiers
source                 1..17
                       mol_type = protein
                       organism = synthetic construct
SEQUENCE: 48
YISSGSTTIY YGDTVKG                                                    17

SEQ ID NO: 49          moltype = AA  length = 14
FEATURE                Location/Qualifiers
source                 1..14
                       mol_type = protein
                       organism = synthetic construct
SEQUENCE: 49
RPLYDGDYGY PMDY                                                       14

SEQ ID NO: 50          moltype = AA  length = 5
FEATURE                Location/Qualifiers
source                 1..5
                       mol_type = protein
                       organism = synthetic construct
SEQUENCE: 50
NFGMH                                                                  5

SEQ ID NO: 51          moltype = AA  length = 17
FEATURE                Location/Qualifiers
source                 1..17
                       mol_type = protein
                       organism = synthetic construct
SEQUENCE: 51
YISSGSTTKY YGDTVKG                                                    17

SEQ ID NO: 52          moltype = AA  length = 14
FEATURE                Location/Qualifiers
source                 1..14
                       mol_type = protein
                       organism = synthetic construct
SEQUENCE: 52
RPLYDGDYGY PMDY                                                       14

SEQ ID NO: 53          moltype = AA  length = 17
FEATURE                Location/Qualifiers
source                 1..17
                       mol_type = protein
                       organism = synthetic construct
SEQUENCE: 53
KSTQSILYNS NQKTYLA                                                    17

SEQ ID NO: 54          moltype = AA  length = 7
FEATURE                Location/Qualifiers
source                 1..7
                       mol_type = protein
                       organism = synthetic construct
SEQUENCE: 54
WASTRAS                                                                7

SEQ ID NO: 55          moltype = AA  length = 9
FEATURE                Location/Qualifiers
source                 1..9
                       mol_type = protein
                       organism = synthetic construct
SEQUENCE: 55
```

```
HQYLSAWTF                                                                      9

SEQ ID NO: 56           moltype = AA  length = 370
FEATURE                 Location/Qualifiers
source                  1..370
                        mol_type = protein
                        organism = Escherichia coli
SEQUENCE: 56
KIEEGKLVIW INGDKGYNGL AEVGKKFEKD TGIKVTVEHP DKLEEKFPQV AATGDGPDII    60
FWAHDRFGGY AQSGLLAEIT PDKAFQDKLY PFTWDAVRYN GKLIAYPIAV EALSLIYNKD   120
LLPNPPKTWE EIPALDKELK AKGKSALMFN LQEPYFTWPL IAADGGYAFK YENGKYDIKD   180
VGVDNAGAKA GLTFLVDLIK NKHMNADTDY SIAEAAFNKG ETAMTINGPW AWSNIDTSKV   240
NYGVTVLPTF KGQPSKPFVG VLSAGINAAS PNKELAKEFL ENYLLTDEGL EAVNKDKPLG   300
AVALKSYEEE LAKDPRIAAT MENAQKGEIM PNIPQMSAFW YAVRTAVINA ASGRQTVDEA   360
LKDAQTRITK                                                         370

SEQ ID NO: 57           moltype = AA  length = 458
FEATURE                 Location/Qualifiers
source                  1..458
                        mol_type = protein
                        organism = Staphylococcus aureus
SEQUENCE: 57
MKKKNIYSIR KLGVGIASVT LGTLLISGGV TPAANAAQHN EAQQNAFYQV LNMPNLNAEQ    60
RNGFIQSLKD DPSQSANVLG EAQKLNDSQA PKAEAQQNNF NKDQQSAFYQ ILNMPNLNEE   120
QRNGFIQSLK DDPSQSNNLL GEAQKLNDSQ APKADNKFNQ EQQNAFYEIL HLPNLNEEQR   180
NGFIQSLKDD PSQSANLLAE AKKLNDSQAP KADNKFNKEQ QNAFYEILHL PNLTEEQRNG   240
FIQSLKDDPS VSKEILAEAK KLNDAQAPKD EDNNKPGKED GNKPGKEDGN KPGKEDGNKP   300
GKEDGNKPGK EDGNKPGKED GNKPGKEDGN KPGKEDGNKP GKEDGNKPGK EDGNKPGKED   360
GNGVHVVKPG DTVNDIAKAH GTTADKIAAD NKLADKNMIK PGQELVVDKK QQANHAEANK   420
AQALPETGEE NPFIGTTVFG GLSLALGAAL LAGRRREL                           458

SEQ ID NO: 58           moltype = AA  length = 195
FEATURE                 Location/Qualifiers
REGION                  1..195
                        note = Description of Artificial Sequence: Synthetic
                         polypeptide
VARIANT                 31
                        note = This site may encompass 3-13 amino acids, where X is
                         any amino acid
VARIANT                 46
                        note = This site may encompass 7-19 amino acids, where X is
                         any amino acid
VARIANT                 79
                        note = This site may encompass 3-25 amino acids, where X is
                         any amino acid
source                  1..195
                        mol_type = protein
                        organism = synthetic construct
SEQUENCE: 58
DVQLVESGGG LVQPGGSRKL SCAASGFTFS XWVRQAPEMG LEWVAXRFTI SRDNPKNTLF    60
LQMTSLRSED TAMYYCARXW GQGTSVTVSS ASTKGPSVFP LAPSSKSTSG GTAALGCLVK   120
DYFPEPVTVS WNSGALTSGV HTFPAVLQSS GLYSLSSVVT VPSSSLGTQT YICNVNHKPS   180
NTKVDKKVEP KSCGS                                                   195

SEQ ID NO: 59           moltype = AA  length = 190
FEATURE                 Location/Qualifiers
source                  1..190
                        mol_type = protein
                        organism = synthetic construct
VARIANT                 24
                        note = This site may encompass 3-17 amino acids, where X is
                         any amino acid
VARIANT                 41
                        note = This site may encompass 3-17 amino acids, where X is
                         any amino acid
VARIANT                 74
                        note = This region may encompass 3-25 amino acids, where X
                         is any amino acid
REGION                  1..190
                        note = Description of Artificial Sequence: Synthetic
                         polypeptide
SEQUENCE: 59
NIMLTQSPSS LAVSAGERVT MSCXWYQQKP GQSPKLLIYW XGVPDRFTGS GSGTDFTLTI    60
NSVQPEDLAV YYCXGGGTKL EIKRTVAAPS VFIFPPSDEQ LKSGTASVVC LLNNFYPREA   120
KVQWKVDNAL QSGNSQESVT EQDSKDSTYS LSSTLTLSKA DYEKHKVYAC EVTHQGLSSP   180
VTKSFNRGEC                                                         190
```